United States Patent
Federspiel et al.

(10) Patent No.: US 10,577,591 B2
(45) Date of Patent: Mar. 3, 2020

(54) MUMPS VIRUS AS A POTENTIAL ONCOLYTIC AGENT

(71) Applicant: Mayo Foundation for Medical Education and Research, Rochester, MN (US)

(72) Inventors: Mark J. Federspiel, Rochester, MN (US); Arun Ammayappan, Rochester, MN (US); Gennett Pike, Stewartville, MN (US); Stephen James Russell, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 41 days.

(21) Appl. No.: 15/735,761

(22) PCT Filed: Jun. 10, 2016

(86) PCT No.: PCT/US2016/036944
§ 371 (c)(1),
(2) Date: Dec. 12, 2017

(87) PCT Pub. No.: WO2016/201265
PCT Pub. Date: Dec. 15, 2016

(65) Prior Publication Data
US 2018/0187163 A1 Jul. 5, 2018

Related U.S. Application Data

(60) Provisional application No. 62/175,099, filed on Jun. 12, 2015.

(51) Int. Cl.
| | | |
|---|---|---|
| *A61P 35/00* | (2006.01) | |
| *C12N 7/00* | (2006.01) | |
| *A61K 39/12* | (2006.01) | |
| *A61P 35/02* | (2006.01) | |
| *A61K 31/519* | (2006.01) | |
| *A61K 39/00* | (2006.01) | |
| *A61K 39/165* | (2006.01) | |

(52) U.S. Cl.
CPC .............. *C12N 7/00* (2013.01); *A61K 31/519* (2013.01); *A61K 39/0011* (2013.01); *A61K 39/12* (2013.01); *A61K 39/165* (2013.01); *A61P 35/00* (2018.01); *A61P 35/02* (2018.01); *A61K 2039/525* (2013.01); *C12N 2760/18721* (2013.01); *C12N 2760/18734* (2013.01)

(58) Field of Classification Search
None
See application file for complete search history.

(56) References Cited

U.S. PATENT DOCUMENTS

| | | | | |
|---|---|---|---|---|
| 7,361,496 | B1 * | 4/2008 | Clarke | A61K 39/165 |
| | | | | 435/235.1 |
| 7,759,104 | B2 * | 7/2010 | Federspiel | C12N 7/00 |
| | | | | 424/212.1 |
| 7,781,413 | B2 * | 8/2010 | Minna | G01N 33/57484 |
| | | | | 435/320.1 |
| 2010/0297072 | A1 | 11/2010 | DePinho | |

FOREIGN PATENT DOCUMENTS

| | | |
|---|---|---|
| WO | WO 2008/043576 | 4/2008 |
| WO | WO 2010/005696 | 1/2010 |
| WO | WO 2014/022138 | 2/2014 |
| WO | WO 2014/053852 | 4/2014 |
| WO | WO 2014/199166 | 12/2014 |

OTHER PUBLICATIONS

Smorodintsev (AJPH, 1960).*
Extended European Search Report in European Application No. 16808400.2 dated Dec. 11, 2018, 294 pages.
Myers et al., "Oncolytic activities of approved mumps and measles vaccines for therapy of ovarian cancer," Cancer gene therapy, 12(7):593-599, Mar. 2005.
Ammayappan et al., "Neuroattenuation of vesicular stomatitis virus through picornaviral internal ribosome entry sites," J Virol., 87(6):3217-3228, Mar. 2013.
Asada, "Treatment of human cancer with mumps virus," Cancer, 34:1907-28, Dec. 1974.
Cox et al., "The Paramyxovirus Polymerase Complex as a Target for Next-Generation Anti-Paramyxovirus Therapeutics," Frontiers in Microbiology, 459(6):1-14, May 12, 2015.
Escobar-Zarate et al., "Overcoming cancer cell resistance to VSV oncolysis with JAK1/2 inhibitors," Cancer Gene Ther, 20(10):582-589, Oct. 2013.
Hosai et al., "Studies on live attenuated mumps virus vaccine. 1. Attenuation of mumps virus by serial passage in the chorioallantoic cavity of developing chick embryos and field trials by the inhalation method," Biken J., 13(2):121-6, Jun. 1970.
Norton et al., "Initiation and regulation of paramyxovirus transcription and replication," Virology, 479-480:545-554, Feb. 13, 2015.
Okuno et al., "Studies on the use of mumps virus for treatment of human cancer," Biken J., 2:37-49, Jun. 1, 1978.
Russell et al., "Oncolytic Virotherapy," Nat Biotechnol, 30(7):658-670, Jan. 10, 2014.
Shimizu et al., "Immunotherapy of advanced gynecologic cancer patients utilizing mumps virus," Cancer Detect Prev., 12(1-6):487-95, Jan. 1, 1988.
Yamada et al., "Abortive infection of mumps virus in murine cell lines," J Gen Virol, 65:973-980, May 1984.

* cited by examiner (Continued)

Primary Examiner — Agnieszka Boesen
(74) Attorney, Agent, or Firm — Fish & Richardson P.C.

(57) ABSTRACT

This document relates to methods and materials for virotherapy. For example, this document provides methods and materials for treating cancer using a recombinant mumps virus as an oncolytic agent.

22 Claims, 34 Drawing Sheets
Specification includes a Sequence Listing.

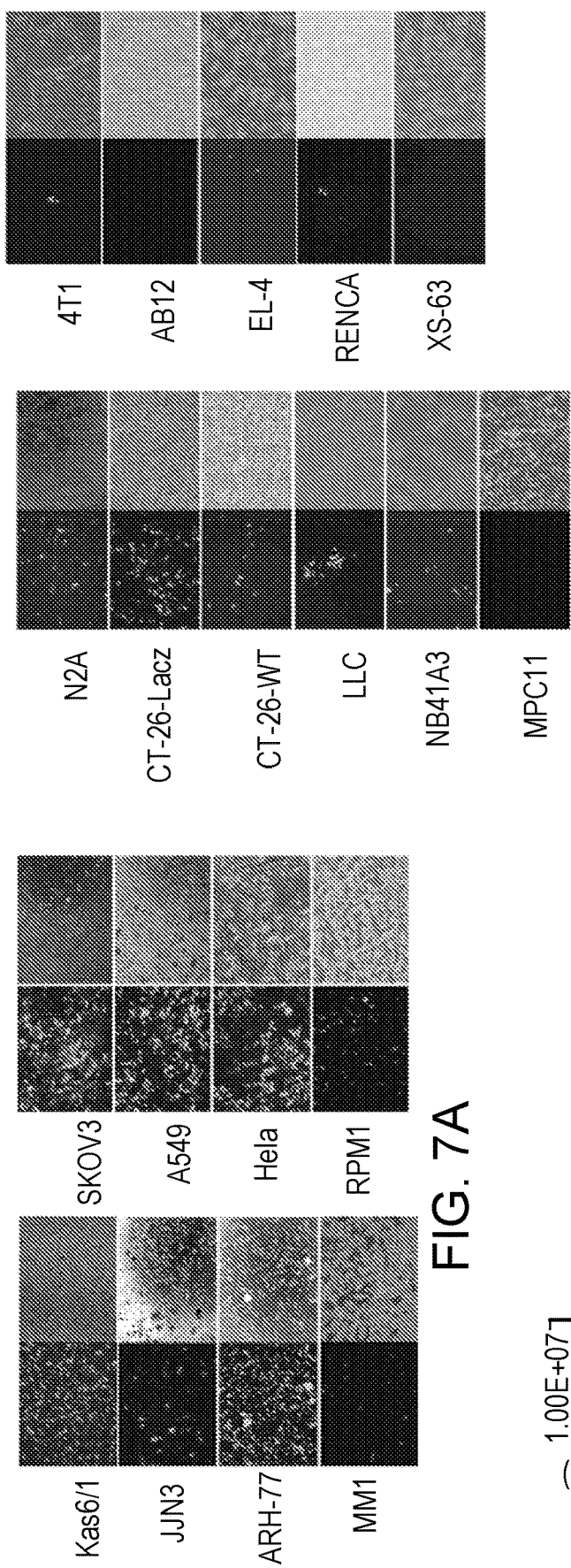
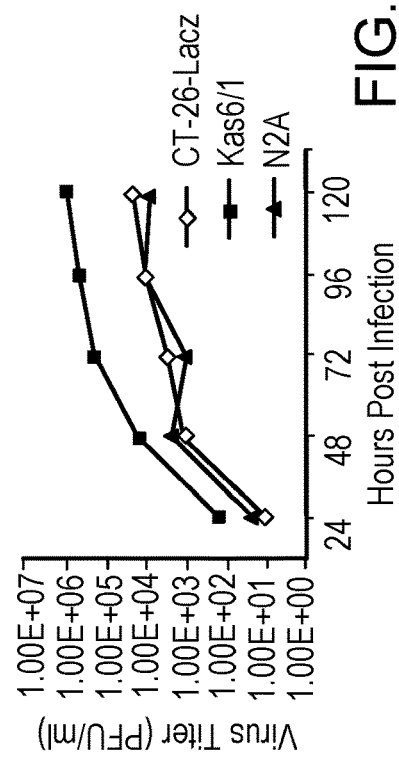
FIG. 7A
FIG. 7B
FIG. 7C

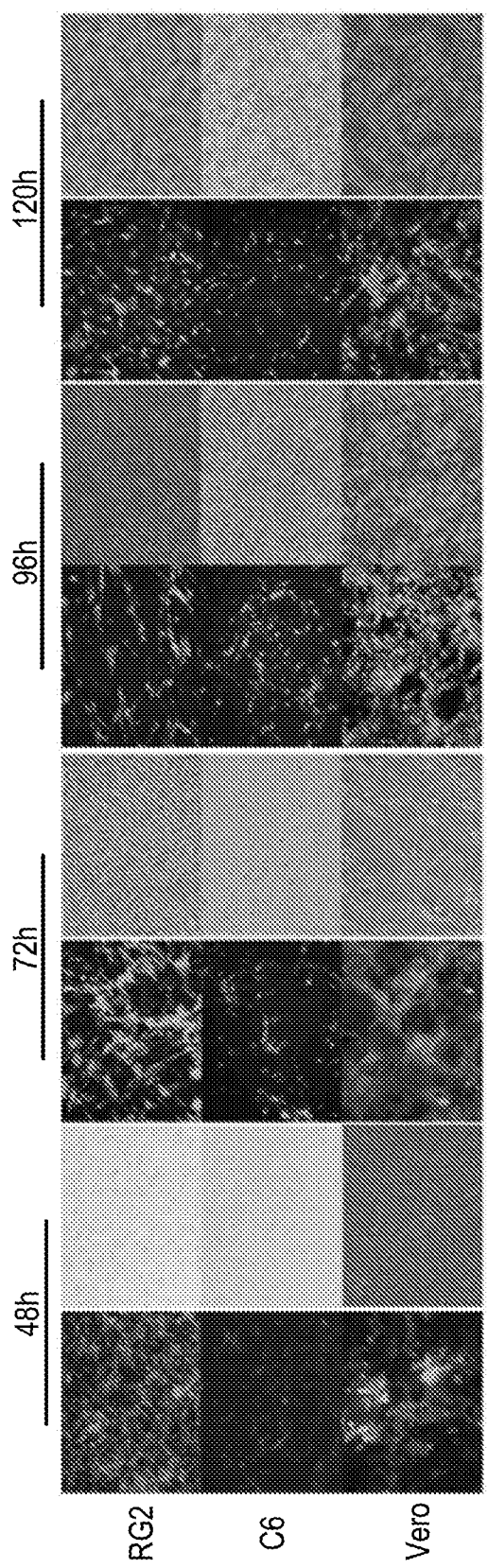
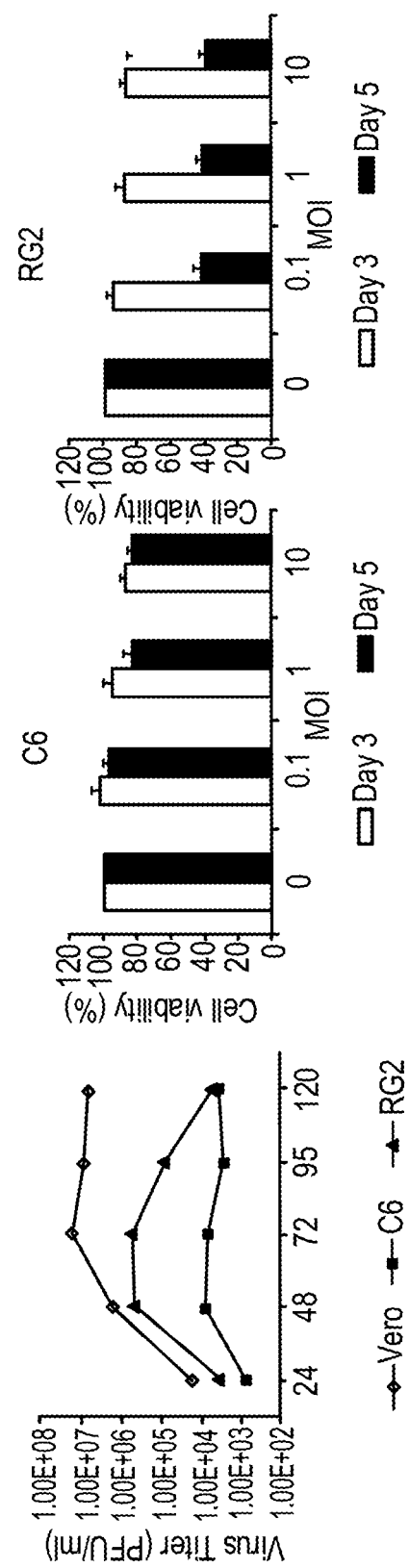
FIG. 9A
FIG. 9B
FIG. 9C

MuV-UC-WT

FIG. 13A

MuV-UC-GFP-L13328

FIG. 13B

Urabe mumps virus sequence (SEQ ID NO:1)

```
   1 accaagggga aaatggagat gggatgttgg tagaacaaat agtgtaagaa acagtaagcc
  61 cggaagtggt gtttttgcgat ttcgaggccg ggctcgatcc tcaccttca ttgtcgatag
 121 gggacatttt gacactacct ggaaaatgtc gtctgtgctc aaagcatttg agcgattcac
 181 gatagaacag gaacttcaag acaggggtga ggagggttca attccgccgg agactttaaa
 241 gtcagcagtc aaagtcttcg ttattaacac acccaatccc accacacgct accagatgct
 301 aaacttttgc ctaaggataa tctgcagtca aaatgctagg gcatctcaca gggtaggtgc
 361 attgataaca ttattctcac ttccctcagc aggcatgcaa aatcatatta gattagcaga
 421 tagatcacct gaagctcaga tagaacgctg tgagattgac ggttttgagc ctggcacata
 481 taggctaatt ccgaatgcac gcgccaatct tactgccaat gaaattgctg cctatgcttt
 541 gcttgcagac gacctccctc aaccataaaa taatggaact ccctatgtac atgcagatgt
 601 tgaaggacag ccatgtgatg agattgagca attcctagat cgatgctaca gtgtactaat
 661 ccaggcttgg gtgatggtct gtaaatgtat gacagcgtac gaccaacatg ctggatctgc
 721 tgatcggcgg tttgcaaaat accagcaaca aggtcgcctg gaagcaagat acatgctgca
 781 gccggaggcc caaaggttga tccaaactgc catcaggaaa agtcttgttg ttagacagta
 841 ccttactttc gaactccagt tggcaagacg gcaggggttg ctatcaaaca gatactatgc
 901 aatggtgggt gacattggaa agtacattga gaattcaggc cttactgcct tcttttctcac
 961 cctcaaatat gcactaggta ccaaatggag tcctctgtca ttggccgcat tcaccggtga
1021 actcactaag ctccgatccc tgatgatgtt atatcgagat ctcggagaac aagccagata
1081 ccttgctttg ttggaggctc ccaaataat ggactttgca cccggaggct acccattgat
1141 attcagttat gctatgggag tcggtacagt cctagatgtc caaatgcgaa attacactta
1201 tgcacgacct ttcctaaatg gttattattt ccagattggg gttgagactg cacgacggca
1261 acaaggcact gttgataaca gagtagcaga tgatctaggc ctgactcctg agcaaaggac
1321 tgaggttact caacttgttg acaggcttgc aaggggcaga ggtgcgggga taccaggtgg
1381 gcccgtgaat ccttttgttc ctccagttca acagcaacaa cctgctgccg cacatgagga
1441 cacccctgca ttggaggaat cagacgacga cggcgatgaa gacggggtg caggactcca
1501 aaatggagca caagcaccag ctgcaagaca gggaggccaa aatgacttca gagtacagcc
1561 actacaggat ccaattcaag cacaactttt catgccatta tatcctcaag tcagcaacat
1621 cccaaatcat cagaatcatc agatcaatcg cgtcggggg atggaacacc aagatttatt
1681 acgatacaac gagaatggtg atcctcaaca agatgcaagg ggcgaacacg gaaacacctt
1741 cccaaacaat cctaatcaaa acgcacagtc gcaagtgggc gactgggatg agtaaatcac
1801 tgacatgatc aaactacccc caattgcaat aaccccagga caatctagcc acagctaact
1861 gcccaaatcc actacattcc attcatattt agtctttaag aaaaaattag gccgggaaag
1921 aattagttct acgagcatcg acacaattat cttgatcgtg tttctttcg ggcaagccat
1981 ggaccaattt ataaaacaag atgagactgg tgatttaatt gagacaggaa tgaacgttgc
2041 aaatcatttc ctatccgccc ccattcaggg aaccaactcg ttgagcaagg ccacaatcat
2101 ccctggcgtt gcaccagtac tcattggcaa tccagagcaa aagaacattc agtaccccac
2161 cacatcacat caggggtcca agtcaaaggg cagaggctca ggggccaggc ccatcatagt
2221 ctcatcctcc gaaggaggca ctggagggac tcagattcct gagcccctt tcgcacaaac
2281 aggacaaggt ggcattgtca ccaccgttta tcaggatcca actatccaac caacaggttc
2341 atatcgaagt gtggaattgg ctaagatagg aaaagagaga atgattaatc gatttgttga
2401 aaaaccaaga acctcaacgc cggtaacaga atttaagagg ggggccggga gcggctgctc
2461 aaggccagac aatccaagag gagggcatag acgggaatgg agcctcagct gggtccaagg
2521 agaggtccgg gtctttgagt ggtgcaaccc catatgctca cctatcactg ccacagcaag
2581 attccactcc tgcaaatgtg ggaattgccc cgcaaagtgc gatcagtgcg aacgagatta
2641 tggacctcct tagagggatg gatgctcgcc tgcaacatct tgaacaaag gtggacaagg
2701 tgcttgcaca gggcagcatg gtgacccaaa taaagaatga attatcaaca gtaaagacaa
```

FIG. 16

Urabe mumps virus sequence (SEQ ID NO:1) cont.

```
2701 tgcttgcaca gggcagcatg gtgacccaaa taaagaatga attatcaaca gtaaagacaa
2761 cactagctac aattgaagga atgatggcga cagtaaagat catggatcct ggaaacccga
2821 caggggtccc agttgatgag cttagaagaa gttttagtga tcatgtaaca attgttagtg
2881 gaccaggaga tgtgtcattc agctccggtg aagaacccac actgtatttg gatgaactag
2941 cgaggcctgt cccaaagccc cgtcctgcaa agcagccaaa accccaacca gtaaaggatt
3001 tagcaggacg gaaagtgatg ataactaaaa tgatcactga ctgtgtggcc aatcctcaaa
3061 tgaagcaggt gtttgagcaa cgattggcaa gagccagcac cgaggatgct ctgaatgata
3121 tcaagcgaga catcataagg agcgccatat gaactcacca ggaacaccag actcacggga
3181 aaatccacaa actgaaagcc acaatgattc cctgttaaat aaaaaataag cacgaacaca
3241 agtccaatcc aaccatagca gcaatggccg ggtcacagat caaaatccct cttccaaagc
3301 cccctgattc agactctcaa agactaaatg cattccctgt aatcgtggct caagaaggca
3361 aaggacgact cctcagacag atcagactta ggaaaatatt atcaggggat ccgtctgatc
3421 atcaaattac atttgtgaat acatatggat tcatccgtgc cactccagaa acatccgagt
3481 tcatctctga atcatcacaa cagaaggtga ctcctgtagt gacggcgtgc atgctgtcct
3541 tcggcgctgg accagtccta gaagacccac aacatatgct gaaagctctt gatcagacag
3601 acatcagggt tcggaagaca gcgagtgata aagagcagat cttattcgag atcaaccgca
3661 tccccaatct attcaggcat catcaaatat ctgcggacca tctgattcaa gccagctccg
3721 ataaatatgt caagtcacca gcaaagttga ttgcaggagt aaattacatc tactgtgtca
3781 cattttatc tgtgacagtt tgttctgcct cactcaagtt tcgagttgcg cgccattgc
3841 ttgctgcacg atctagatta gtaagagcag ttcagatgga agttttgctt cgagtaactt
3901 gcaaaaagga ttcccaaatg gcaaagagca tgttaaatga ccctgatgga gaagggtgca
3961 ttgcatccgt gtggttccac ctgtgtaatc tgtgcaaagg caggaataaa cttagaagtt
4021 acgatgaaaa ttattttgca tctaagtgcc gtaagatgaa tctgacagtc agcataggag
4081 acatgtgggg accaaccatt ctagtccatg caggcggtca cattccgaca actgcaaaac
4141 cttttttcaa ctcaagaggc tgggtctgcc accccatcca ccaatcatca ccatcgttgg
4201 cgaagaccct atggtcatct gggtgtgaaa tcaaggctgc cagtgctatc ctccagggct
4261 cagactatgc atcacttgca aaaactgatg acataatata ttcaaagata aaagtcgata
4321 aagatgcggc caactacaaa ggagtatcct ggagtccatt caggaagtct gcctcaatga
4381 gcaacctatg agaatttcat ctattccccc tgatgcctcc aggagaatca acaatcagtc
4441 cgattttacc ggtggtaact tgattgaaat tatagaaaaa ataagcctag aaggacatct
4501 tacttctcga cttttccaact ttgaaaatag aattgatcag taatcatgaa ggcttttta
4561 gttacttgct taagctttgc agtctttttca tcttctgtat gtgtgaatat caacatcttg
4621 cagcaaattg gatatatcaa gcaacaagtc aggcaactaa gctattactc acaaagttca
4681 agctcctaca tagtggtcaa gcttttaccg aatatccaac ccattgataa cagctgtgaa
4741 tttaagagtg taactcaata caataagacc ttgagtaatt tgcttcttcc aattgcagaa
4801 aacataaaca atattgcatc gccctcatct gggtcaagac ggcataaaag gtttgctggt
4861 attgctattg gcattgctgc gctcggtgtt gcgaccgcag cacaagtaac tgccgctgtc
4921 tcattagttc aagcacagac aaatgcacgt gcaatagcgg cgatgaaaaa ttcaatacaa
4981 gcaactaatc gagcagtctt cgaagtgaag gaaggcactc aacagttagc tatagcggta
5041 caagcaatac aagaccacat caatactatt atgaacaccc aattgaacaa tatgtcttgt
5101 cagatccttg ataaccagct tgcaactttc ctaggattat acctaacaga attaacaaca
5161 gtgtttcagc cacaattaat taatccggca ttgtcaccga ttagtataca agccttgagg
5221 tctttgcttg gaagtatgac gcctgcagtg gtccaagcaa cattatctac ttcaatctct
5281 actgctgaaa tactaagtgc cggtctaatg gagggtcaga ttgtttctgt tctgctagat
5341 gagatgcaga tgatagttaa gataaatatt ccaactattg tcacacaatc aaatgcattg
5401 gtgattgact ctactcaat ttcgagcttt attaataatc aggaatccat aatccaattg
```

FIG. 16 (CONT)

Urabe mumps virus sequence (SEQ ID NO:1) cont.

```
5401 gtgattgact tctactcaat ttcgagcttt attaataatc aggaatccat aatccaattg
5461 ccagacagaa tcttggagat cgggaatgaa caatggagct atccagctaa aaattgtaag
5521 ttgacaagac accacatatt ctgccaatac aatgaggcag agaggctgag cctagaatca
5581 aaactatgcc ttgcaggcaa tataagtgcc tgtgtgttct cacccatagc agggagttat
5641 atgaggcgat ttacggcact ggatggaaca attgttgcaa actgtcgaag tctaacgtgt
5701 ctatgcaaga atccatctta tcctatatac caacctgacc atcatgcagt cacgaccatt
5761 gatctaaccg catgtcaaac attgtcccta gacggattgg atttcagcat tgtctctcta
5821 agcaacatca cttacgctga gaaccttacc atttcattgt ctcagacaat caatactcaa
5881 cccattgaca tatcaactga actgagtaag gttaatgcat ccctccaaaa tgccgttaag
5941 tacataaagg agagcaacca tcagctccaa tctgtgagtg taaactccaa aatcggagct
6001 ataattgtag cagccttagt tttgagcatt ctgtcaatta tcatttcgct attgtttgc
6061 tgctgggctt acattgcaac taaagaaatc agaagaatca acttcaaaac aaatcatatc
6121 aatacaatat caagtagtgt cgatgatctc attaggtact aatcctaaca ttgtgattca
6181 tcctgcattg agaaaagatt tagaaaaaaa ctaaattaag aatgaatctc ctggggtcgt
6241 aacgtctcgt gaccctgccg ttgcactatg ccggcgatcc aacctccctt atacccaaca
6301 tttctattgc taattcttct ctctctgatc gtaactttgt atgtctggat tatatcaacc
6361 atcacttaca agactgtggt gcgacatgca gcactgtacc agagatcctt ctttcgctgg
6421 agttttgatc actcactcta gaaagatctc cagctgggac aagtcccaat ccatcatgcg
6481 agaacaagct gcatccaaat gatgccgttc aatcatgaga cataaagaaa aaatcaagcc
6541 agaacaagct taggatcaca atacaacaca gaaccccagc tgccatcata actgttctct
6601 ggccgctcga aagatggagc cctcaaaact cttcacaatg tcagacaatg ccaccttttgc
6661 acctggacct tttatcaatg cggcagacaa gaagacgttc cgaacctgct tccgaatatt
6721 ggtactgtct gtacaagctg ttaccttat attagttatt gtcactttag gtgagcttgt
6781 gaggatgatc aatgatcaag gcttgagcaa tcagttgtct tcaattgcag acaagataag
6841 agagtcagct actatgattg catctgctgt gggagtaatg aatcaagtta ttcacggagt
6901 aacggtatcc ttaccctac aaattgaggg aaaccaaaat caattgttat ccacacttgc
6961 cacaatctgt acaggcaaaa aacaagtctc aaactgctct acaaacatcc ccttagttaa
7021 tgaccttagg tttataaatg ggatcaataa attcatcatt gaagattatg caactcatga
7081 tttctctatc ggccatccac tcaacatgcc tagctttatc ccaactgcaa cttcacccaa
7141 tggttgcaca agaattccat ccttttctct aggtaagaca cactggtgct acacacataa
7201 tgtaattaat gccaactgca aggatcatac ttcgtctaac aatatatttt ccatggggat
7261 actcgttcag accgcgtcag ggtatcctat gttcaaaacc ttaaaaatcc aatatctcag
7321 tgatggcctt aatcggaaaa gctgctcaat tgcaacagtc cctgatggat gcgcaatgta
7381 ctgttacgtc tcaactcaac ttgaaaccga cgactatgcg gggtccagcc cacctaccca
7441 gaaacttacc ctgttattct ataatgatac cgtcacagaa aggacaatat ctccaactgg
7501 tcttgaaggg aattgggcta ctttggttcc aggagtgggg agtggaatat atttcgagaa
7561 taaattgatt tttcctgcat atggggggtgt cttgcccaat agtacactcg gagttaaatc
7621 agcaagagaa ttttccggc ctgttaatcc atataatcca tgttcaggac cacaacaaga
7681 tttagatcag cgtgctttga gatcatactt cccaagttac ttctctaatc gaagagtaca
7741 gagtgcattt cttgtctgtg cctggaatca gatcctagtt acaaattgcg agctagttgt
7801 cccctcaaac aatcagacac tgatgggtgc agaaggaaga gtttattga tcaataatcg
7861 actattatat tatcagagaa gtaccagctg gtggccgtat gaactcctct atgagatatc
7921 attcacattt acaaactctg gtcaatcatc tgtgaatatg tcctggata ctatatattc
7981 attcactcgt cctggttcag gcaactgcag tggtaaaaat gtgtgcccaa ctgcttgtgt
```

FIG. 16 (CONT)

Urabe mumps virus sequence (SEQ ID NO:1) cont.

```
 8041 gtcaggggtt tatcttgatc cctggccatt aactccatat agccaccaat caggcattaa
 8101 ccgaaatttc tatttcacag gcgcactatt aaattcaagc acaactagag taaatcctac
 8161 cctttatgtc tctgcccttg ataatcttaa agtactagcc ccatatggta atcagggact
 8221 gtttgcctcg tacaccacaa ccacctgctt tcaagatacc ggtgatgcta gtgtgtattg
 8281 tgtttatatt atggaactag catcgaatat cgttggagaa ttccaaattc tacctgtgct
 8341 aaccagattg accatcactt gagtcatagt gaatgcagtg ggaggcccta tgggcgtgct
 8401 tcaatcttta tcgattatta agaaaaaaca ggccagaatg gcgggcctaa atgagatact
 8461 cttacctgaa gtacatttaa actcacccat cgttagatat aagcttttct actatatatt
 8521 gcatggccag ttaccaaatg atttggagcc agatgacttg ggcccactag caaatcagaa
 8581 ttggaaggca attcgagctg aagaatctca ggttcatgca cgtttaaaac agatcagagt
 8641 agaactcatt gcaaggattc ctagtctccg gtggacccgc tctcagaggg agattgccat
 8701 actcatttgg ccaagaatac ttccaatcct gcaagcatat gatcttcggc aaagtatgca
 8761 attgcccaca gtatgggaga aattgactca atccacagtt aatcttataa gtgatgggct
 8821 agaacgggtt gtattacaca tcagcaatca gctgacaggc aagcctaact tgtttaccag
 8881 atctcgagca ggacaagacg caaaggatta ctcaattcca tccactagag agctatctca
 8941 aatatggttt aacaacgagt ggagtggatc tgtaaagacc tggcttatga ttaaatatag
 9001 aatgaggcag ctaatcacaa accaaaagac aggtgagtta acagatttag taaccattgt
 9061 ggatactagg tccactctat gcattattgc cccagaatta gttgctttat actccaatga
 9121 gcacaaagca ttaacgtacc tcacctttga aatggtatta atggtcactg atatgttaga
 9181 gggacgactt aatgtttctt ctttatgcac agctagtcat tatctgtccc ctctaaagaa
 9241 gagaatcgaa attctcctaa cattagttga tgaccttgct ctacttatgg gggacaaagt
 9301 atacggtgtt gtctcttcac ttgagagttt tgtttacgcc caattacagt atggtgatcc
 9361 tgttgtagac attaagggta cattctacgg atttatatgt aatgagattc tcgacctact
 9421 gactgaagac aacatcttta ctgaagagga ggcaaacaag gttcttctgg acttgacatc
 9481 acagtttgac aatctatccc ctgatttaac tgctgagctc ctctgcatta tgagactttg
 9541 gggccatccc acattaactg ccagccaagc agcatccaag gtccgagagt ccatgtgtgc
 9601 tcctaaggtg ttagatttcc aaacaataat gaagaccctg gctttctttc acgcaatcct
 9661 gattaacggt tataggagga gccataatgg aatctggcct cctactactc ttcatggcaa
 9721 tgcccccaaa agcctcattg agatgcggca tgataattca gagcttaagt atgagtatgt
 9781 cctcaagaat tggaaaagta tatctatgtt aagaatacac aaatgctttg atgcatcacc
 9841 tgatgaagat ctcagcatat tcatgaaaga taaggcaatc agctgtccaa agcaagactg
 9901 gatgggagta tttaggagga gcctgataaa acagcgatat cgtgatgcga atcggcctct
 9961 accacaacca tccaaccgac ggctactgtt gaattttcta gaggatgaca gattcgatcc
10021 cattaaggag cttgagtatg tcaccagtgg agaatatctt agggacctg aattttgtgc
10081 atcttactct ctcaaggaga aggagataaa ggctacaggt cgcatatttg ccaaaatgac
10141 aaagagaatg aggtcgtgcc aagtaattgc agaatcattg ttggccaatc atgcaggtaa
10201 attaatgaga gagaatggag ttgtcttaga ccagttaaaa ttgacaaaat ctttgttaac
10261 gatgaaccaa attggtatta tatcagagca cagccgaaga tccactgctg acacatgac
10321 tttggcacac tccggttcaa ataagcacag aattaataat agtcaattca gaagaataa
10381 agacagtaag catgagatgc ctgatgatgg gtttgagata gcagcctgct ttctaacaac
10441 tgacctcaca aaatactgct taaattggag gtaccaagtc atcatccct tgcgcgtac
10501 attgaattca atgtatggta taccccacct gtttgaatgg atacatttaa ggctaatgcg
10561 aagcactctc tatgttggtg atccttcaa tcctccatca gatcctaccc aacttgacct
```

```
Urabe mumps virus sequence (SEQ ID NO:1) cont.
10621 tgatacagct ctcaatgatg atatatttat agtttctcct cgtggaggaa tcgagggttt
10681 atgtcaaaaa ttatggacta tgatttccat ctcgacaatc atattatccg caactgaggc
10741 aaacactaga gttatgagca tggttcaggg tgacaaccaa gcaattgcaa tcaccactag
10801 agtagtacgc tcgctcagtc attccgagaa gaaggagcaa gcttataaag caagtaaatt
10861 attctttgaa aggcttaaag ctaacaacca tggaattgga caccacttaa aagaacaaga
10921 aacaatcctt agttctgatt tcttcatata cagtaagagg gtgttttaca aaggtcgaat
10981 tttgactcaa gcgttaaaga acgtgagcaa gatgtgctta acagctgaca tactagggga
11041 ctgttcacaa gcatcatgct ccaatttagc tactactgta atgcgcctga ctgagaatgg
11101 ggtcgagaaa gatttgtgtt attttctaaa tgcattcatg acaatcagac aattatgtta
11161 tgatctggta ttccccaaa ctaaatctct tagtcaggac atcactaatg cttatcttaa
11221 tcatccaata cttatctcaa gattgtgtct attaccatct caattagggg gcctaaactt
11281 tctctcgtgt agtcgcctgt tcaatagaaa cataggagac ccattagtgt ctgcaattgc
11341 tgatgtgaaa cgattaatta aagctggctg tctagatatc tgggtcctgt ataacatcct
11401 tgggaggagg cctggaaaag gtaagtggag cactctggca gctgatcctt atactttaaa
11461 catagattat ttagttcctt caacaacttt tttaaagaag catgcccaat atacattgat
11521 ggaacggagt gttaatccca tgctccgtgg agtattcagc gaaaatgcag ctgaggaaga
11581 agaggaactc gcacagtatc tattagatcg tgaggtagtc atgcccagag ttgcacatgt
11641 aatacttgcc cagtctagtt gcggcagaag aaaacagatt caaggttact tggattccac
11701 tagaactatt atcaggtatt cactggaggt gagaccattg tcagaaaga agctgaatac
11761 agtaatagaa tataactat tgtatctttc ctacaatttg gagattattg aaaaacccaa
11821 tatagtccaa ccttttttga atgcaatcaa tgttgatact tgtagcatcg atatagctag
11881 gtcccttaga aaactatcct gggcaacttt actgaacgga cgtcccatcg agggattaga
11941 aacacctgat cccattgaat tggtacatgg gtgtttgatc attgggtcag atgaatgtga
12001 gcattgcagc agtggtgatg acaagttcac ctggtttttc ctacccaagg ggataaggct
12061 agataatgat ccggcgtcca acccacccat cagagtacct tatattggat ctaaaacaga
12121 tgaacggagg gttgcgtcaa tggcttacat caaaggagca tctgtatcac ttaaatcagc
12181 actcagacta gcgggagtat atatttgggc tttcggagat acagaggaat catggcagga
12241 tgcctatgag ttagcttcca ctcgtgttaa tctcacacta gagcaattgc aatctctcac
12301 tccttaccaa acatctgcta acctagtcca cagattggat gatggcacta ctcaattaaa
12361 atttaccct gcaagctcct atgcattctc tagcttcgtt catatatcta atgactgtca
12421 agttcttgag atcgatgatc aggtaacaga ttctaacctg atttaccagc aagttatgat
12481 tactggcctt gctttaattg agacatggaa caatcctcca atcaacttct ccgtttatga
12541 aactacacta cacttgcaca caggctcatc ttgctgtata agacctgtcg agtcttgtgt
12601 agtaaatcct ccttttgcttc ctgtccccctt cattaatgtc cctcaaatga ataaatttgt
12661 atatgaccct gaaccgctca gtttgctaga gatggaaaaa attgaggaca ttgcttatca
12721 aaccagaatt ggtggtttag atcaaatccc acttctggaa aaaatacccct tactagctca
12781 cctcaccgcc aagcagatgg taaatagcat caccgggctt gatgaagcaa catctatagt
12841 aaatgacgct gtggttcaag cagactatac tagcaattgg attagtgaat gctgttacac
12901 ttacattgat tctgtgtttg tttactctgg ctgggcatta ttattggaac tttcgtacca
12961 aatgtactac ttaagaattc aaggcatcca aggaattcta gactatgtgt atatgacctt
13021 gaggaggata ccaggaatgg ctataacggg catctcatcc acaattagtc accctcgtat
13081 actcagaaga tgcatcaatc tggatgtcat agccctatc aattctccac acatagcttc
13141 actggattac acaaaattga gcatagacgc agtaatgtgg ggaactaagc aggttttgac
13201 caacatttcg caaggtatcg attatgagat agttgttcct tctgaaagcc aactcacact
13261 cagtgataga gttctaaatc tagttgctcg aaaactatca ctactggcaa tcatctgggc
13321 caattataac tatcctccaa aggttaaagg tatgtcacct gaggacaaat gtcaggcttt
```

FIG. 16 (CONT)

Urabe mumps virus sequence (SEQ ID NO:1) cont.

```
13381 aactacccat ctactccaaa ctgtcgaata tgttgagcac attcagattg aaaagacgaa
13441 catcaggagg atgattattg aaccaaaatt aactgcctac cctagtaatt tgttttatct
13501 atctcgaaag ctgcttaatg caattcgaga ttctgaagaa ggacaatttc tgattgcatc
13561 ctattataac agctttggat atctggaacc aatactaatg gaatctaaaa tattcaatct
13621 aagttcatcc gaatcagcat cccttacaga atttgatttc atcctcaact tggaattgtc
13681 tgaagccagc cttgagaaat actctctccc aagtttgctt atgacggctg agaatatgga
13741 taacccattt cctcaacccc ccctccatca tgttctcaga ccactaggtt tatcatccac
13801 atcatggtat aaaacaatca gtgttttgaa ttatattagc catatgaaga tatctgacgg
13861 tgcccatcta tatttggcag agggaagtgg agcctctatg tcacttatag agactttctt
13921 gcccggtgaa gtaatatggt acaacagcct attcaatagt ggtgagaatc ctccccaacg
13981 caattttgcc cctttaccca cccagtttat tgaaagtgtc cctacagat tgattcaagc
14041 aggtatagca gcaggaagtg gtgtagttca aagtttctat ccactctgga cggtaatag
14101 cgatatcact gacttaagca cgaaaactag tgtcgagtac attattcaca aggtagggc
14161 tgatacatgt gcattggttc atgtggatct ggagggtgta cccggctcaa tgaacagtat
14221 gttggagaga gcccaagttc atgcgctact gatcacggta actgtactaa agccaggtgg
14281 cttactaatc ttgaaagctt catgggaacc ttttaatcga ttttccttt tactcacaat
14341 actctggcaa ttctttttcaa caataaggat ccttcgatct tcatactccg acccgaataa
14401 tcacgaggta tacataatag ctacattagc tgttgatccc accacatcct cctttacaac
14461 cgctctgaat agggcgcgta ctctgaatga acagggcttt tcactcatcc cacctgaatt
14521 agtgagtgag tactggagga ggcgtgttga acaagggcag attatacagg attgtataga
14581 taaagtcata tcagagtgtg ttagagacca atatctggca gacaacaata ttatccttca
14641 ggcggggggg actccaagca caagaaaatg gttggatctg cctgactatc cgtcgttcaa
14701 tgaattacaa tcggagatgg ccagactcat aacaattcat cttaaagagg taatagaaat
14761 cctaaagggc caatcatcag atcatgacac cctattattt acttcataca atgtaggtcc
14821 cctcgggaaa ataaatacaa tactcagatt gattgttgag agaattctta tgtacactgt
14881 aaggaactgg tgcatcttgc ccactcaaac tcgtctcacc ttacgacagt ctatcgagct
14941 tggagagttt agactaagag acgtgataac acccatggag atcctaaagc tatcccccaa
15001 ccggaagtat ctgaagtctg cattaaacca atcaacattc aatcatctaa tgggagaaac
15061 atctgacatg ttgttaaatc gatcctatca aaaagaatt tggaaagcca ttgggtgtgt
15121 aatctattgc tttggtttgc ttaccctga tgttgaagat tctgagcgca ttgatattga
15181 caatgatata cctgattatg atatccacgg ggacataatt taaatcgact aaagactcct
15241 ctggcatgat acgtcaccaa aaggttccac accagcatcc aaattcttct agaccgtaca
15301 cgacctcgaa caatcataac cacatcagta ttaaatccat aatatcattt taagaaaaaa
15361 ttgattttac tttctcccct tggt
```

FIG. 16 (CONT)

NP protein (SEQ ID NO:2)
MSSVLKAFERFTIEQELQDRGEEGSIPPETLKSAVKVFVINTPN
PTTRYQMLNFCLRIICSQNARASHRVGALITLFSLPSAGMQNHIRLADRSPEAQIERC
EIDGFEPGTYRLIPNARANLTANEIAAYALLADDLPPTINNGTPYVHADVEGQPCDEI
EQFLDRCYSVLIQAWVMVCKCMTAYDQHAGSADRRFAKYQQQGRLEARYMLQPEAQRL
IQTAIRKSLVVRQYLTFELQLARRQGLLSNRYYAMVGDIGKYIENSGLTAFFLTLKYA
LGTKWSPLSLAAFTGELTKLRSLMMLYRDLGEQARYLALLEAPQIMDFAPGGYPLIFS
YAMGVGTVLDVQMRNYTYARPFLNGYYFQIGVETARRQQGTVDNRVADDLGLTPEQRT
EVTQLVDRLARGRGAGIPGGPVNPFVPPVQQQQPAAAHEDTPALEESDDDGDEDGGAG
LQNGAQAPAARQGGQNDFRVQPLQDPIQAQLFMPLYPQVSNIPNHQNHQINRVGGMEH
QDLLRYNENGDPQQDARGEHGNTFPNNPNQNAQSQVGDWDE

P protein (SEQ ID NO:3)
MDQFIKQDETGDLIETGMNVANHFLSAPIQGTNSLSKATIIPGV
APVLIGNPEQKNIQYPTTSHQGSKSKGRGSGARPIIVSSSEGGTGGTQIPEPLFAQTG
QGGIVTTVYQDPTIQPTGSYRSVELAKIGKERMINRFVEKPRTSTPVTEFKRGGPGAA
AQGQTIQEEGIDGNGASAGSKERSGSLSGATPYAHLSLPQQDSTPANVGIAPQSAISA
NEIMDLLRGMDARLQHLEQKVDKVLAQGSMVTQIKNELSTVKTTLATIEGMMATVKIM
DPGNPTGVPVDELRRSFSDHVTIVSGPGDVSFSSGEEPTLYLDELARPVPKPRPAKQP
KPQPVKDLAGRKVMITKMITDCVANPQMKQVFEQRLARASTEDALNDIKRDIIRSAI

V protein (SEQ ID NO:4)
MDQFIKQDETGDLIETGMNVANHFLSAPIQGTNSLSKATIIPGV
APVLIGNPEQKNIQYPTTSHQGSKSKGRGSGARPIIVSSSEGGTGGTQIPEPLFAQTG
QGGIVTTVYQDPTIQPTGSYRSVELAKIGKERMINRFVEKPRTSTPVTEFKRGAGSGC
SRPDNPRGGHRREWSLSWVQGEVRVFEWCNPICSPITATARFHSCKCGNCPAKCDQCE
RDYGPP

I protein (SEQ ID NO:5)
MDQFIKQDETGDLIETGMNVANHFLSAPIQGTNSLSKATIIPGVAPVLIGNPEQKNIQ
YPTTSHQGSKSKGRGSGARPIIVSSSEGGTGGTQIPEPLFAQTG
QGGIVTTVYQDPTIQPTGSYRSVELAKIGKERMINRFVEKPRTSTPVTEFKRGGGRER
LLKARQSKRRA

FIG. 16 (CONT)

M protein (SEQ ID NO:6)
MAGSQIKIPLPKPPDSDSQRLNAFPVIVAQEGKGRLLRQIRLRKILSGDPSDHQITF
VNTYGFIRATPETSEFISESSQQKVTPVVTACMLSFGAGPVLEDPQHMLKALDQTDI
RVRKTASDKEQILFEINRIPNLFRHHQISADHLIQASSDKYVKSPAKLIAGVNYIYC
VTFLSVTVCSASLKFRVARPLLAARSRLVRAVQMEVLLRVTCKKDSQMAKSMLNDPD
GEGCIASVWFHLCNLCKGRNKLRSYDENYFASKCRKMNLTVSIGDMWGPTILVHAGG
HIPTTAKPFFNSRGWVCHPIHQSSPSLAKTLWSSGCEIKAASAILQGSDYASLAKTD
DIIYSKIKVDKDAANYKGVSWSPFRKSASMSNL F protein (SEQ ID NO:7)
MKAFLVTCLSFAVFSSSVCVNINILQQIGYIKQQVRQLSYYSQSSSSYIVVKLLPNI
QPIDNSCEFKSVTQYNKTLSNLLLPIAENINNIASPSSGSRRHKRFAGIAIGIAALG
VATAAQVTAAVSLVQAQTNARAIAAMKNSIQATNRAVFEVKEGTQQLAIAVQAIQDH
INTIMNTQLNNMSCQILDNQLATFLGLYLTELTTVFQPQLINPALSPISIQALRSLL
GSMTPAVVQATLSTSISTAEILSAGLMEGQIVSVLLDEMQMIVKINIPTIVTQSNAL
VIDFYSISSFINNQESIIQLPDRILEIGNEQWSYPAKNCKLTRHHIFCQYNEAERLS
LESKLCLAGNISACVFSPIAGSYMRRFTALDGTIVANCRSLTCLCKNPSYPIYQPDH
HAVTTIDLTACQTLSLDGLDFSIVSLSNITYAENLTISLSQTINTQPIDIS
TELSKVNASLQNAVKYIKESNHQLQSVSVNSKIGAIIVAALVLSILSIIISLLFCCW
AYIATKEIRRINFKTNHINTISSSVDDLIRY SH protein (SEQ ID NO:8)
MPAIQPPLYPTFLLLILLSLIVTLYVWIISTITYKTVVRHAALYQRSFFRWSFDHSL HN protein (SEQ ID NO:9)
MEPSKLFTMSDNATFAPGPFINAADKKTFRTCFRILVLSVQAVTLILVIVTLGELVR
MINDQGLSNQLSSIADKIRESATMIASAVGVMNQVIHGVTVSLPLQIEGNQNQLLST
LATICTGKKQVSNCSTNIPLVNDLRFINGINKFIIEDYATHDFSIGHPLNMPSFIPT
ATSPNGCTRIPSFSLGKTHWCYTHNVINANCKDHTSSNQYISMGILVQTASGYPMFK
TLKIQYLSDGLNRKSCSIATVPDGCAMYCYVSTQLETDDYAGSSPPTQKLTLLFYND
TVTERTISPTGLEGNWATLVPGVGSGIYFENKLIFPAYGGVLPNSTLGVKSAREFFR
PVNPYNPCSGPQQDLDQRALRSYFPSYFSNRRVQSAFLVCAWNQILVTNCELVVPSN
NQTLMGAEGRVLLINNRLLYYQRSTSWWPYELLYEISFTFTNSGQSSVNMSWIPIYS
FTRPGSGNCSGXNVCPTACVSGVYLDPWPLTPYSHQSGINRNFYFTGALLNSSTTRV
NPTLYVSALNNLKVLAPYGNQGLFASYTTTTCFQDTGDASVYCVYIMELASNIVGEF
QILPVLTRLTIT

FIG. 16 (CONT)

L protein (SEQ ID NO:10)
MAGLNEILLPEVHLNSPIVRYKLFYYILHGQLPNDLEPDDLGPLANQNWKAIRAEES
QVHARLKQIRVELIARIPSLRWTRSQREIAILIWPRILPILQAYDLRQSMQLPTVWE
KLTQSTVNLISDGLERVVLHISNQLTGKPNLFTRSRAGQDAKDYSIPSTRELSQIWF
NNEWSGSVKTWLMIKYRMRQLITNQKTGELTDLVTIVDTRSTLCIIAPELVALYSNE
HKALTYLTFEMVLMVTDMLEGRLNVSSLCTASHYLSPLKKRIEILLTLVDDLALLMG
DKVYGVVSSLESFVYAQLQYGDPVVDIKGTFYGFICNEILDLLTEDNIFTEEEANKV
LLDLTSQFDNLSPDLTAELLCIMRLWGHPTLTASQAASKVRESMCAPKVLDFQTIMK
TLAFFHAILINGYRRSHNGIWPPTTLHGNAPKSLIEMRHDNSELKYEYVLKNWKSIS
MLRIHKCFDASPDEDLSIFMKDKAISCPKQDWMGVFRRSLIKQRYRDANRPLPQPSN
RRLLLNFLEDDRFDPIKELEYVTSGEYLRDPEFCASYSLKEKEIKATGRIFAKMTKR
MRSCQVIAESLLANHAGKLMRENGVVLDQLKLTKSLLTMNQIGIISEHSRRSTADNM
TLAHSGSNKHRINNSQFKKNKDSKHEMPDDGFEIAACFLTTDLTKYCLNWRYQVIIP
FARTLNSMYGIPHLFEWIHLRLMRSTLYVGDPFNPPSDPTQLDLDTALNDDIFIVSP
RGGIEGLCQKLWTMISISTIILSATEANTRVMSMVQGDNQAIAITTRVVRSLSHSEK
KEQAYKASKLFFERLKANNHGIGHHLKEQETILSSDFFIYSKRVFYKGRILTQALKN
VSKMCLTADILGDCSQASCSNLATTVMRLTENGVEKDLCYFLNAFMTIRQLCYDLVF
PQTKSLSQDITNAYLNHPILISRLCLLPSQLGGLNFLSCSRLFNRNIGDPLVSAIAD
VKRLIKAGCLDIWVLYNILGRRPGKGKWSTLAADPYTLNIDYLVPSTTFLKKHAQYT
LMERSVNPMLRGVFSENAAEEEEELAQYLLDREVVMPRVAHVILAQSSCGRRKQIQG
YLDSTRTIIRYSLEVRPLSAKKLNTVIEYNLLYLSYNLEIIEKPNIVQPFLNAINVD
TCSIDIARSLRKLSWATLLNGRPIEGLETPDPIELVHGCLIIGSDECEHCSSGDDKF
TWFFLPKGIRLDNDPASNPPIRVPYIGSKTDERRVASMAYIKGASVSLKSALRLAGV
YIWAFGDTEESWQDAYELASTRVNLTLEQLQSLTPLPTSANLVHRLDDGTTQLKFTP
ASSYAFSSFVHISNDCQVLEIDDQVTDSNLIYQQVMITGLALIETWNNPPINFSVYE
TTLHLHTGSSCCIRPVESCVVNPPLLPVPFINVPQMNKFVYDPEPLSLLEMEKIEDI
AYQTRIGGLDQIPLLEKIPLLAHLTAKQMVNSITGLDEATSIVNDAVVQADYTSNWI
SECCYTYIDSVFVYSGWALLLELSYQMYYLRIQGIQGILDYVYMTLRRIPGMAITGI
SSTISHPRILRRCINLDVIAPINSPHIASLDYTKLSIDAVMWGTKQVLTNISQGIDY
EIVVPSESQLTLSDRVLNLVARKLSLLAIIWANYNYPPKVKGMSPEDKCQALTTHLL
QTVEYVEHIQIEKTNIRRMIIEPKLTAYPSNLFYLSRKLLNAIRDSEEGQFLIASYY
NSFGYLEPILMESKIFNLSSSESASLTEFDFILNLELSEASLEKYSLPSLLMTAENM
DNPFPQPPLHHVLRPLGLSSTSWYKTISVLNYISHMKISDGAHLYLAEGSGASMSLI
ETFLPGEVIWYNSLFNSGENPPQRNFAPLPTQFIESVPYRLIQAGIAAGSGVVQSFY
PLWNGNSDITDLSTKTSVEYIIHKVGADTCALVHVDLEGVPGSMNSMLERAQVHALL
ITVTVLKPGGLLILKASWEPFNRFSFLLTILWQFFSTIRILRSSYSDPNNHEVYIIA
TLAVDPTTSSFTTALNRARTLNEQGFSLIPPELVSEYWRRRVEQGQIIQDCIDKVIS
ECVRDQYLADNNIILQAGGTPSTRKWLDLPDYPSFNELQSEMARLITIHLKEVIEIL
KGQSSDHDTLLFTSYNVGPLGKINTILRLIVERILMYTVRNWCILPTQTRLTLRQSI
ELGEFRLRDVITPMEILKLSPNRKYLKSALNQSTFNHLMGETSDMLLNRSYQKRIWK
AIGCVIYCFGLLTPDVEDSERIDIDNDIPDYDIHGDII

FIG. 16 (CONT)

MUMPS VIRUS AS A POTENTIAL ONCOLYTIC AGENT

CROSS-REFERENCE TO RELATED APPLICATION

This application is a National Stage application under 35 U.S.C. § 371 of International Application No. PCT/US2016/036944, having an International Filing Date of Jun. 10, 2016, which claims the benefit of U.S. Provisional Application No. 62/175,099, filed Jun. 12, 2015. The disclosure of the prior applications are incorporated by reference in their entirety.

BACKGROUND

1. Technical Field

This document relates to methods and materials for virotherapy. For example, this document provides methods and materials for treating cancer using a recombinant mumps virus as an oncolytic agent.

2. Background Information

Advanced metastatic cancers are basically incurable from having developed into a heterogeneous population with multiple ways to override the normal growth controls. Therefore it is unlikely that therapeutic attack on a single molecular target will have much effect and therapeutics (e.g., chemotherapy combinations, radiotherapies) often select resistance from the tumors heterogeneous population.

SUMMARY

Mumps virotherapy is extremely safe with virulent Urabe strain virus. Mumps virus (MuV) has significant oncolytic activity against variety of human cancers. Mumps treatment induces significant anti-tumor immunity indicating that MuV can be a potential candidate for immune therapy.

As described herein, a recombinant MuV can infect human tumor cells and exhibit oncolytic efficacy both in in vitro and in vivo. This document describes isolates of a MuV having oncolytic activity. This document also provides methods of making and using the oncolytic mumps virus. For example, the document provides methods of treating cancer by administering a recombinant MuV.

In general, one aspect of this document features a MuV (e.g., a recombinant MuV). The recombinant MuV can have oncolytic anti-cancer activity. The recombinant MuV can be a replication competent MuV. The recombinant MuV can include a modification in an RNA polymerase large (L) subunit coding sequence (e.g., an A to C substitution at nucleotide 13328). The modified RNA polymerase large (L) subunit coding sequence can encode a modified RNA polymerase large (L) subunit protein (e.g., an RNA polymerase large (L) subunit protein having an N to H substitution at amino acid 1631).

In another aspect, this document features a method for treating a patient having cancer. The method can include, or consist essentially of, administering to the patient a recombinant MuV having oncolytic anti-cancer activity. The cancer can be a blood cancer (e.g., leukemia, lymphoma, or myeloma). The blood cancer can be myeloma. The cancer can be a carcinoma (e.g., prostate cancer, breast cancer, hepatocellular carcinoma, lung cancer, or colorectal carcinoma). The carcinoma can be colorectal carcinoma. The recombinant MuV can be a replication competent MuV. The recombinant MuV can include a modification in an RNA polymerase large (L) subunit coding sequence (e.g., an A to C substitution at nucleotide 13328). The modified RNA polymerase large (L) subunit coding sequence can encode a modified RNA polymerase large (L) subunit protein (e.g., an RNA polymerase large (L) subunit protein having an N to H substitution at amino acid 1631). The method also can include administering ruxolitinib.

In another aspect, this document features an expression construct comprising a nucleotide sequence encoding a recombinant MuV having oncolytic anti-cancer activity. The recombinant MuV can be a replication competent MuV. The recombinant MuV can include a modification in an RNA polymerase large (L) subunit coding sequence (e.g., an A to C substitution at nucleotide 13328). The modified RNA polymerase large (L) subunit coding sequence can encode a modified RNA polymerase large (L) subunit protein (e.g., an RNA polymerase large (L) subunit protein having an N to H substitution at amino acid 1631).

In another aspect, this document features a method for treating a patient having cancer. The method includes, or consists essentially of, administering to the patient an expression construct including a nucleotide sequence encoding a recombinant MuV having oncolytic anti-cancer activity. The cancer can be a blood cancer (e.g., leukemia, lymphoma, or myeloma). The blood cancer can be myeloma. The cancer can be a carcinoma (e.g., prostate cancer, breast cancer, hepatocellular carcinoma, lung cancer, or colorectal carcinoma). The carcinoma can be colorectal carcinoma. The recombinant MuV can be a replication competent MuV. The recombinant MuV can include a modification in an RNA polymerase large (L) subunit coding sequence (e.g., an A to C substitution at nucleotide 13328). The modified RNA polymerase large (L) subunit coding sequence can encode a modified RNA polymerase large (L) subunit protein (e.g., an RNA polymerase large (L) subunit protein having an N to H substitution at amino acid 1631). The method also can include administering ruxolitinib.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Figures 5A, 5B:
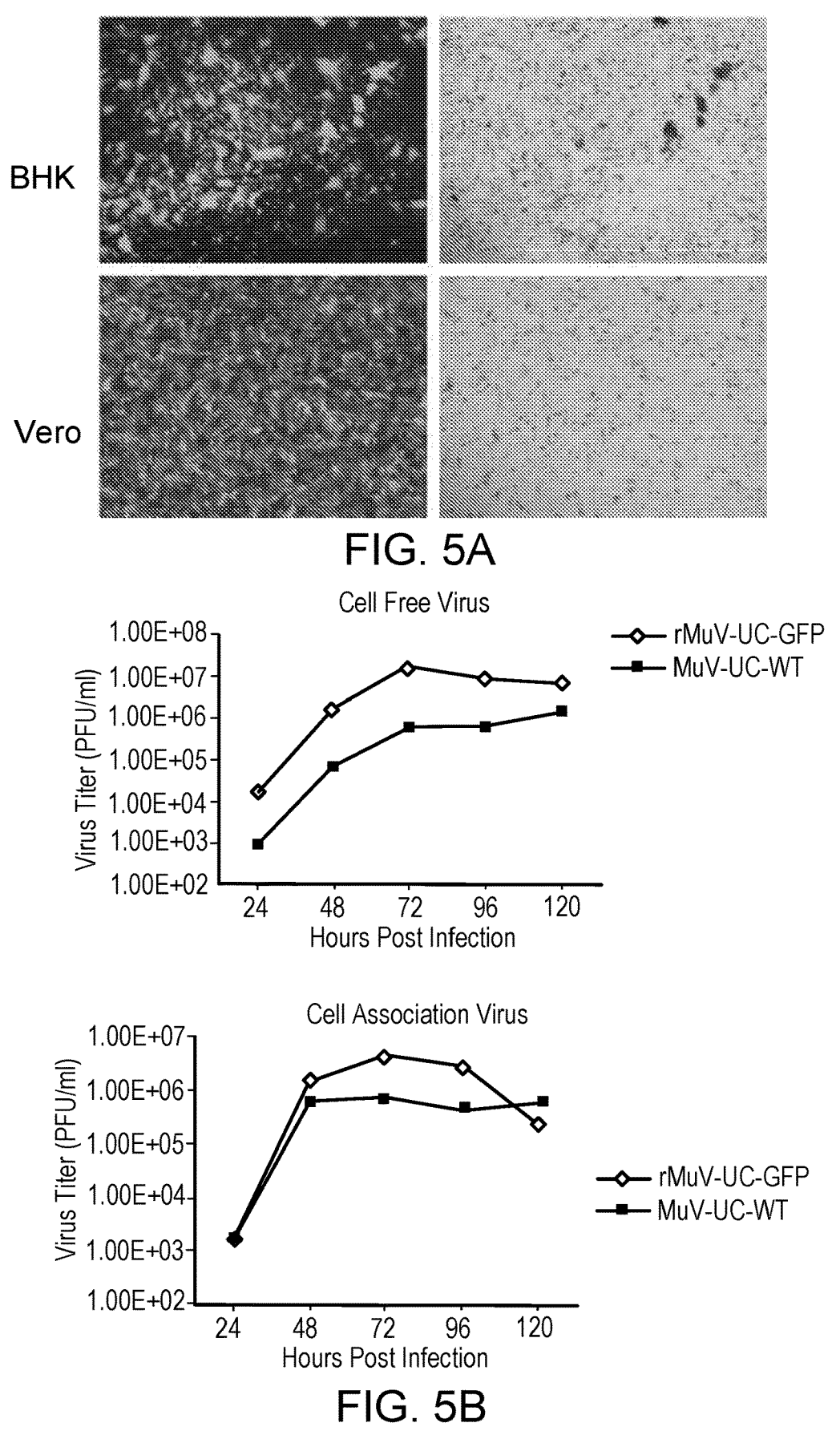

FIGS. 5A-5B show rescue of recombinant mumps viruses Urabe strain (rMuV-UC). A. Rescue of rMuV-UC-GFP infectious virus in BHK cells and further propagation of the same virus in Vero cells visualized by fluorescent microscopy. B. Mumps virus wild-type and rescued virus rMuV6 UC-GFP were compared for their growth potential in Vero cell in multi-step growth curve. Cells were infected with MOI of 0.1, supernatants and cell pellets were collected at different time intervals and titered in vero cells using standard plaque assay. Left panel shows virus titer of cell free supernatants and right panel shows virus titer of cell associated virus.

Figures 6B, 6C:
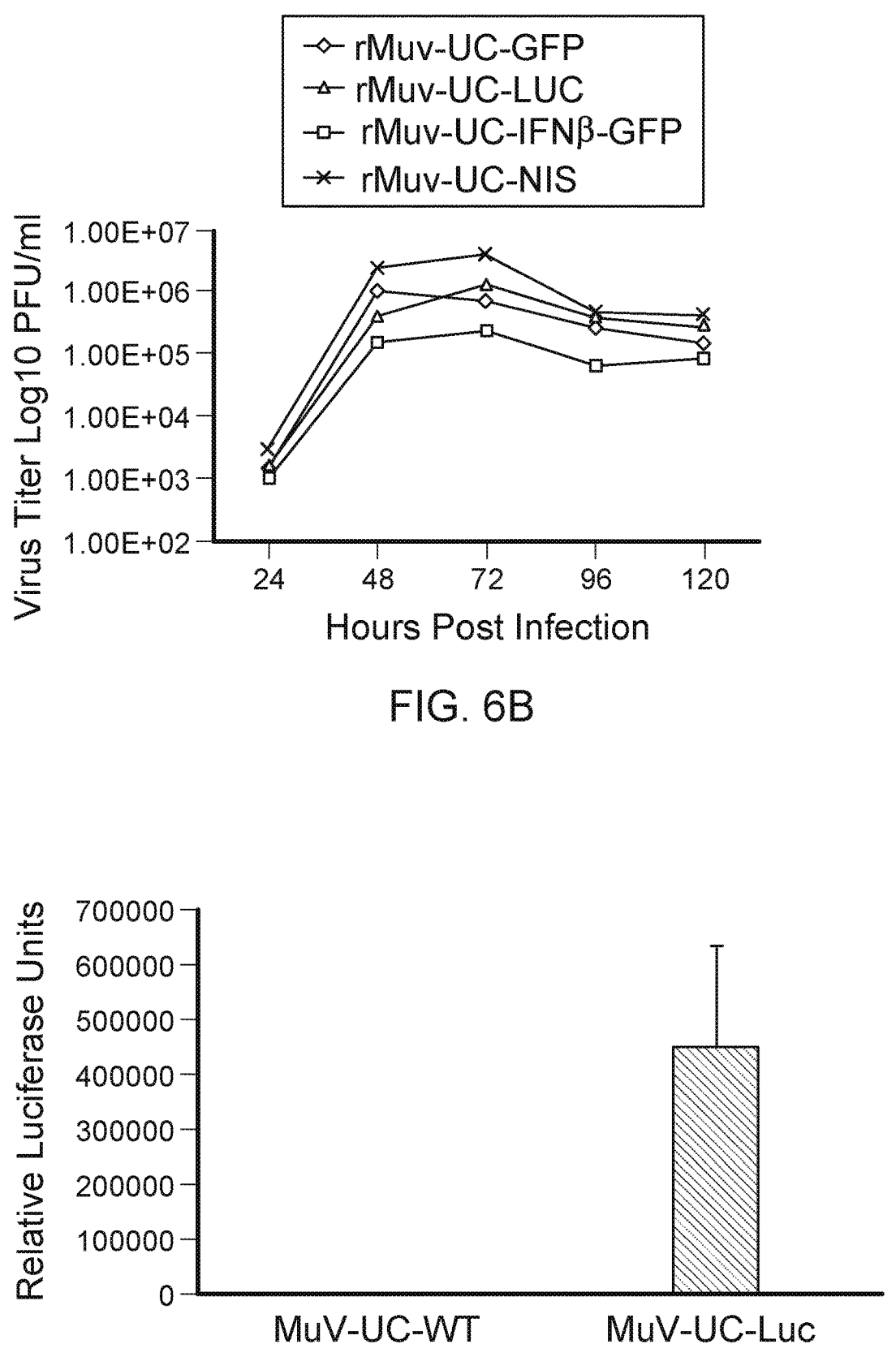

FIGS. 6A-6E show characterization of the replication and transgene expression of the recombinant mumps viruses. A. Schematic diagram of various constructs of mumps virus expressing foreign genes. B. Growth curve of various recombinant mumps viruses in Vero cells after infection at M.O.I. 0.1. C. Luciferase assay demonstrating the expression of LUC transgene by the rMuV14 UC-LUC in infected cells compared to only background LUC expression by the original MuV15 UC virus isolate. D. Measurement and comparison of activity of NIS produced by rMuV-UC16 NIS and wild-type MuV-UC-wt. E. Measurement of secreted mIFN-β in the supernatant of rMuV-UC-mIFNβ and MuV-UC infected vero cells by ELISA.

FIGS. 7A-7C show rMuV-UC-GFP replication in tumor cell lines. A.

Human cancer cell lines were infected with mumps virus at MOI of 10 and images were taken 5 days of post-infection. B. Mouse cancer cell lines were infected with mumps virus at MOI of 10 and images were taken 5 days post-infection. C. Selected cell lines were infected with MOI of 1.0 and supernatants were collected at indicated time points and titered in vero cells.

FIG. 8 shows a comparison of mumps viruses for the efficacy and growth potential in selected cell lines. (A-C) CT-26-LacZ, N2A and Kas 6/1 cell lines were infected with MuV-UC-WT, MuV-UC-GFP and MuV-UC-L13328 at indicated MOI. Cell viability was measured on day 7 by MTS Cell Proliferation Assay. (D) Vero cells were infected with MOI of 0.1, supernatants were collected at different time intervals and titered in vero cells using standard plaque assay.

FIGS. 9A-9C show infectivity of rMuV-UC-GFP in rat cancer cells. A. Rat glioma cells C6 and RG2 were infected at MOI 0.1 and compared with Vero cells. The fluorescent images were taken at indicated time points. B. Vero, RG2 and C6 cells were infected with mumps virus at 0.1 MOI. Supernatants were collected at indicated time points and were titered in Vero cells. C. Cell viability assay for C6 and RG2 cells infected with mumps virus.

FIG. 10 shows the effect of a Janus kinase inhibitor on mumps virus infectivity. Selected tumor cells lines were treated with Ruxolitinib, a Janus kinase inhibitor, at the indicated doses. After 48 hours the treated and control cells were infected with rMuV-UC-GFP mumps virus (M.O.I. 10). Fluorescent images were taken 5 days post-infection.

FIGS. 11A-11F show oncolytic efficacy of mumps viruses in the mouse CT-26-LacZ colon carcinoma tumor model. Balb/c mice (n=5) were implanted with $5\times10^6$ CT-26-LacZ cells subcutaneously. Once the tumor volume reached 0.2 to 0.5 $mm^3$, mice were treated with saline or mumps viruses ($10^6$–$10^7$ PFU) administered intravenously through by tail vein: (A) MuV-UC-wt ($10^7$), (B) rMuV-UC-GFP-$10^6$; (C) rMuV-UC-GFP-$10^7$; (D) rMuV-UC-Luc ($10^7$); or (E) saline. Tumor size was measured using handheld calipers three times a week. (F) Kaplan-Meier survival curves for the mice are shown in the survival curve. *, P=0.0072 rMuV-UC-wt vs Saline; P=0.1316 rMuV-UC-Luc vs Saline.

FIGS. 12A-12D show in vitro oncolytic efficacy of MuV-UC-GFP. Panel of mouse and human cancer cell lines were infected with indicated MOI of MuV-UC-GFP. Cell viability was measured on day 7 by MTS Cell Proliferation Assay.

FIGS. 13A-13E show oncolytic efficacy of mumps virus in the mouse N2A neuroblastoma tumor model. A/J mice (4 weeks old, n=7) bearing subcutaneous N2A tumors were treated with a single dose ($1\times10^7$) administered intravenously through by tail vein: (A) MuV-UC-wt; (B) rMuV-UV-L13328-GFP; (C) rMuV-UC-LUC; (D) or saline. Tumor size was measured using handheld calipers three times a week. (E) Kaplan-Meier survival curves for the mice are shown in the survival curve.

FIGS. 14A-14E show oncolytic efficacy of mumps viruses infection in human myeloma model. NCr nude mice (4 weeks old; n=5) bearing subcutaneous Kas6/1 myeloma tumors were treated with a single intravenous dose ($1\times10^7$ pfu) of (A) MuV-UC-wt; (B) rMuV-UC-LUC; or (C) rMuV21 UC-L13328-GFP; (D) control saline. Tumor size was measured by serial caliper measurements. (E) Kaplan-Meier survival curves for the mice are shown in the survival curve.

FIG. 15 shows immunohistochemical staining of Kas6/1 tumors. Kas6/1 tumors were harvested at 7 day and 12 day post-treatment, sectioned and immunohistochemistry (IHC) staining was carried out using mumps polyclonal antibodies; mumps virus antigen (red) and cell nuclei (Hoechst/blue). Magnification, 40×.

FIG. 16 shows the Urabe mumps virus sequence (SEQ ID NO:1) encoding the NP protein (SEQ ID NO:2), the P protein (SEQ ID NO:3), the V protein (SEQ ID NO:4), the I protein (SEQ ID NO:5), the M protein (SEQ ID NO:6), the F protein (SEQ ID NO:7), the SH protein (SEQ ID NO:8), the HN protein (SEQ ID NO:9), the L protein (SEQ ID NO:10). See, NCBI Accession No: AF314558.

DETAILED DESCRIPTION

This document provides methods and materials for treating cancer. For example, this document provides methods and materials for using a MuV to treat cancer. In some cases, a MuV can be used to reduce the number of cancer cells.

An oncolytic virus is a virus that preferentially infects and kills cancer cells. Oncolytic viruses are thought not only to cause direct destruction of cancer cells, but also to stimulate host anti-cancer immune responses.

Oncolytic virotherapy is an emerging cancer treatment that seeks to use viruses that have evolved to exploit some of the same pathways that cancer cells activate during malignant progression to kill these cells. In addition, in a second arm of attack, the combination of cancer cell destruction by viruses may trigger a unique immune response from the combination of virus induced danger signals and the heterogeneous antigenic variation of the cancer cells. A wide variety of viruses from very different virus families are currently being explored as cancer therapeutics. As with chemotherapies and radiotherapies, we can expect that each oncolytic virus may have an optimal therapeutic effect only on certain cancer types. Treating patients with combinations of oncolytic viruses as well as in combination with chemotherapies and radiotherapies will offer therapeutics with vastly different modes of action that will work together to reduce tumor cell escape.

This disclosure provides a MuV (e.g., an Urabe strain MuV) having oncolytic anti-cancer activity. A MuV provided herein can be a recombinant MuV. A MuV provided herein can be a MuV isolate. In some cases, a MuV provided herein can be a replication competent MuV. A MuV provided herein can include one or more modifications from a wild type MuV. In some cases, a MuV provided herein can include one or more modifications from the Urabe strain of MuV. An Urabe strain of MuV can have a sequence set forth in, for example, National Center for Biotechnology Information (NCBI) Accession No: AF314558 (see, e.g., Version AF314558.1; GI:14325886). A MuV provided herein can include one or more modifications in a non-coding region of a MuV and/or one or more modifications in any MuV coding sequence. A MuV provided herein can include one or more modifications in an encoded protein. Examples of MuV proteins include, for example, nucleocapsid proteins (NP), matrix (M) proteins, fusion (F) proteins, hemagglutinin-neuraminidase (HN) proteins, large (L) subunit protein of the RNA polymerase, or phosphoprotein (P) subunit of the RNA polymerase). A MuV provided herein can include one or more modifications in the large (L) subunit protein of the RNA polymerase. For example, a MuV provided herein can include a substitution (e.g., an A to C substitution) at nucleotide 13328 (nt13328) of the L coding sequence resulting in an N to H substitution at amino acid 1631 in the L subunit protein of the RNA polymerase. Modifications can include any of a variety of changes, and include changes to the genome of the virus. Exemplary nucleic acid modifications include substitutions, truncations, insertions, and deletions. In some cases, a MuV can be modified by one or more substitutions relative to the wild type Urabe strain of MuV. Exemplary modifications include, for example, the nucleotide substitutions and resulting amino acid changes set forth in Tables 1-2. Modifications shown in Tables 1-2 are relative to the Urabe mumps virus sequence in NCBI Accession No: AF314558.

TABLE 1

Figure 1:
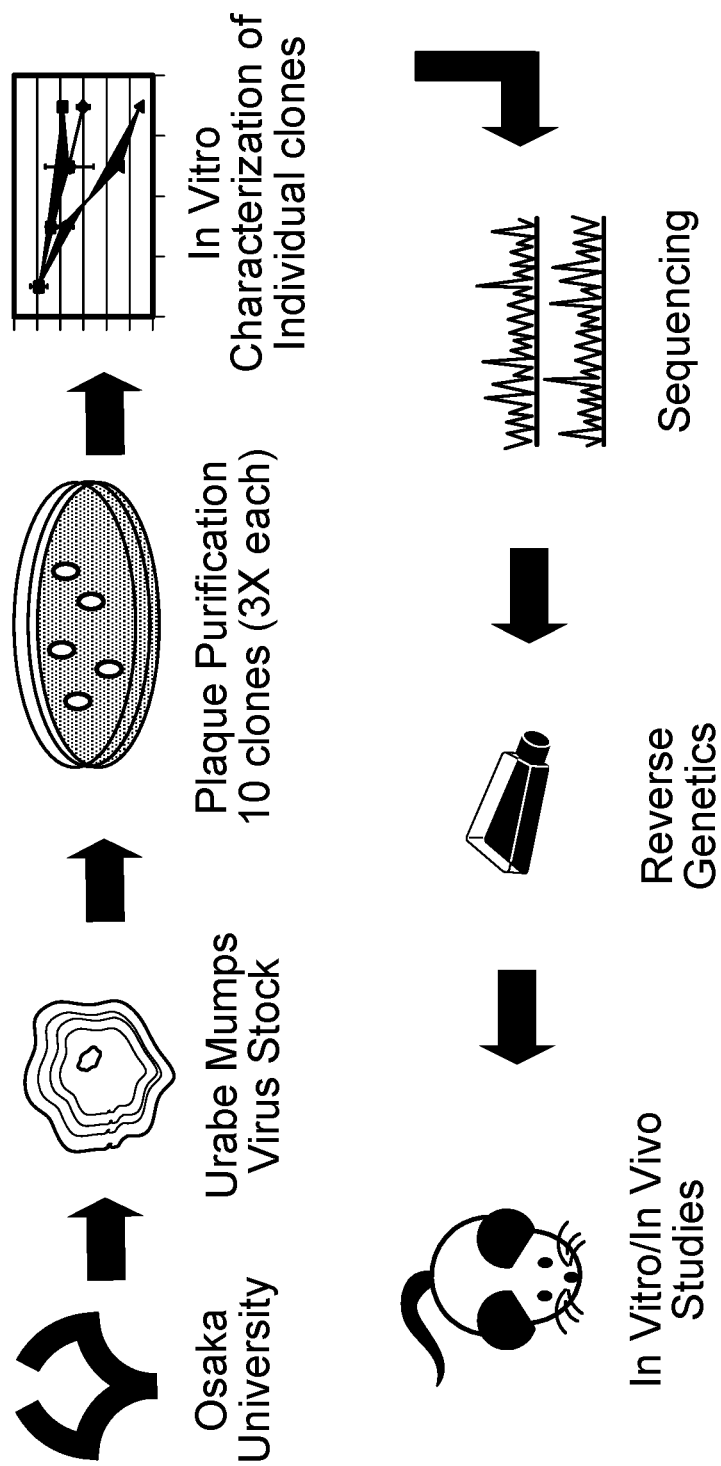
FIG. 1 is a schematic showing the procedure used to identify MuV isolates from the original mumps virus, and the generated recombinant MuV.
Figure 2:
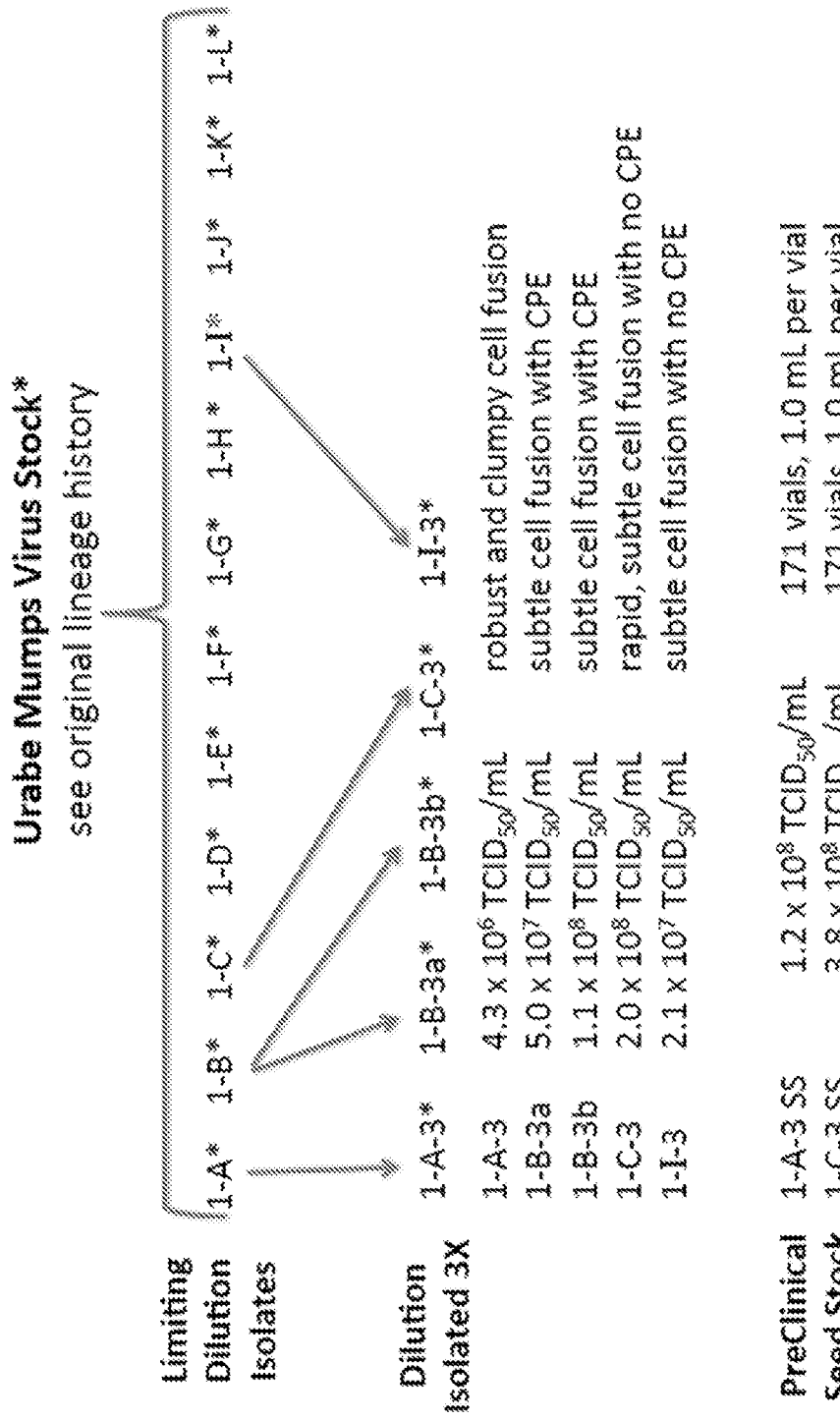
FIG. 2 shows MuV isolates in the tcMuV-U stock.
Figure 3:
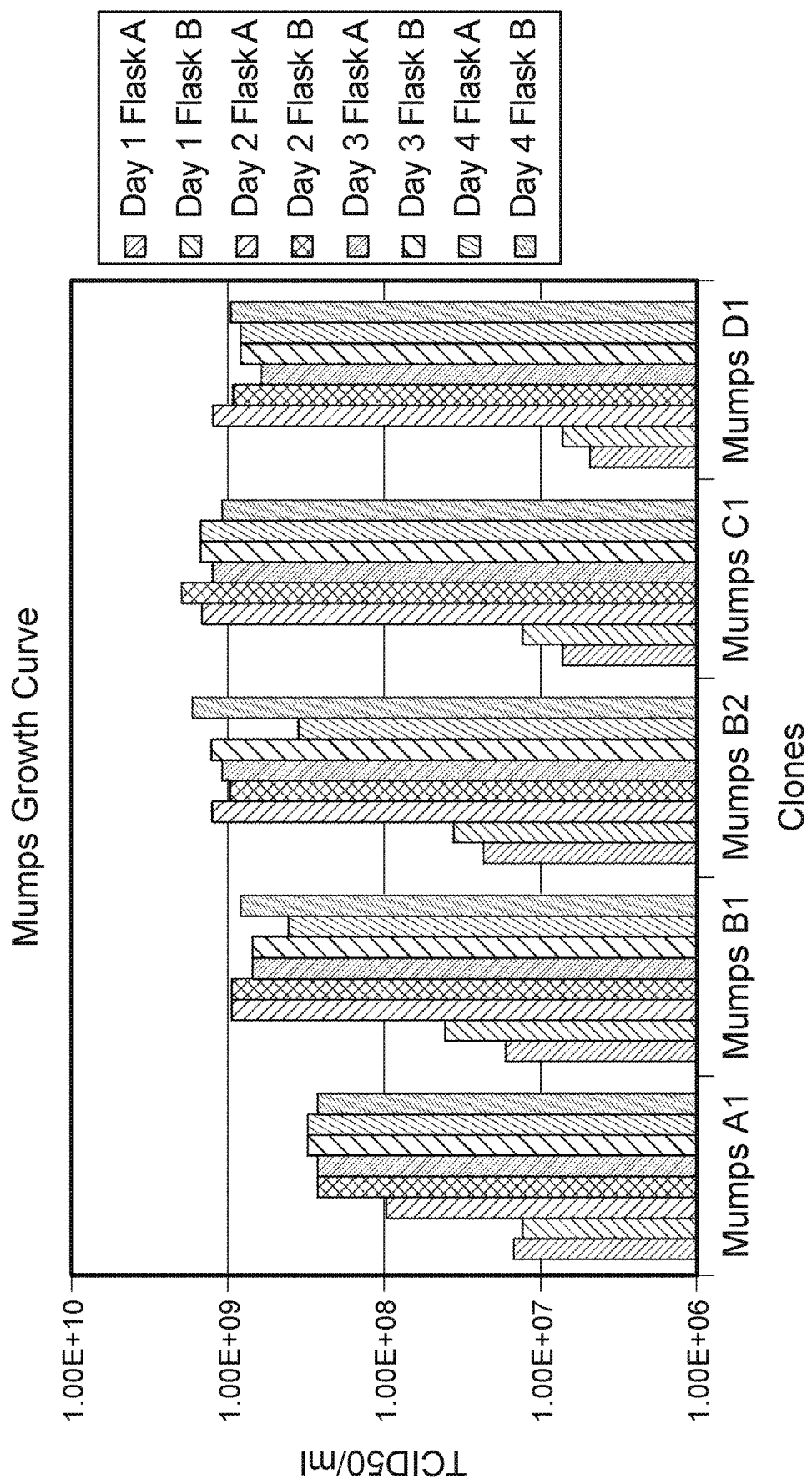
FIG. 3 shows safety of MuV virotherapy.
Figure 4:
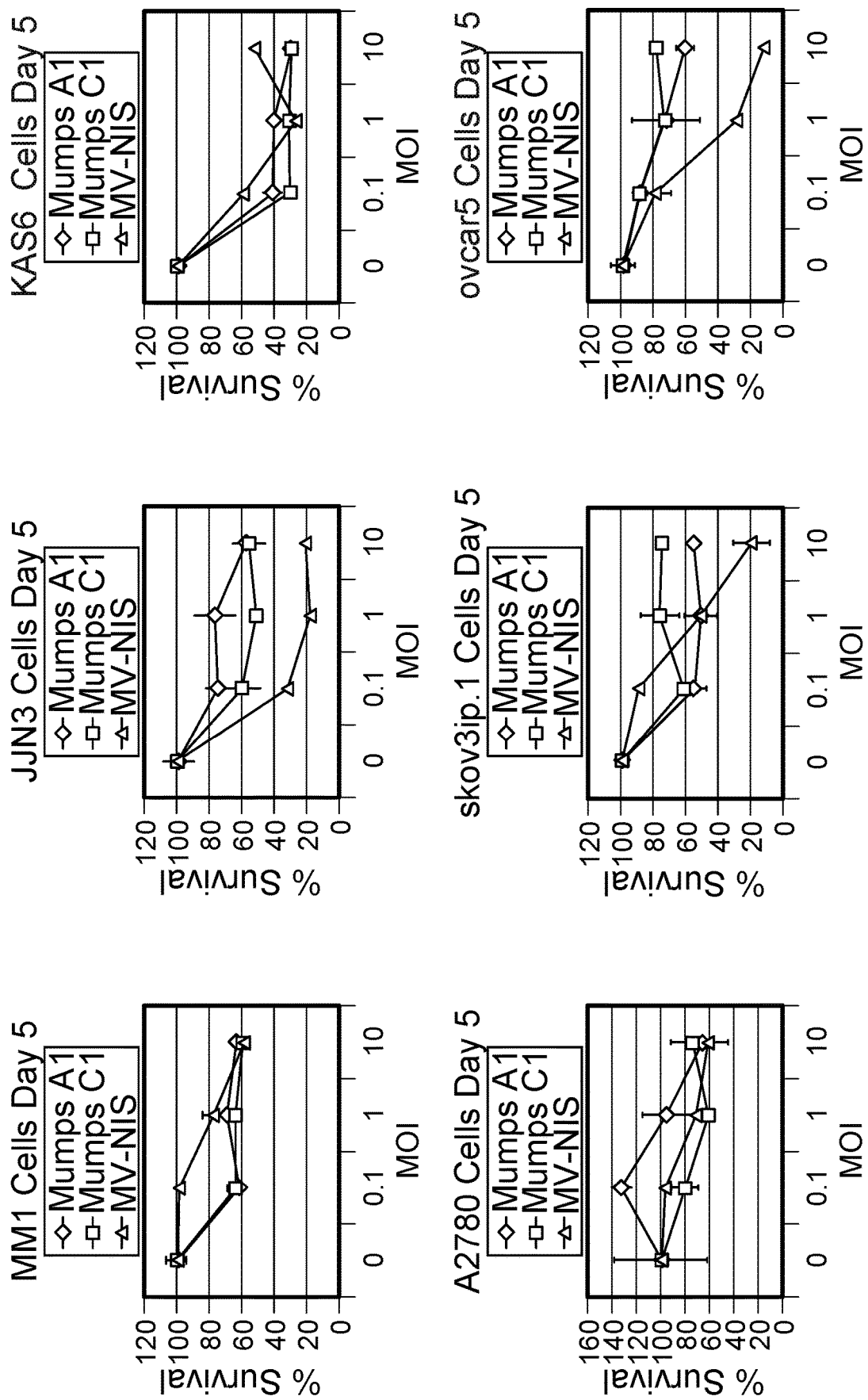
FIG. 4 shows oncolytic activity of MuV in human cancers.
Figure 4:
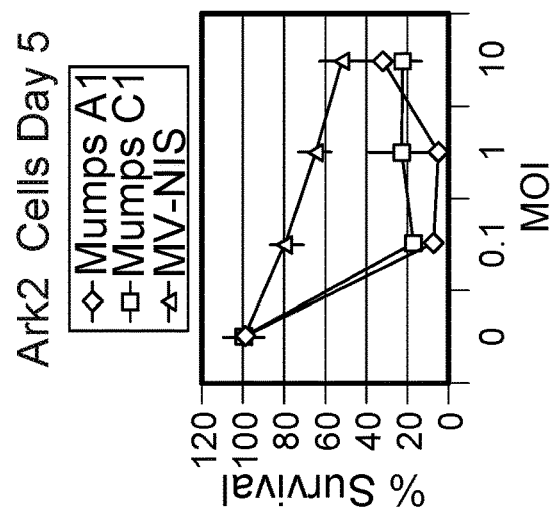
Figure 4:
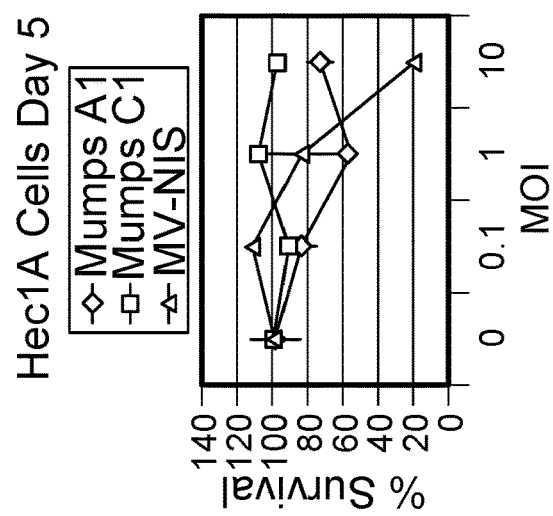
Figure 4:
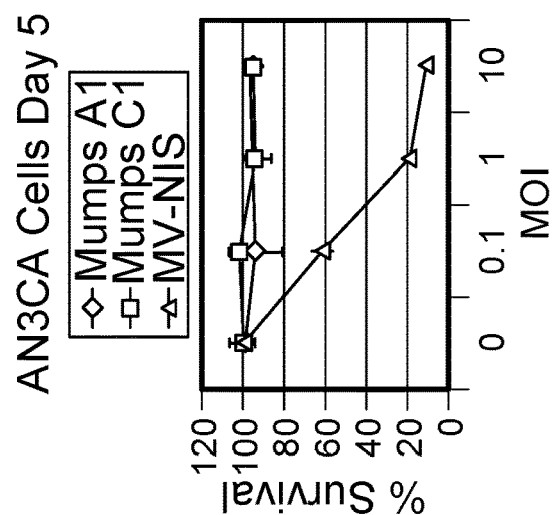
Figure 6A:
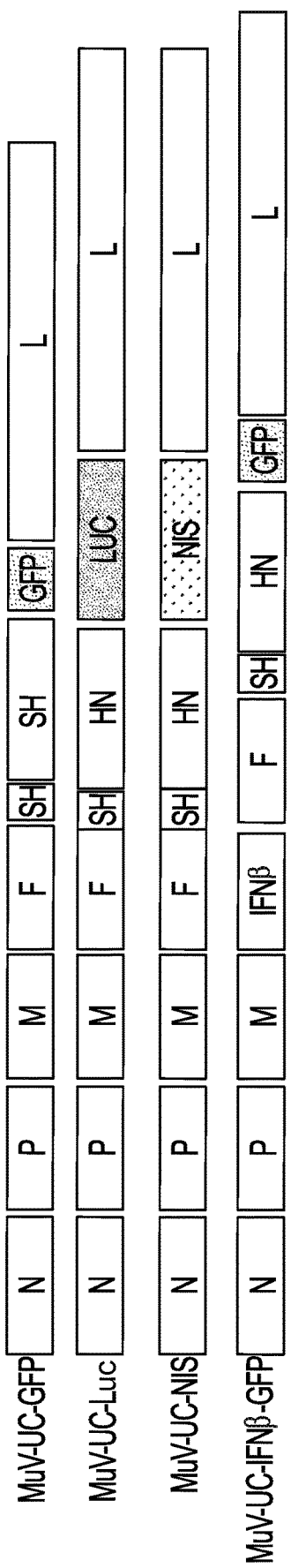
Figure 6D:
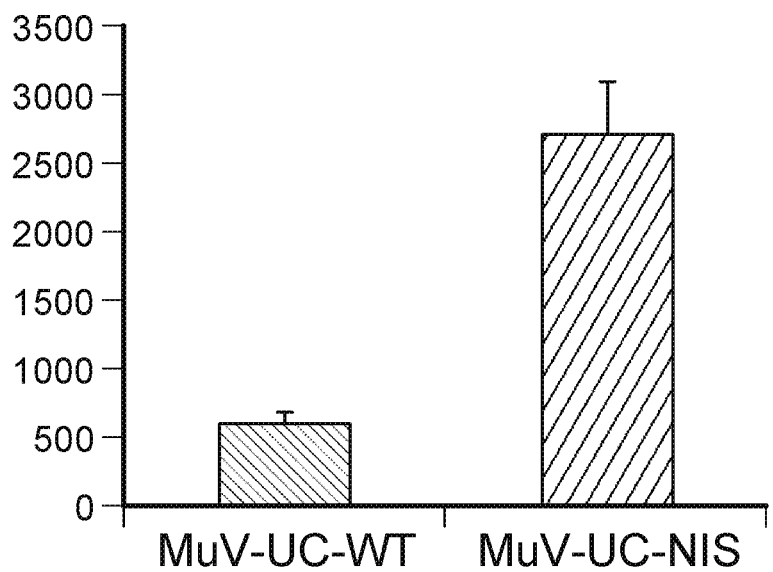
Figure 6E:
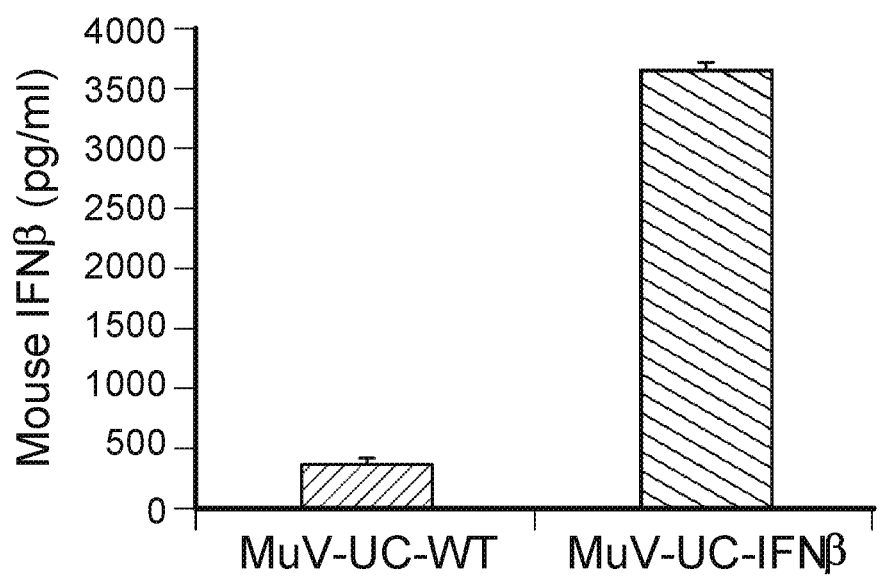
Figure 8:
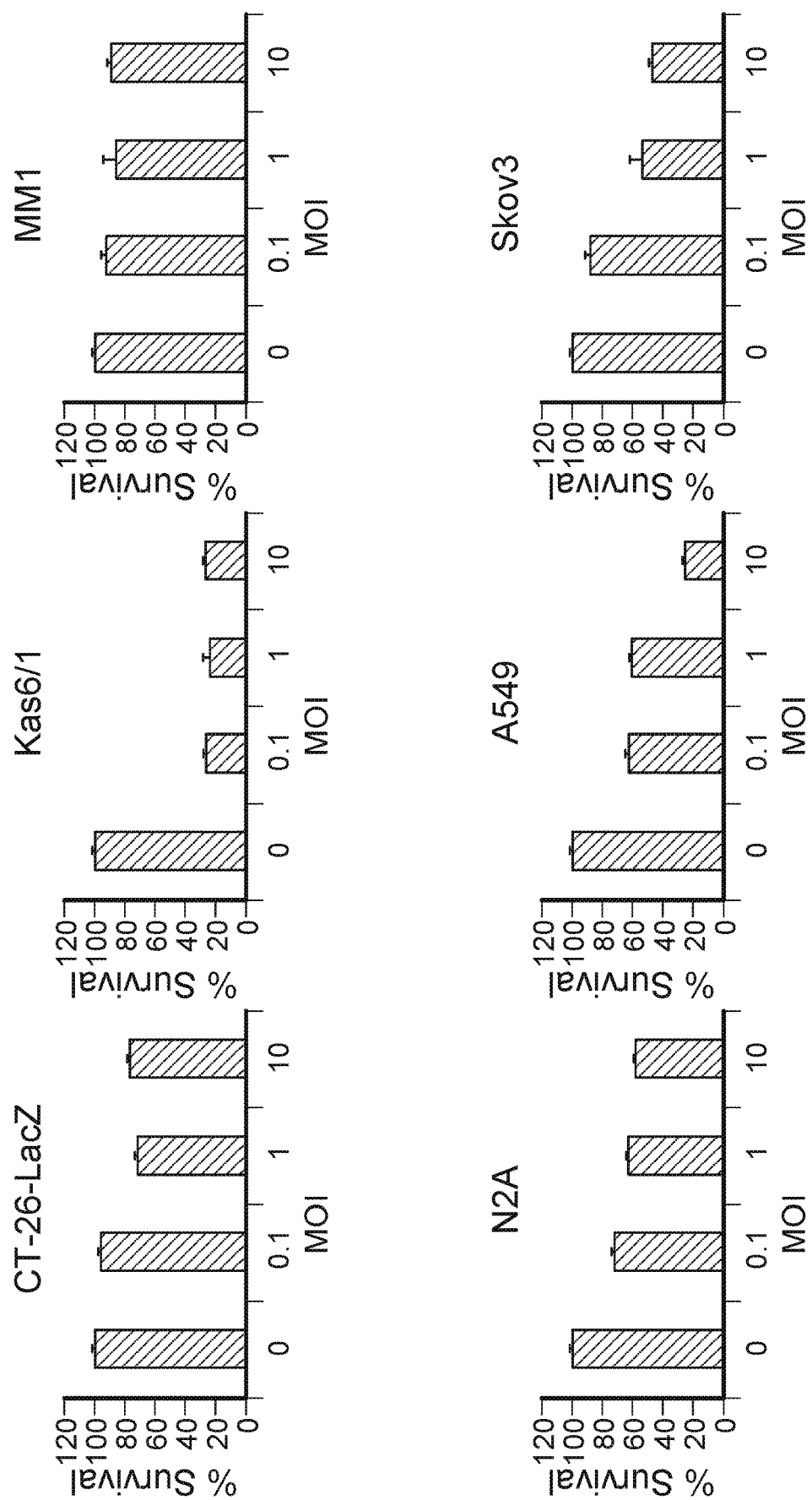
Figure 8:
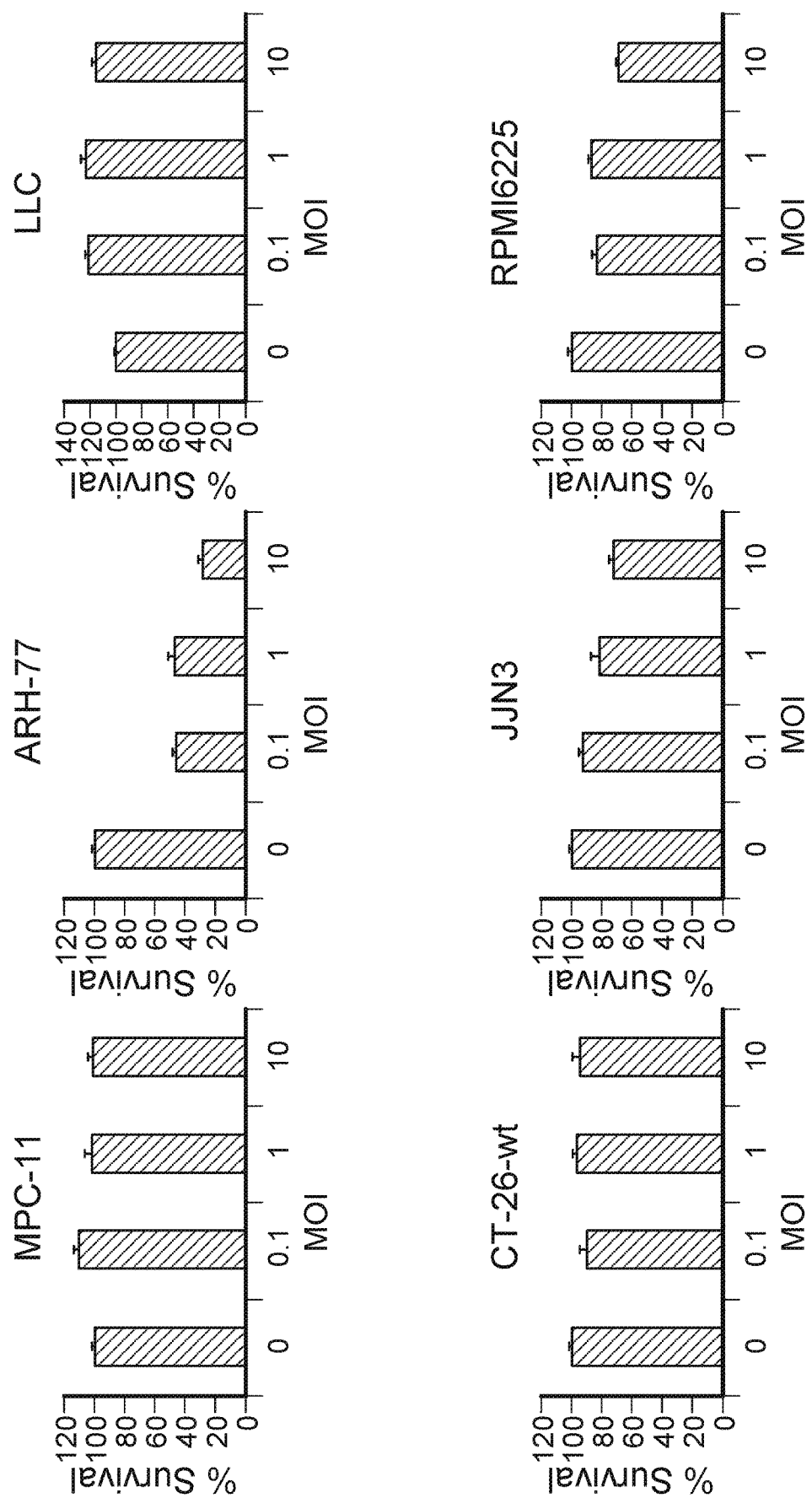
Figure 10:
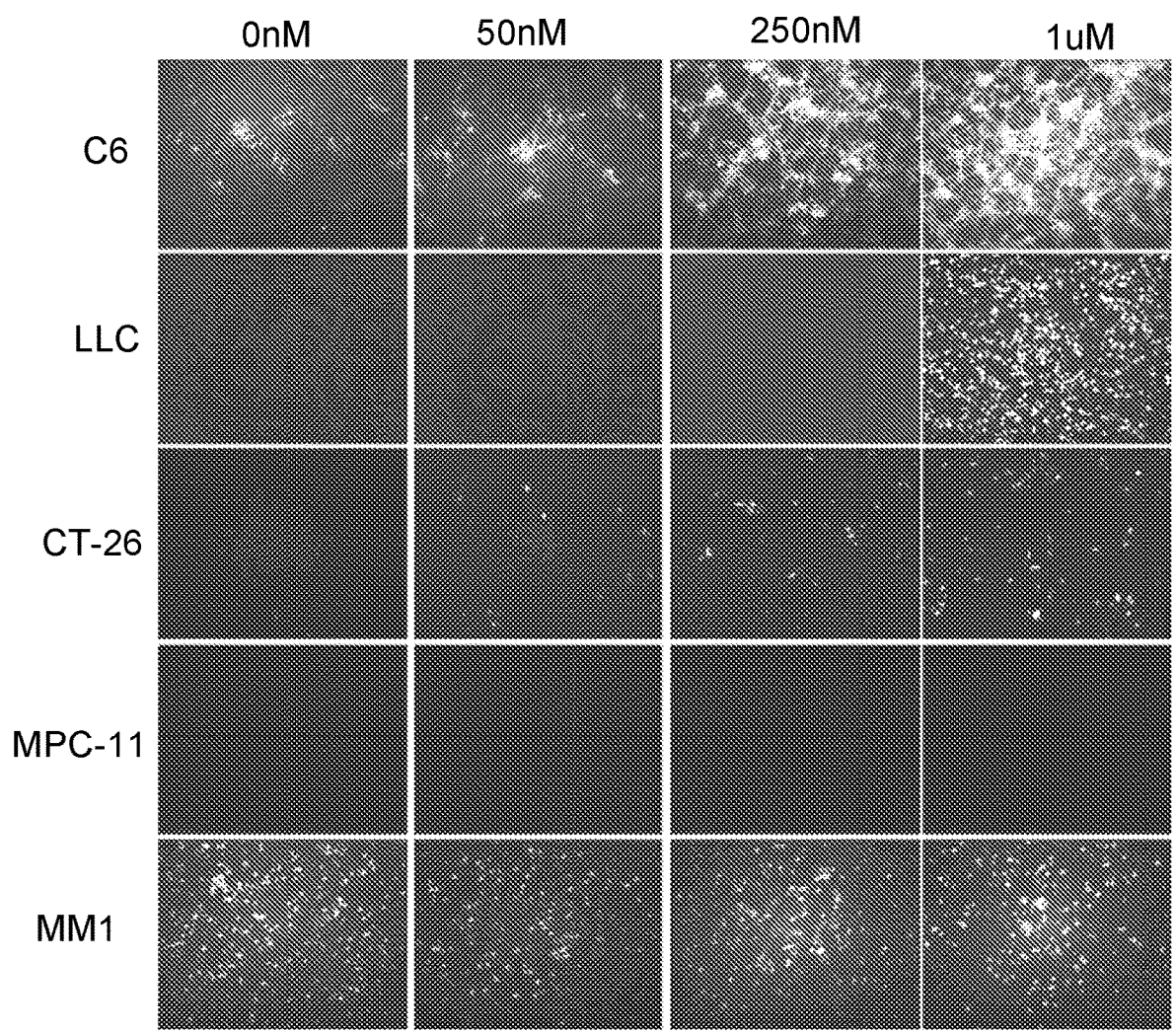
Figure 11A:
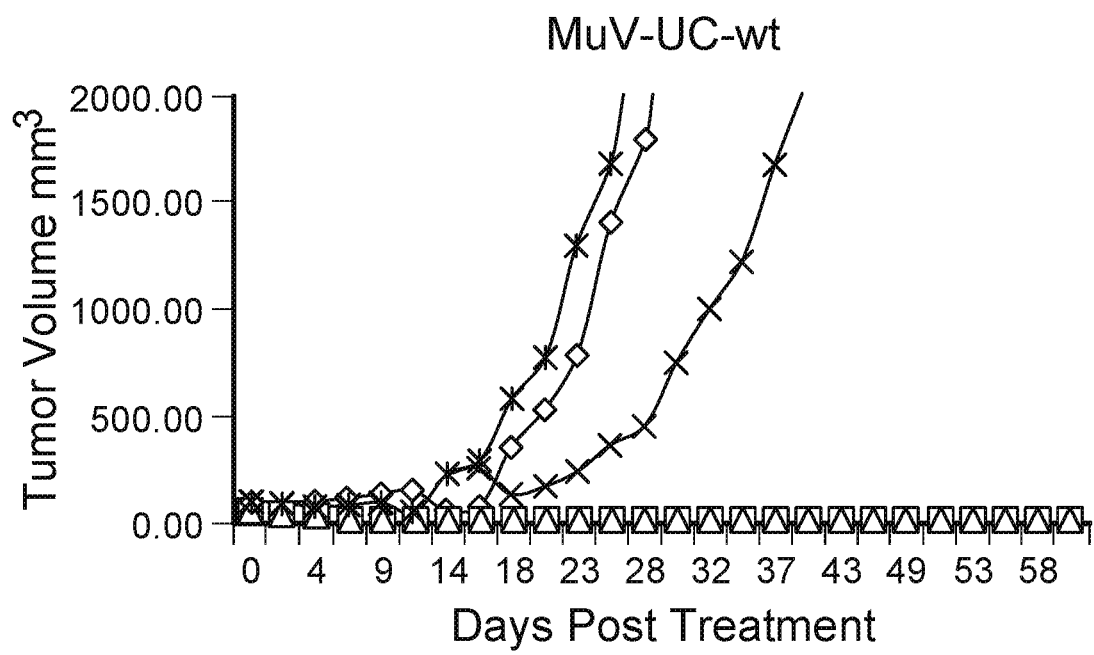
Figure 11B:
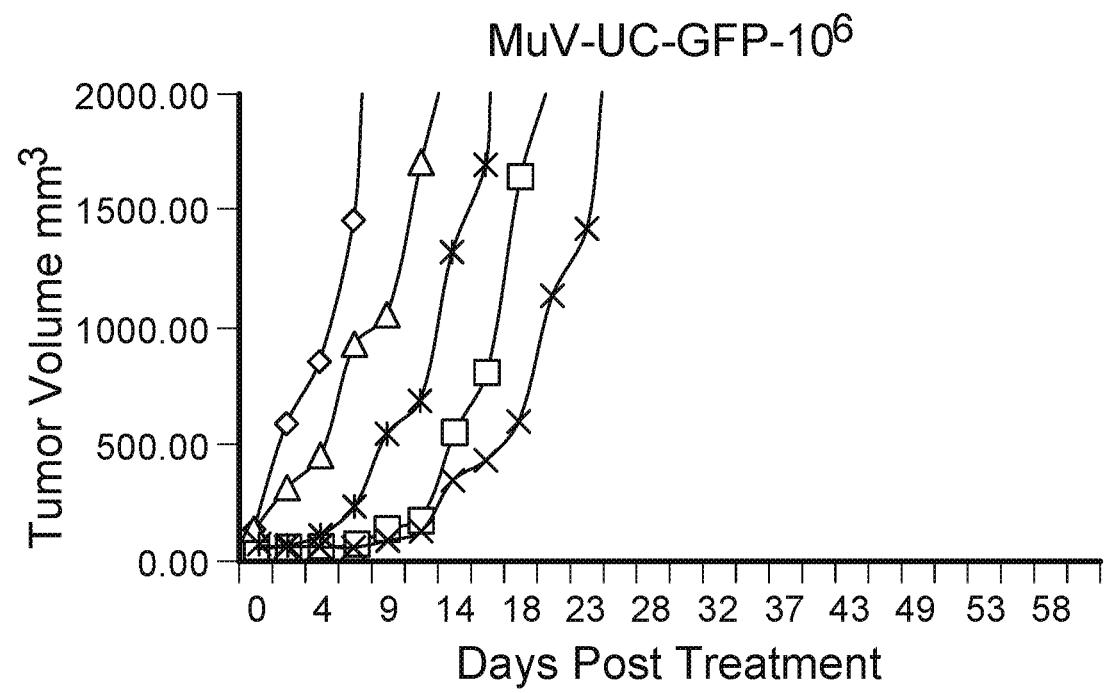
Figure 11C:
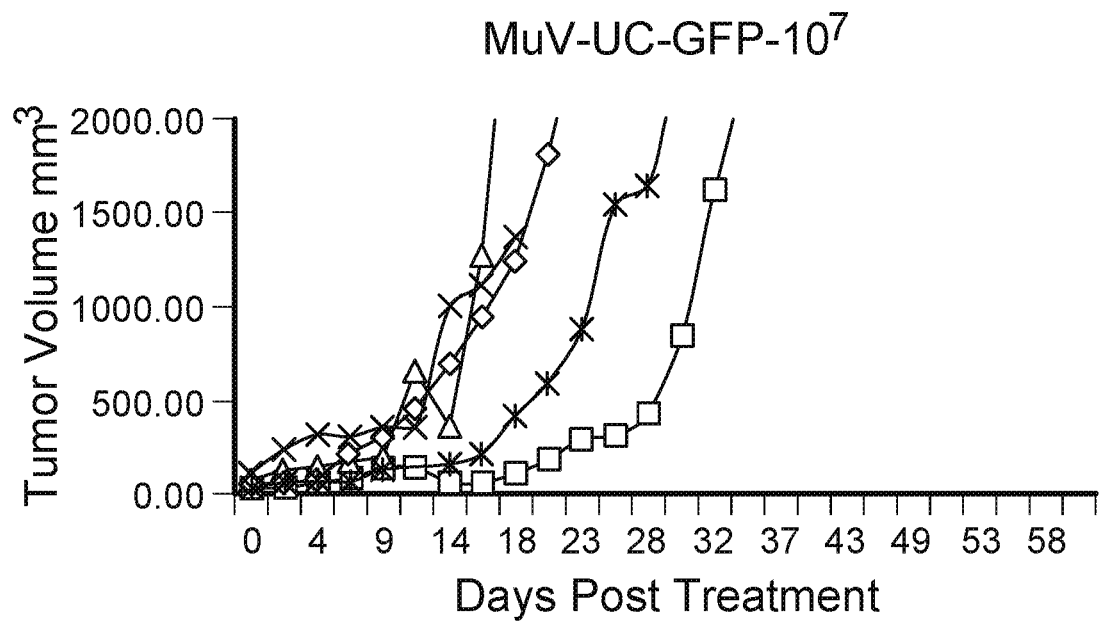
Figure 11D:
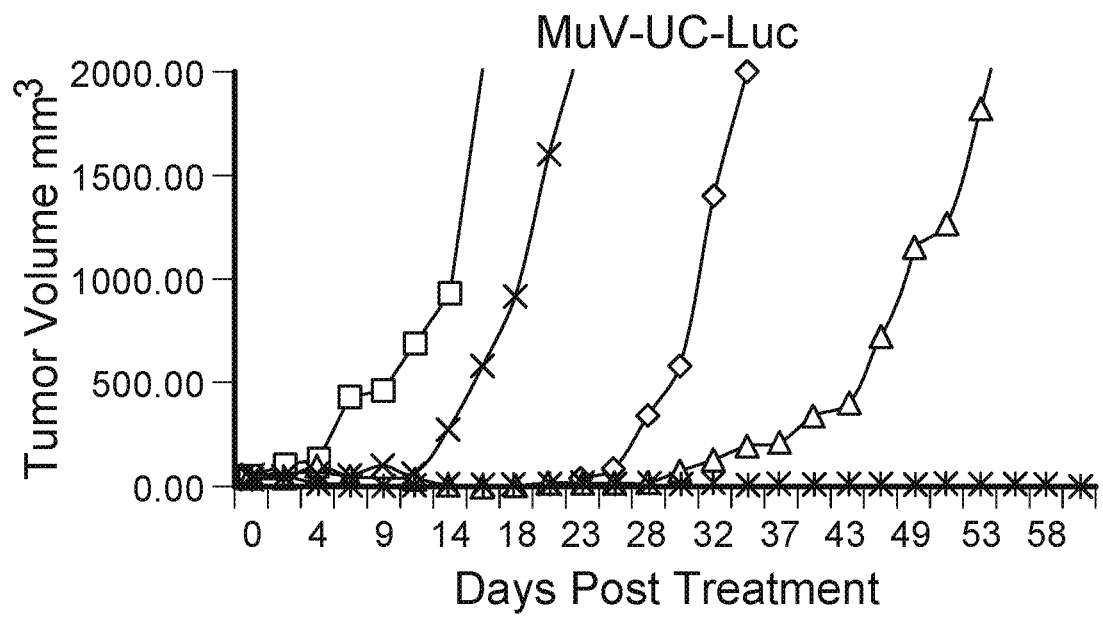
Figure 11E:
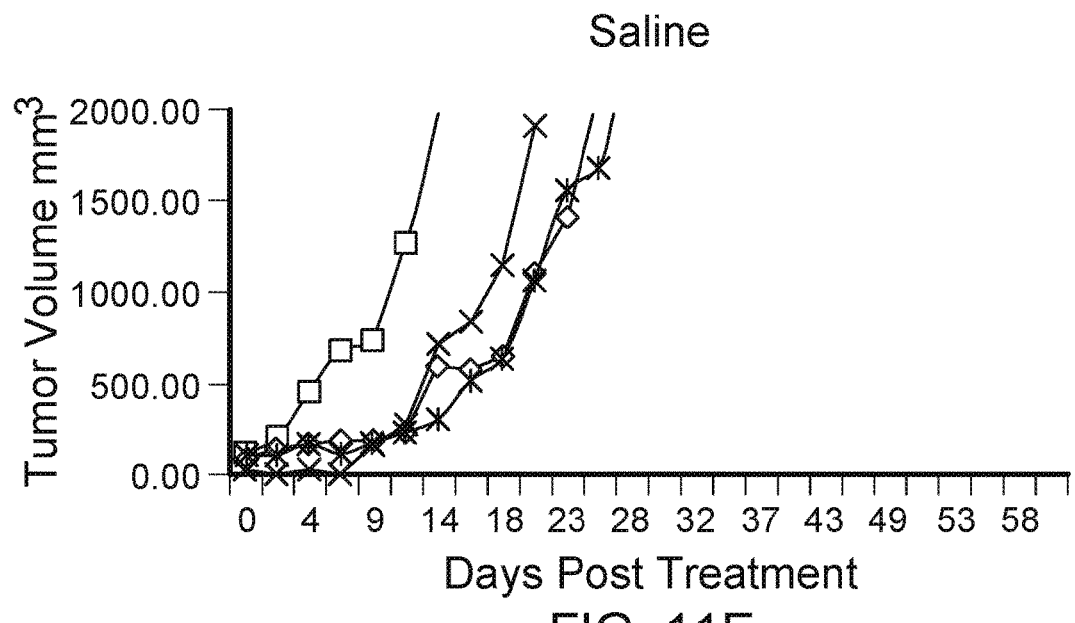
Figure 11F:
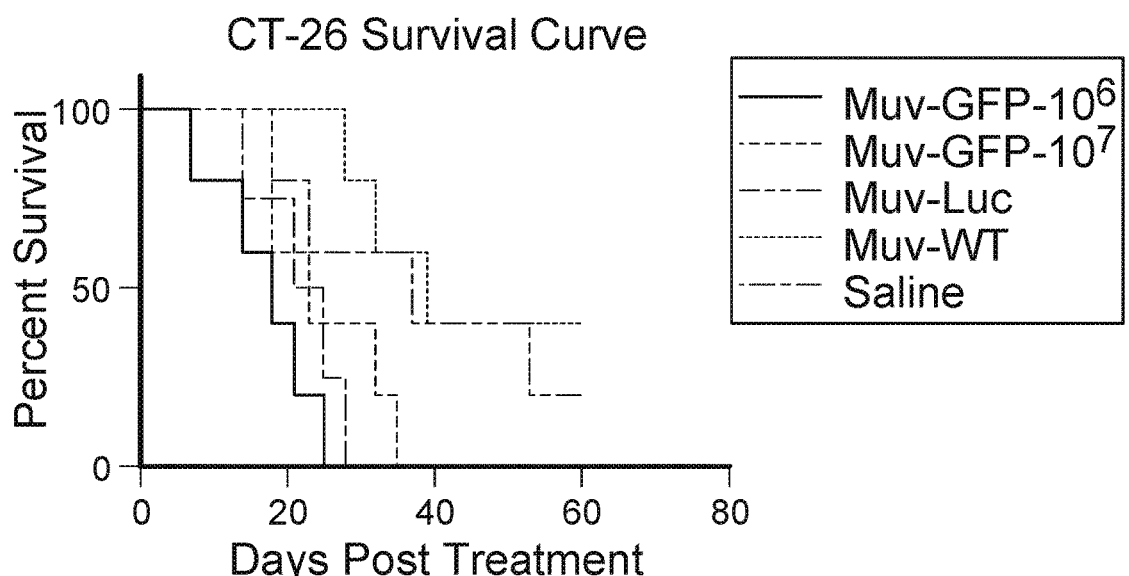
Figure 12A:
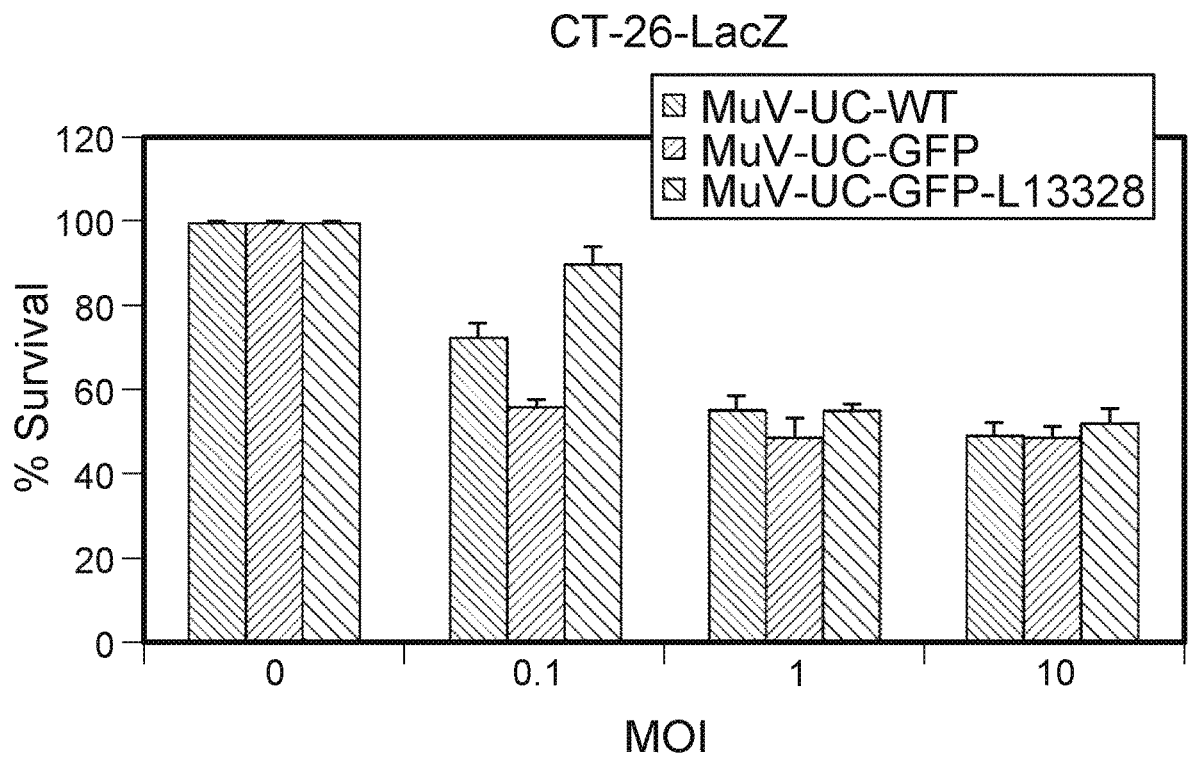
Figure 12B:
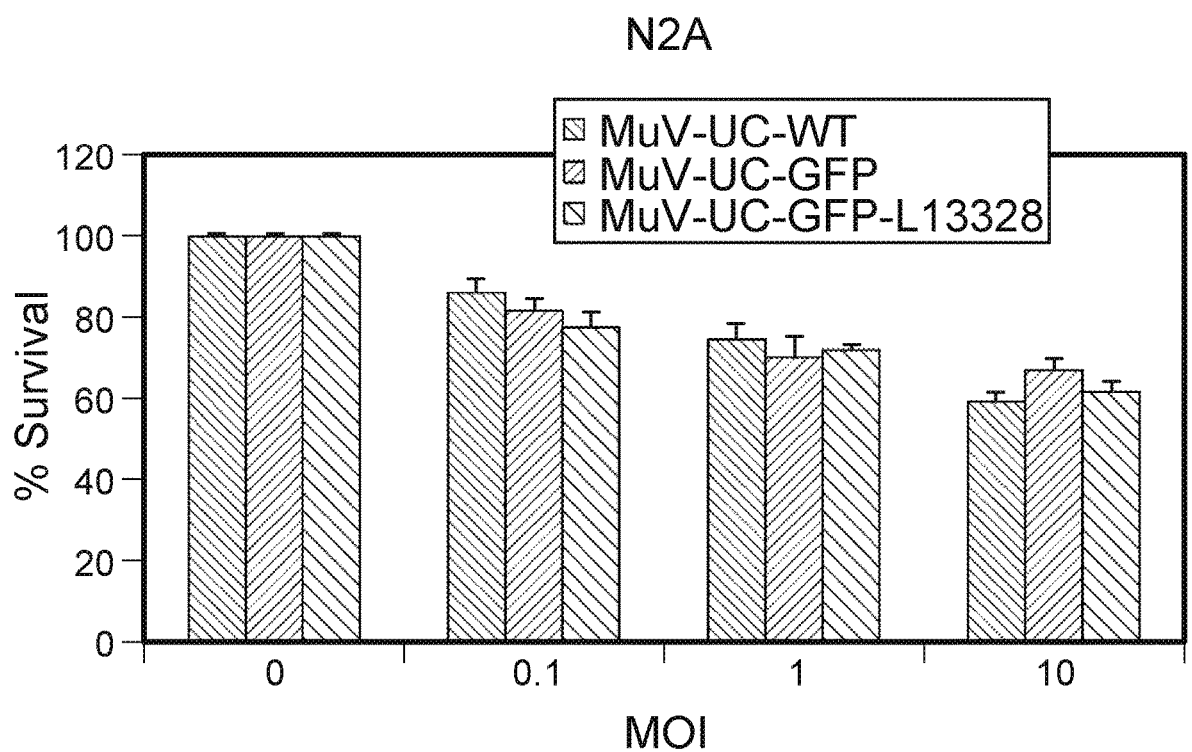
Figure 12C:
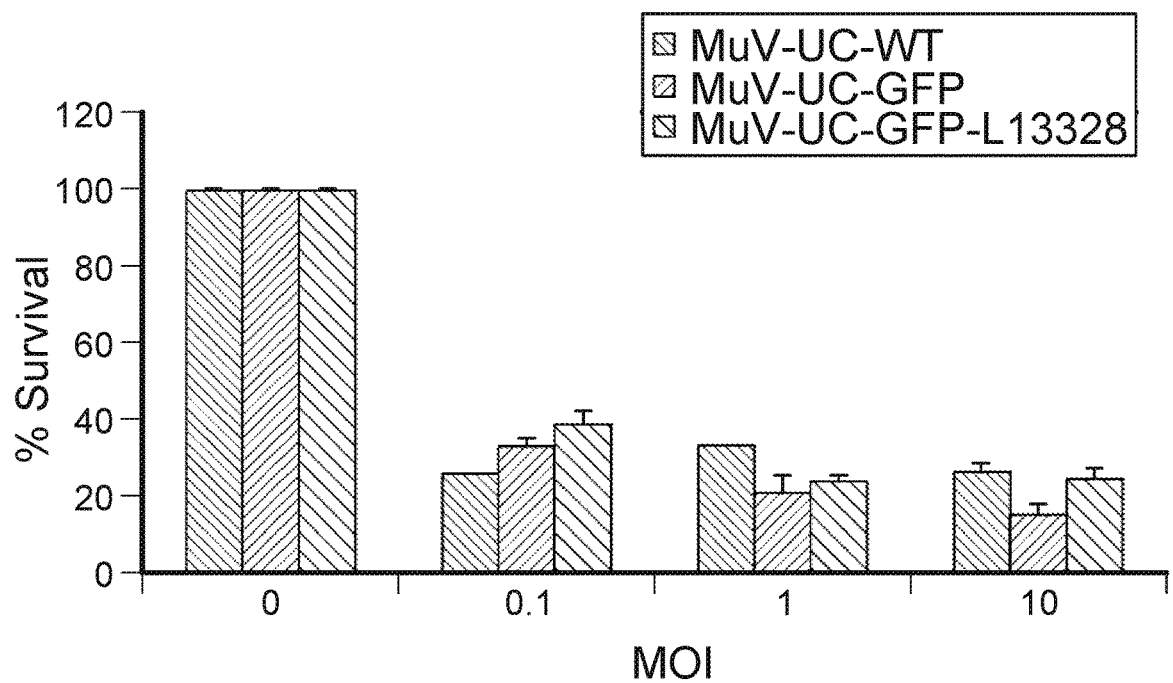
Figure 12D:
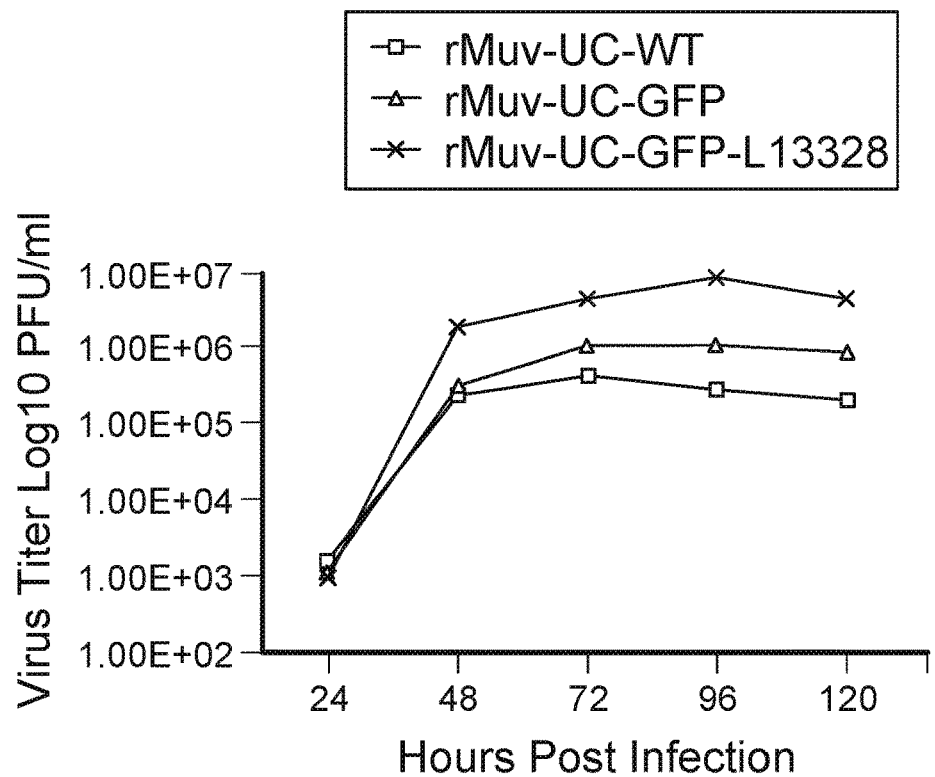

Nucleotide sequences of each virus stock.

| Gene | Base | Nucleotide Change | Amino Acid Change | Origin Japan | Isolate 1-A | Isolate 1-B | Isolate 1-C | Isolate 1-D | Isolate 1-E | Isolate 1-F | Isolate 1-G | Isolate 1-H | Isolate 1-I | Isolate 1-J | Isolate 1-K | Isolate 1-L |
|---|---|---|---|---|---|---|---|---|---|---|---|---|---|---|---|---|
| NP | 708 | A to C | H to P | ✓ | ✓ | ✓ | ✓ | ✓ | ✓ | ✓ | ✓ | ✓ | ✓ | ✓ | ✓ | ✓ |
| NP | 1359 | G to A | R to K | | | | | | ✓ 3 G to A 1 G | | | | | | | |
| NP | 1423 | C to T | H to Y | ✓ | ✓ | ✓ | ✓ | ✓ | ✓ | ✓ | ✓ | ✓ | ✓ | ✓ | ✓ | ✓ |
| NP | 1443 | C to T | T to I | ✓ | ✓ | ✓ | ✓ | ✓ | ✓ | ✓ | ✓ | ✓ | ✓ | ✓ | ✓ | ✓ |
| NP | 1444 | C to T | | | | | | | | | | | | | | |
| NP | 1465 | C to T | silent | ✓ | ✓ | ✓ | ✓ | ✓ | ✓ | ✓ | ✓ | ✓ | ✓ | ✓ | ✓ | ✓ |
| NP | 1474 | C to T | silent | ✓ | ✓ | ✓ | ✓ | ✓ | ✓ | ✓ | ✓ | ✓ | ✓ | ✓ | ✓ | ✓ |
| NP | 1483 | C to T | silent | ✓ | ✓ | ✓ | ✓ | ✓ | ✓ | ✓ | ✓ | ✓ | ✓ | ✓ | ✓ | ✓ |
| NP | 1496 | C to T | L to F | ✓ | ✓ | ✓ | ✓ | ✓ | ✓ | ✓ | ✓ | ✓ | ✓ | ✓ | ✓ | ✓ |
| NP | 1547 | T to C | F to P | | | | | | | | | | | | ✓ | |
| NP | 1548 | T to C | | | | | | | | | | | | | | |
| NP | 1554 | T to C | V to A | | | | | | | | | | | | ✓ | |
| NP | 1563 | T to C | L to P | | | | | | | | | | | | ✓ | |
| NP | 1588 | T to C | silent | | | | | | | | | | | | ✓ | |
| NP | 1599 | T to C | L to S | | | | | | | | | | | | ✓ | |
| P | 2161 | C to T | silent | | | | | | | | | | | ✓ | | |
| P | 2346 | G to A | R to Q | | | | | ✓ | | | | | ✓ | | | |
| P | 2585 | C to T | H to Y | | ✓ | | | | | | | | | | | |
| M | 3670 | 2 T 2 T to C | L L to P | ✓ | | ✓ 4 T to C | ✓ 4 T to C | ✓ 1 T to C 2 T | ✓ 2 T to C 2 T | ✓ | ✓ 4 T to C | ✓ 1 T to C 3 T | | | | |
| M | 3722 | T to C | silent | | | ✓ | ✓ | | | ✓ | | | | | | |
| M | 4275 | C to A | L to I | | ✓ | | | | | | ✓ | ✓ | | | ✓ | ✓ |
| F | 5129 | T to C | F to S | ✓ | ✓ | ✓ | ✓ | ✓ | ✓ | ✓ | ✓ | ✓ | ✓ | ✓ | ✓ | ✓ |
| F | 5281 | A to G | T to A | ✓ | ✓ | ✓ | ✓ | ✓ | ✓ | ✓ | ✓ | ✓ | ✓ | ✓ | ✓ | ✓ |
| F | 5584 | 3 C 1 C to T | silent | ✓ | | ✓ 3 C to T | ✓ 3 C to T | ✓ 1 C to T 2 C | ✓ 3 C to T | ✓ | ✓ 4 T to C | | | | | |
| F | 5653 | A to G | T to A | ✓ | ✓ | ✓ | ✓ | ✓ | ✓ | ✓ | ✓ | ✓ | ✓ | ✓ | ✓ | ✓ |
| F | 5793 | C to G | D to E | ✓ | ✓ | ✓ | ✓ | ✓ | ✓ | ✓ | ✓ | ✓ | ✓ | ✓ | ✓ | ✓ |
| F | 6110 | C to T | T to I | | | | | | | | | | | | | ✓ |
| F | 6137 | 1 G 2 G to A | S to N | | | | | | | ✓ | | | | | | |
| SH | 6271 | C to T | P to S | | | | | | | | | | | | ✓ | |
| HN | 6682 | G to T | A to V | | | | | | | | | | | | | ✓ |
| HN | 7141 | T to C | silent | | | | ✓ | ✓ | ? | ✓ | ✓ | | | | | |
| HN | 7605 | C to A | T to K | | | | ✓ | | ✓ | | ✓ | | | | | |
| HN | 7804 | C to T | silent | | | | | | | ✓ | | | ✓ | | | |
| HN | 8103 | G to A | R to Q | ✓ | ✓ | ✓ | ✓ G/A mix | ✓ | ✓ | ✓ | ✓ | | | ✓ | ✓ | ✓ |
| HN | 8177 | 3 C to A 1 C | L to I | | ✓ | 3 C to A 1 C | | | | | 3 C to A | 3 C to A | | | | |
| HN | 8189 | A to G | K to E | | | | | | | | | | | ✓ | ✓ | |
| HN/L | 8406 | C to T | non-codirg | ✓ | ✓ | ✓ | ✓ | ✓ | ✓ | ✓ | ✓ | ✓ | ✓ | ✓ | ✓ | ✓ |

TABLE 1-continued

Nucleotide sequences of each virus stock.

| Gene | Base | Nucleotide Change | Amino Acid Change | Origin Japan | Isolate 1-A | Isolate 1-B | Isolate 1-C | Isolate 1-D | Isolate 1-E | Isolate 1-F | Isolate 1-G | Isolate 1-H | Isolate 1-I | Isolate 1-J | Isolate 1-K | Isolate 1-L |
|---|---|---|---|---|---|---|---|---|---|---|---|---|---|---|---|---|
| L | 9634 | 2 G 2 G to A | R to K | | | | | | ✓ | | | | | | | |
| L | 9749 | C to T | H to Y | ✓ | ✓ | ✓ | ✓ | ✓ | ✓ | ✓ | ✓ | ✓ | ✓ | ✓ | ✓ | ✓ |
| L | 9972 | C to T | S to F | ✓ | ✓ | ✓ | ✓ | ✓ | ✓ | ✓ | ✓ | ✓ | ✓ | ✓ | ✓ | ✓ |
| L | 10483 | 1 C 1 C to G | I to M | | ✓ | | | | | | | | | | | |
| L | 13328 | A to C | N to H | | ✓ | ✓ | | ✓ | ✓ | | | | | | | |
| L | 13540 | A to G | silent | | | | | | | | | | | ✓ | | |
| L | 14494 | 2 G 1 G to A | silent | ✓ | 2 G to A | 2 G to A | | 3 G to A | 3 G to A | | | | | | | |
| L | 14530 | G to A | silent | | | | | | ✓ | | | | | | | |
| L | 14663 | A to C | silent | | | | | | ✓ | | | | | | | |
| L | 15204 | T to C | I to T | | | | | | | | | | | ✓ | | |

TABLE 2

Nucleotide Sequences of cDNAs of 3X purified virus isolates.

| Gene | Base | Nucleotide Change | Amino Acid Change | Original Japan Stock | Isolate 1-A original | 1-A-3 3X purified | Isolate 1-B original | 1-B-3a 3X purified | 1-B-3b 3X purified | Isolate 1-C original | 1-C-3 3X purified | Isolate 1-I original | 1-I-3 3X purified |
|---|---|---|---|---|---|---|---|---|---|---|---|---|---|
| NP | 708 | A to C | H to P | ✓ | ✓ | ✓ | ✓ | ✓ | ✓ | ✓ | ✓ | ✓ | ✓ |
| NP | 1359 | G to A | R to K | | | | | | | | | ✓ | ✓ |
| NP | 1433 | C to T | H to Y | ✓ | ✓ | ✓ | ✓ | ✓ | ✓ | ✓ | ✓ | ✓ | ✓ |
| NP | 1443 | C to T | T to I | ✓ | ✓ | ✓ | ✓ | ✓ | ✓ | ✓ | ✓ | ✓ | ✓ |
| NP | 1444 | C to T | T to I | ✓ | ✓ | ✓ | ✓ | ✓ | ✓ | ✓ | ✓ | ✓ | ✓ |
| NP | 1465 | C to T | silent | ✓ | ✓ | ✓ | ✓ | ✓ | ✓ | ✓ | ✓ | ✓ | ✓ |
| NP | 1474 | C to T | silent | ✓ | ✓ | ✓ | ✓ | ✓ | ✓ | ✓ | ✓ | ✓ | ✓ |
| NP | 1483 | C to T | silent | ✓ | ✓ | ✓ | ✓ | ✓ | ✓ | ✓ | ✓ | ✓ | ✓ |
| NP | 1496 | C to T | L to F | ✓ | ✓ | ✓ | ✓ | ✓ | ✓ | ✓ | ✓ | ✓ | ✓ |
| P | 2346 | G to A | R to Q | | | | | | | | | ✓ | ✓ |
| P | 2585 | C to T | H to Y | | ✓ | ✓ | | | | | | | |
| M | 3670 | 2 T 2 T to C | L L to P | ✓ | | | 4 T to C ✓ | 4 T to C ✓ | 4 T to C ✓ | 4 T to C ✓ | 4 T to C ✓ | | |
| M | 3722 | T to C | silent | | | | | | | | | | |
| M | 3854 | T to G | silent | | | | | | ✓ | | | | |
| M | 4275 | C to A | L to I | | ✓ | ✓ | | | | | | | |
| F | 5129 | T to C | F to S | ✓ | ✓ | ✓ | ✓ | ✓ | ✓ | ✓ | ✓ | ✓ | ✓ |
| F | 5281 | A to G | T to A | ✓ | ✓ | ✓ | | | | | | ✓ | ✓ |
| F | 5584 | 3 C 1 C to T | silent | ✓ | | | 3 C to T | 3 C to T | 3 C to T | 3 C to T | 3 C to T | | |
| F | 5653 | A to G | T to A | ✓ | ✓ | ✓ | ✓ | ✓ | ✓ | ✓ | ✓ | ✓ | ✓ |
| F | 5793 | C to G | D to E | ✓ | ✓ | ✓ | ✓ | ✓ | ✓ | ✓ | ✓ | ✓ | ✓ |
| F | 5834 | A to C | Y to S | | | | ✓ | | | | | | |
| SH | 6271 | C to T | P to S | | | | | | | | | ✓ | ✓ |
| HN | 7141 | T to C | silent | | | | ✓ | ✓ | ✓ | ✓ | ✓ | | |
| HN | 7605 | C to A | T to K | | | | ✓ | ✓ | ✓ | | | | |
| HN | 7804 | C to T | silent | | | | | | | | | ✓ | ✓ |
| HN | 8103 | G to A | R to Q | ✓ | ✓ | ✓ | ✓ | ✓ | ✓ | ✓ | ✓ | | |
| HN | 8177 | 3 C to A 1 C | L to I | | ✓ 3 C to A 1 C | ✓ 4 C to A | | | | | | | |
| HN | 8189 | A to G | K to E | | | | | | | | | ✓ | ✓ |
| HN/L | 8406 | C to T | non-coding | ✓ | ✓ | ✓ | ✓ | ✓ | ✓ | ✓ | ✓ | ✓ | ✓ |
| L | 9749 | C to T | H to Y | ✓ | ✓ | ✓ | ✓ | ✓ | ✓ | ✓ | ✓ | ✓ | ✓ |
| L | 9972 | C to T | S to F | ✓ | ✓ | ✓ | ✓ | ✓ | ✓ | ✓ | ✓ | ✓ | ✓ |
| L | 10483 | 1 C 1 C to G | I to M | | ✓ | ✓ | | | | | | | |
| L | 13328 | A to C | N to H | | ✓ | ✓ | ✓ | ✓ | ✓ | | | | |
| L | 13540 | A to G | silent | | | | | | | | | ✓ | ✓ |
| L | 14494 | 2 G 1 G to A | silent | ✓ | | | 2 G to A | 2 G to A | 2 G to A | 2 G to A | 2 G to A | | |

Also included are MuV sequences having at least 80% (e.g., at least 85%; at least 90%; at least 92%; at least 95%; at least 98%; and at least 99%) sequence identity to the recombinant MuV provided herein provided the sequence maintains oncolytic activity.

This document also provides expression vectors that can carry a MuV provided herein into another cell (e.g., a cancer cell), where it can be replicated and/or expressed. An expression vector, also commonly referred to as an expression construct, is typically a plasmid or vector having an enhancer/promoter region controlling expression of a specific nucleotide sequence. When introduced into a cell, the expression vector utilizes cellular protein synthesis machinery to produce the virus in the cell. The expression vector of the instant disclosure includes a nucleotide sequence encoding a MuV provided herein (e.g., a MuV having oncolytic anti-cancer activity). An expression vector including a MuV provided herein can also include a nucleotide sequence encoding a detectable label. Examples of detectable label are well known in the art and can include green fluorescent protein, and luciferase. An expression vector including a MuV provided herein can also include a nucleotide sequence encoding another useful peptide. Examples of other useful peptides include, without limitation, transport peptides (e.g., sodium/iodide symporter (NIS) and nuclear localization sequence (NLS), immune modulators (e.g., interleukins, cytokines, and interferons such as interferon beta and interferon gamma), and therapeutic peptides.

This document also provides methods and materials for using a MuV provided herein. In some cases, a MuV provided herein can used for treating a patient having cancer. For example, a MuV provided herein can be administered to any appropriate patient to reduce the number of cancer cells in the mammal (e.g., suppress and/or delay tumor growth) and/or to increase survival of the mammal.

Methods for treating a patient having cancer can include administering to the patient a MuV provided herein. Any appropriate patient having cancer can be treated as described herein. For example, humans, non-human primates, monkeys, horses, bovine species, porcine species, dogs, cats, mice, and rats having cancer can be treated for cancer as described herein. In some embodiments, a human having cancer can be treated. In addition, a mammal having any particular type of cancer can be treated as described herein. For example, human with myeloma can be treated for cancer.

The method may be useful for treating any type of cancer. In some embodiments, the cancer can be a blood cancer. For example, the cancer can be, without limitation, a leukemia (cancer in the blood and bone marrow), a lymphoma (cancer in the lymphatic system), and/or myeloma (cancer of the plasma cells). In some embodiments, the cancer can be myeloma. In some embodiments, the cancer can be a carcinoma (cancer derived from epithelial cells). For example, the cancer can be, without limitation, prostate cancer, breast cancer, hepatocellular carcinoma, renal cell carcinoma, ovarian cancer, cervical cancer, lung cancer, colorectal carcinoma, colon cancer, neuroblastoma, glioma, plasmacytoma, and/or mesothelioma. In some embodiments, the cancer can be colorectal carcinoma.

Methods for treating a patient having cancer can include identifying the patient as having cancer. Examples of methods for identifying the patient as having cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests. Once identified as having cancer, the patient can be administered or instructed to self-administer a MuV provided herein.

Methods for treating a patient having cancer also can include one or more additional treatments such as surgery, chemotherapy, radiation therapy, immunotherapy, targeted therapy, hormone therapy, and/or a Janus kinase inhibitor (e.g., Ruxolitinib). In some cases, a MuV provided herein can be formulated together with one or more additional treatments (e.g., chemotherapy, radiation therapy, and/or Ruxolitinib) to form a single composition. In some cases, one or more additional treatments can be provided to a patient in a separate composition; one containing a MuV provided herein, and one containing, for example, Ruxolitinib. In cases, where a MuV provided herein and one or more additional treatments are provided separately, the administration of a MuV provided herein can be in any order relative to the administration of one or more additional treatments. For example, a MuV provided herein can be administered to a patient prior to, concurrent with, or following administration of one or more additional treatments to the patient.

A MuV can be administered by any route, e.g., IV, intramuscular, SC, oral, intranasal, inhalation, transdermal, and parenteral. In some embodiments, a MuV provided herein can be administered by IV.

Also included the instant disclosure are pharmaceutical compositions including the MuV described herein, as well as pharmaceutical compositions including the expression construct described herein. For example, a MuV or an expression vector can be formulated into a pharmaceutically acceptable composition for administration to a patient having, or at risk of having, cancer. In some embodiments, a MuV or an expression construct can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments the pharmaceutical composition is administered as a vaccine. The vaccine may prophylactic or therapeutic.

The invention will be further described in the following examples, which do not limit the scope of the invention described in the claims.

EXAMPLES

Example 1—Identification of MuV Isolates

To bring this work up to today's clinical standards for use in humans, a thorough characterization of a tcMuV-U pool was performed. Briefly, the Urabe strain of MuV (MuV-U) was plaque purified and sequenced, and was subjected to a reverse genetics system to identify MuV isolates having oncolytic activity as shown in FIG. 1.

The virus was amplified using cells grown in culture, primary human embryonic kidney (HEK) cells, and then this original Urabe mumps virus seed stock (tcMu V-U) underwent additional rounds of amplification in HEK cells and/or human amnion cells (A V3 cells) to generate virus stocks used in three different clinical trials (Asada, 1974 *Cancer* 34:1907-28; Okuno et al., 1978 *Biken J.* 21:37-49; Shimizu et al., 1988 *Cancer Detect Prev.* 12:487-95). The tcMuV-U in these stocks is an undefined mixture of isolates that have changed and possibly undergone mutations that have attenuated the wild-type phenotype as they have been passaged in cultured cells. The nucleotide sequence of the tcMuV-U virus mixture was determined from cDNAs produced from the viruses negative strand RNA genomes and are reported as the predominant sequence (e.g., average sequence) from the group (Table 3). Modifications shown in Table 3 are relative to the Urabe mumps virus sequence in NCBI Accession No: AF314558.

TABLE 3

Nucleotide sequences of the tcMuV-U virus mixture.

| Gene | Base | Nucleotide Change | Amino Acid Change | Original Japan Stock |
|---|---|---|---|---|
| NP | 708 | A to C | H to P | ✓ |
| NP | 1433 | C to T | H to Y | ✓ |
| NP | 1443 | C to T | T to I | ✓ |
| NP | 1444 | C to T | T to I | ✓ |
| NP | 1465 | C to T | silent | ✓ |
| NP | 1474 | C to T | silent | ✓ |
| NP | 1483 | C to T | silent | ✓ |
| NP | 1496 | C to T | L to F | ✓ |
| M | 3670 | 2T | L | ✓ |
| | | 2 T to C | L to P | |
| F | 5129 | T to C | F to S | ✓ |
| F | 5281 | A to G | T to A | ✓ |
| F | 5584 | 3 C | Silent | ✓ |
| | | 1 C to T | | |
| F | 5653 | A to G | T to A | ✓ |
| F | 5793 | C to G | D to E | ✓ |
| HN | 8103 | G to A | R to Q | ✓ |
| HN/L | 8406 | C to T | noncoding | ✓ |
| L | 9749 | C to T | H to Y | ✓ |
| L | 9972 | C to T | S to F | ✓ |
| L | 14494 | 2 G | silent | ✓ |
| | | 1 G to A | | |

Several nucleotides read as a mixture of different viruses (e.g., bases 3670, 5584 and 14494) demonstrating the tcMuV-U virus stock to be a mixture. The SIPAR attenuated Urabe vaccine strain (NCBI Accession No. AF314558.1) was used to compare the tcMuV-U sequences. Quite a few candidate attenuated vaccine strains were derived from the original Urabe MuV sample by various forms of culture. The unique point of the tcMuV-U stock is that a minimal amount of passaging in human cells was done to try and keep the virus from changing and attenuating too much.

The mixture of MuV isolates in the original tcMuV-U stock by identifying major strains was genetically defined by initially producing isolates of individual viruses by limiting dilution (FIG. 2).

Virus stocks from twelve individual viruses were produced, 1-A to 1-L, and the nucleotide sequence determined from cDNAs produced from the negative strand RNA genomes of each virus stock (Table 2).

After analysis of the genome sequences of these twelve individual isolates and the overall tcMu V-U mixture, it was determined that there were four major groups of different isolates by genome sequences, A, B, C and I. Each of these isolates was purified by limiting dilution a total of three times, and a representative one or two virus stocks produced for each: 1-A-3, 1-B-3a, 1-B-3b, 1-C-3 and 1-I-3. 16 unique tcMuV-U genome sequences were identified. The nucleotide sequences were determined from cDNAs of each now 3× purified virus isolate and compared to the first sequence (Table 3).

Example 2—Mumps Virus as an Oncolytic Agent

The oncolytic potential of Urabe strain of MuV was explored. MuV isolates identified in Example 1 were used to generate recombinant viruses which were evaluated in in vitro cancer models as shown in FIG. 1.

MuV isolates were administered to cancer cells. A MuV growth curve was established and a cytotoxicity assay was performed.

MuV was extremely safe with virulent Urabe strain virus (FIG. 3). MuV had significant oncolytic activity against variety of human cancers (FIG. 4).

These results demonstrate that MuV can induce significant anti-tumor immunity indicating that MuV can be a potential candidate for immune therapy.

Example 3—Recombinant Mumps Virus as a Cancer Therapeutic Agent

Methods and Materials

Viruses and Cells.

Mumps virus Urabe strain (MuV-U) was originally collected from saliva of a child with mumps symptoms in Japan, isolated after replication in cultured primary human embryonic kidney cells (HEK), and then the virus was amplified in HEK to produce a seed stock (Asada, 1974 *Cancer* 34:1907-1928). This seed stock then went through an unknown number of amplifications on HEK and/or human amnion cells (AV3) to produce virus lots for several clinical trials in Japan in the 1970's and 1980's. An aliquot of the MuV-U stock used in these clinical trials was obtained from Dr. Koichi Yamanishi (Osaka University). The Viral Vector Production Laboratory at the Mayo Clinic isolated individual virus plaques from this stock using limited dilution in Vero cells, and determined the nucleotide sequences from RT-PCR products from the viral RNA genomes.

The cell lines used in this study were obtained from American Type Culture Collection (ATCC), Manassas, Va. and were maintained in medium recommended by ATCC in 5% $CO_2$. The following cell lines were used in this study; BHK, baby hamster kidney cell line, Vero-African green monkey kidney cell line, kas6/1, JJN3, MM1, RPMI6225-human myeloma, ARH-77-plasma cell leukemia, Skov3-ovarian cancer, A549-lung adenocarcinoma, Hela-cervical cancer; mouse cancer cell lines: N2A-neuroblastoma, CT-26-colon carcinoma, LLC-lung carcinoma, NB41A3-neuroblastoma, MPC11-plasmacytoma, 4T1-breast cancer, AB12-mesothelioma, EL-4-lymphoma, RENCA-renal carcinoma, XS-63-myeloma; C6 and RG2-rat glioma. The oncolytic activities of the mumps virus infections were quantitated using MTS Cell Proliferation Colorimetric Assay Kit (BioVision Inc, Calif.).

Infectious Clone Construction and Virus Recovery.

An infectious molecular cDNA clone of MuV-UC was produced by first reverse transcribing RNA isolated from MuV-UC virus, and then amplifying overlapping regions of the genome using PCR, and the PCR products were sequentially cloned into the pSMART vector (Lucigen Corp, WI).

The rMuV-UC full-length genome was assembled between artificially introduced SnaBI and NotI restriction sites. Additional restriction sites were generated in the genome by overlapping PCR. The enhanced green fluorescent protein (eGFP) ORF was amplified from plasmid pIRES2-EGFP (Promega Corp., Madison, Wis.). A translation unit that comprises the transcription start and end signals of mumps P and M intergenic region. were introduced flanking the GFP coding region was constructed using overlapping PCR, and cloned between the G and L genes using introduced unique NheI and SmaI restriction sites. A T7 promoter and terminator were introduced at the beginning and end of the genome respectively A hepatitis delta virus ribozyme (HDV) was added to the 5'terminus to get the precise virus genome upon transcription (Ammayappan et al., 2013 *J Virol* 87:3217-3228). This completes the full-length infectious molecular clone of MuV-UC in plasmid pMuV-UC-GFP. GFP was replaced with firefly luciferase or human sodium iodide symporter (NIS) ORFs by PCR to create pMuV-UC-LUC and pMuV-UC-NIS plasmids respectively. pMuV-UC-mIFNβ-GFP was created by introduction of mIFNβ between M and F genes using SbfI and MluI restriction sites. pMuV12 UC-L13328-GFP is created by overlapping PCR using primers with mutated nucleotides. To complete the MuV-UC reverse genetics system, three helper plasmids were constructed to express the MuV-UC N, P and L proteins: pMuV-UC-N, pMuV-UC-P, and pMuV-UC-L. These sequences were PCR amplified and cloned into pCI mammalian expression vector (Promega Corp., Madison, Wis.) between NheI and NotI restriction sites.

Recombinant MuV-UCs (rMuV-UCs) were rescued as follows. BHK cells were plated at a density of $1\times10^6$ cells/well in 6-well plates. The cells were infected with the VTF-7 of vaccinia virus encoding the T7 polymerase gene at a multiplicity of infection (MOI) of 10. After an hour, the supernatant containing the vaccinia virus was removed, and the cells were transfected with 5 μg pMuV, 0.5 μg pMuV-UC-N, 0.05 μg pMuV-UC-P, and 0.2 μg pMuV-UC-L using 12 μl of Fugene 6 transfection reagent (Promega, Wis.) in Opti-MEM according to the manufacturer's instructions. The cells were incubated overnight at 37° C., and then the medium replaced with growth medium. After 7 days, the culture medium was harvested, filtered twice through a 0.2 μm filter, and the filtrate overlaid onto Vero cells for virus amplification. Five days later, the culture medium was harvested and clarified by low-speed centrifugation, and the infectious mumps virus stock titrated on fresh Vero cells. When necessary the recombinant viruses were further passaged on vero cells to amplify the viral titer. Rescued viruses were titered using a standard plaque assay described earlier (Ammayappan et al., 2013 *J Virol* 87:3217-3228). The identities of the recombinant viruses were verified by determining the nucleotide sequence of cDNA products synthesized using RT-PCR and viral genomic RNA.

Growth Curve Analysis.

Growth curve analysis was carried out as described earlier (Ammayappan et al., 2013 *J Virol* 87:3217-3228). For multistep growth curves, Vero cells were incubated with rMuV at an MOI of 0.01 for 1 hour at 37° C. Following this incubation, supernatant was removed, the monolayer was washed, and fresh growth medium was added. Supernatant was collected at predetermined time points (24, 48, 72, 96, and 120 hours), and the virus titer was determined in a standard plaque assay.

Immunofluorescence.

Fluorescence microscope was used to analyze and image green fluorescent protein (GFP)-expressing cells.

In Vitro Assays.

To measure in vitro radio-iodide uptake, cells were incubated in Hanks-buffered salt solution with 10 mM HEPES (N-2-hydroxyethylpiperazine-N'-2-ethanesulfonic acid, pH 7.3) in the presence of radio-labeled NaI ($I^{125}$ at $1\times10^5$ cpm)+/− 100 uM potassium perchlorate ($KClO_4$). After 1 hour incubation, the medium was removed and cells were washed twice. The remaining cells were re-suspended in sodium chloride. Radioactivity was measured in a gamma-counter. The assays were performed in triplicate and the means plotted. Interferon-β secretion in supernatant of infected cells was determined using enzyme-linked immunosorbent assay against murine IFNβ (VeriKine Mouse Interferon Beta ELISA Kit, PBL, N.J.). Luciferase production was measured using Luciferase Assay Systems kit (Promega, Wis.) according to the manufactures protocol.

In Vivo Experiments.

All animal protocols were reviewed and approved by the Mayo Clinic Institutional Care and Use Committee. BALB/c mice, females, 4 to 6 weeks old, were purchased from Jackson Laboratories. Mice were implanted with $5\times10^6$ mouse colon carcinoma (CT-26-LacZ) cells in the right flank. When tumors reached an average size of 0.2 to 0.5 cm3, mice were treated with a single intravenous injection of mumps virus via tail vein. Tumor volume was measured using a hand-held caliper. The mice were monitored daily until the end of the study (60 days) or when they reached the euthanasia criteria. The euthanasia criteria were as follows: clinical signs of neurotoxicity, tumor ulceration, tumor volume greater than 2000 $mm^3$, weight loss greater than 10%, or mice unable to gain access to food or water.

NCr nude mice, 4-6 weeks old, were purchased from Taconic (Hudson, N.Y.). One day before implantation of xenografts, mice were whole body irradiated (2 Gy). The next day, $5\times10^6$ KAS 6/1 cells were implanted subcutaneously in the right flank. When tumors reached a volume of 100 $mm^3$, $1\times10^7$ PFU of mumps virus, or an equal volume of saline, was injected intravenously via tail vein. The rest of the study was conducted as the Balb/C mice experiment.

A/J mice females, 4 to 6 weeks old, were purchased from Jackson Laboratories. Mice were implanted with $5\times10^6$ mouse neuroblastoma (N2A) cells in the right flank. When tumors reached an average size of 0.5 $cm^3$, mice were treated with a single intravenous injection of mumps viruses ($1\times10^7$ PFU) via tail vein. The rest of the study was conducted as above.

Immunohistochemistry.

Harvested tumors were frozen in optimal cutting medium (OCT) for cryo-sectioning. Tumor sections were analyzed by immunofluorescence for mumps virus antigens using a polyclonal rabbit anti-MuV-U serum, followed by Alexa-labeled anti-rabbit IgG secondary antibody (Life Technologies, N.Y.), and cellular nuclei were stained with Hoechst 33342 (Life Technologies, N.Y.).

Statistical Analyses.

An unpaired two-tailed Student t test was carried out to compare the values. Survival curve analysis was done using the Prism 4.0 program (GraphPad Software, San Diego, Calif.). Survival curves were plotted according to the Kaplan-Meier method, and survival function across treatment groups was compared using log rank test analyses.

Results

Mumps Virus Urabe Strain

An aliquot of the mumps virus Urabe strain used in oncolytic virotherapy human clinical trials in Japan in the 1970's and 1980's was obtained. A representative clone, MuV-U Clone 1-C-3 (MuV-UC-WT) was isolated, characterized, and used in this study. One unique aspect of this MuV-UC virus stock was the minimal amplification in cultured cells that may have minimized the attenuation from the original patient isolate.

The Development of a Reverse Genetics System Based on Mumps Virus Urabe Strain

A reverse genetics platform based on the nucleotide sequence of the MuV-UC isolate was constructed initially with an additional transcription unit containing the GFP coding sequence flanked by unique restriction enzyme cloning sites between MuV-UC genes FIN and L, in a plasmid vector pMuV-UC-GFP. Negative-strand RNA can be synthesized using T7 polymerase and the T7 transcription elements flanking the MuV-UC genome along with three MuV-UC based helper plasmids expressing MuV-UC N, P and L proteins. BHK cells infected with a vaccinia virus vector encoding the T7 polymerase were then transfected with the infectious MuV-UC plasmid along with the three helper plasmids to rescue recombinant virus. After successful rescue in BHK cells, the recombinant MuV-UC virus was further propagated in Vero cells to produce virus stocks (FIG. 5*a*). When growth potential of recombinant mumps virus expressing GFP was compared with wild-type virus, it showed better growth rate (FIG. 5*b*).

To test the genomic stability and transgene expression abilities of the recombinant MuV-UC platform, several other recombinant viruses with different useful transgenes for in vivo bio-distribution and efficacy studies were constructed (FIG. 6*a*). The GFP coding region was replaced with the luciferase gene (rMuV-UC-LUC), or the human sodium iodide symporter (NIS) gene (rMUV-UC-NIS). Whether two transgenes could be inserted and expressed from the rMuV-UC platform was also tested by adding an additional transgene, mouse interferon beta (mIFNβ), in between M and F genes of rMuV-UC-GFP creating rMuV-UC-mIFNβ-GFP that should express both the mIFNβ and GFP. All the recombinant mumps viruses replicated well on Vero cells (FIG. 6*b*). The rMuV-UC-mIFNβ-GFP with two transgenes replicated to a lower titer compare to viruses with single transgenes. All transgenes delivered by the recombinant mumps viruses were well expressed (FIG. 6C-E).

Oncolytic Activity of rMuV-UC-GFP Replication in Tumor Cell Lines

Since oncolytic virotherapy not only expects the virus to directly kill tumor cells but then cause a unique immune response to the tumor to completely cure the patient, efficacy models that can evaluate both strategies of this two-pronged therapeutic approach are best. Therefore, while we want to know the efficacy of mumps virus for treating human tumors, human tumor xenografts in nude mice can only evaluate the virus killing therapeutic component. Since some syngeneic mouse tumors models respond similarly to their human tumor counterparts, the infectivity and oncolytic activity of the rMuV-UC-GFP virus on a variety of human and mouse tumor cell lines was investigated. The oncolytic efficacy of rMuV-UC-GFP in various human cancer cell lines was tested (FIG. 7A). The human tumor cell lines were infected with rMuV-UC-GFP at an M.O.I. 1.0 and analyzed 5 days later by fluorescence microscopy for GFP expression. This analysis demonstrated that mumps virus could infect most human tumor cell lines tested.

Most of the mouse tumor cell lines are non-permissive to robust rMuV-UC-GFP virus infection and replication, with only the N2A neuroblastoma cell line and the CT-26-LacZ colon cancer cell lines showing significant numbers of GFP positive cells (FIG. 7B). Both the N2A and CT-26-LacZ tumor lines permitted some rMuV-UC-GFP replication but at significantly lower titers compared to rMuV-UC-GFP replication on human Kas 6/1 tumor cells (FIG. 7C). Significant cell killing was observed in most human tumor lines tested, however the extent as well as the rate of cell killing can differ substantially between individual tumor cell lines (FIG. 8). Very little cell killing was observed in the infected mouse tumor lines with the best in the N2A and CT-26-LacZ by day 7, where the mumps virus replicated relatively well.

Since the neurovirulence studies of mumps virus has been carried out in rat models, the infectivity and replication of rMuV-UC-GFP in some of the rat tumor cell lines was tested. C6 and RG2 are two rat glioma tumor cell lines, and were infected with mumps virus at different MOI. RG2 glioma cells were more permissive to MuV infection compared to C6 cells (FIG. 9A). Mumps virus multiplies better in RG2 cells reaching its peak titer ($6\times10^5$ pfu/mL) at 72 hours post-infection (FIG. 9B). The titer produced by RG2 cells is almost two logs higher than C6 cells but more than a log lower than Vero cells. In correlation with the higher rMuV-UC-GFP replication in RG2 cells compared to C6 cells, up to 60% of the RG2 cells were killed by the mumps virus compared to just 10-20% of C6 cells as determined by MTS assay, confirmed the higher infectivity in RG2 cells (FIG. 9C).

Modulation of Interferon Pathway and its Effect on Mumps Virus Replication

It has been shown that mumps virus infection in non-permissive rodent cells resulted in abortive infection (Yamada et al., 1984 *J Gen Virol* 65:973-980). This may be caused by the presence of antiviral machinery or due to inefficient penetration of virus into the cell. Since interferon is one of the obstacles that could prevent MuV replication, some of the less permissive cell lines were treated with Janus kinase inhibitor, Ruxolitinib (Escobar-Zarate et al., 2013 *Cancer Gene Ther* 20:582-589), and then infected the treated cells with rMuV-UC-GFP. The Ruxolitinib treatment increased the viral infection significantly in rat glioma (C6), mouse lung carcinoma (LLC) cells and also to some extent in CT-26 colon carcinoma cells, but not in plasmacytoma (MPC11) and human myeloma (MM1) cells (FIG. 10). This suggests that individual cell lines not only differ in the innate immune defense but also employ more than one mechanism to restrict viral replication. So the low infectivity of MuV in mouse tumor cells may be the result of multiple cellular factors rather than single one that control different steps in the mumps virus life-cycle.

Oncolytic Efficacy of Mumps Viruses in Immunocompetent Mouse Models

To test the oncolytic activity of mumps virus in immunocompetent mouse models, pilot preliminary studies using the two relatively permissive mouse cancer cell lines to mumps virus infection, colon carcinoma (CT-26-LacZ) and neuroblastoma (N2A), were conducted. These tumor cells were implanted into the flanks of syngeneic mice, Balb/C and A/J respectively. Once the tumors reached a significant size, mumps viruses were administered intravenously through the tail vein. In CT-26-LacZ model, groups of mice were treated with rMuV-UC-GFP at $10^6$ and $10^7$, rMuV UC-LUC at $10^7$, MuV-UC at $10^7$, and a saline control. Some of the mice with CT-26-LacZ tumors treated with rMuV-UC-LUC or MuV-UC virus had delay in their tumor growth and had better overall survival with one rMuV-UC-LUC treated mouse and two MuV-UC virus treated mice having a complete response (FIG. 11). However, immunohistochemical analysis of tumor tissue on day 14 doesn't show any mumps virus positive staining and also the luciferase imaging on day 7 and 14 yielded no positive signal (Data not shown). This suggests that there may be an involvement of immune system in tumor suppression.

Figures 13A, 13B:
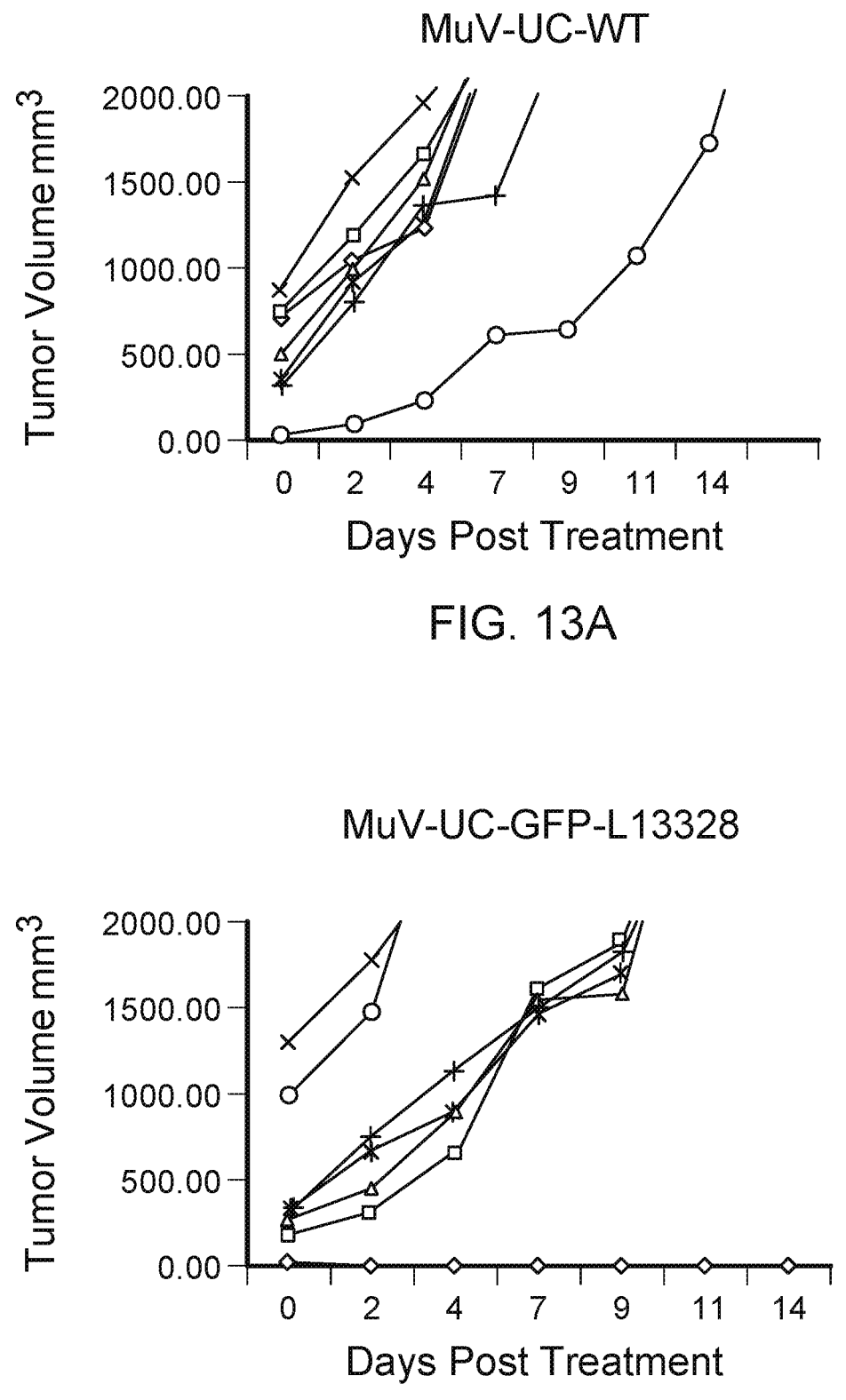
Figure 13C:
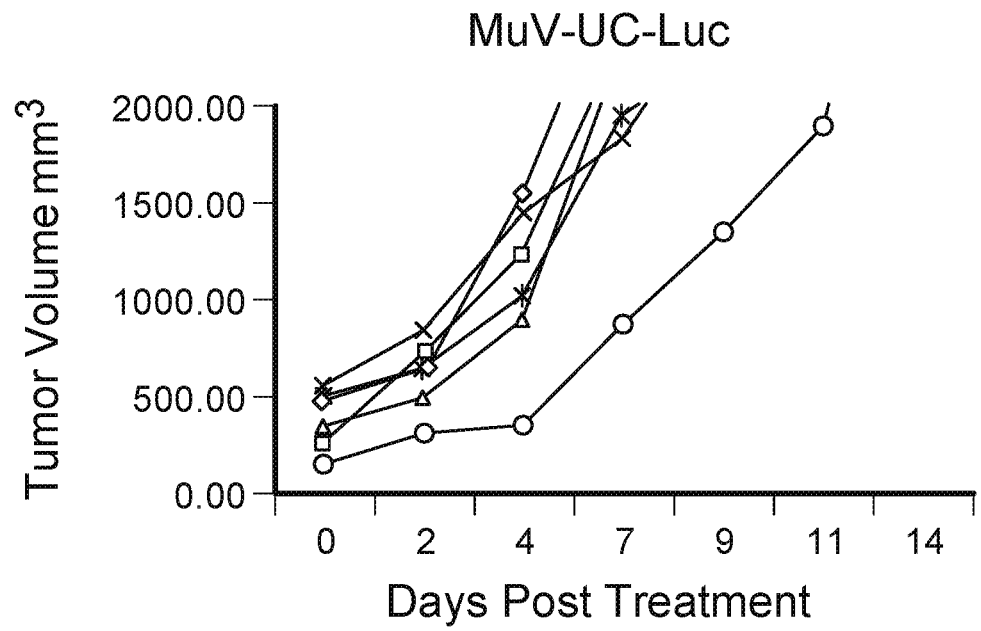
Figure 13D:
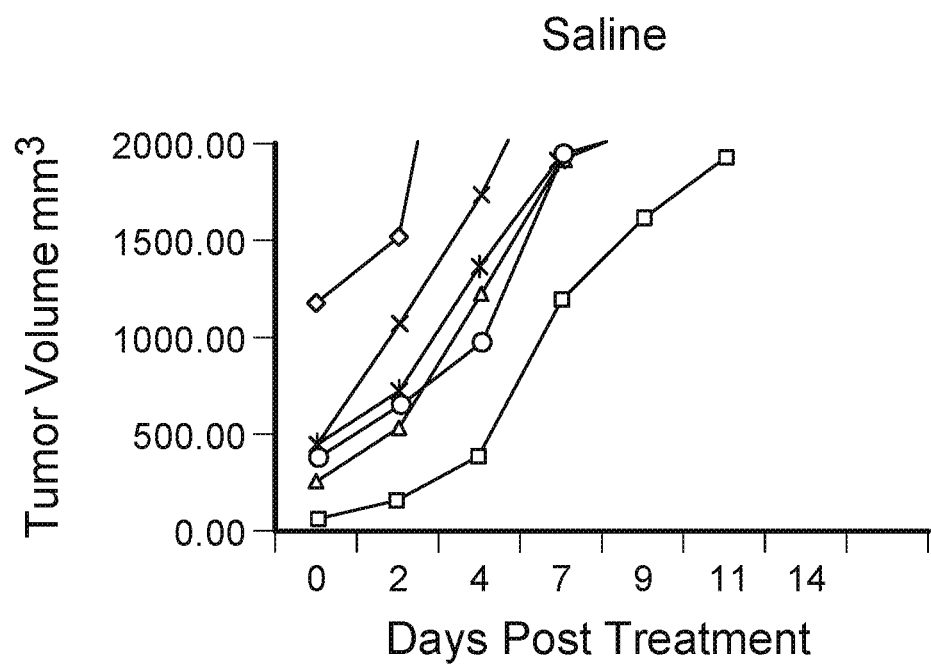
Figure 13E:
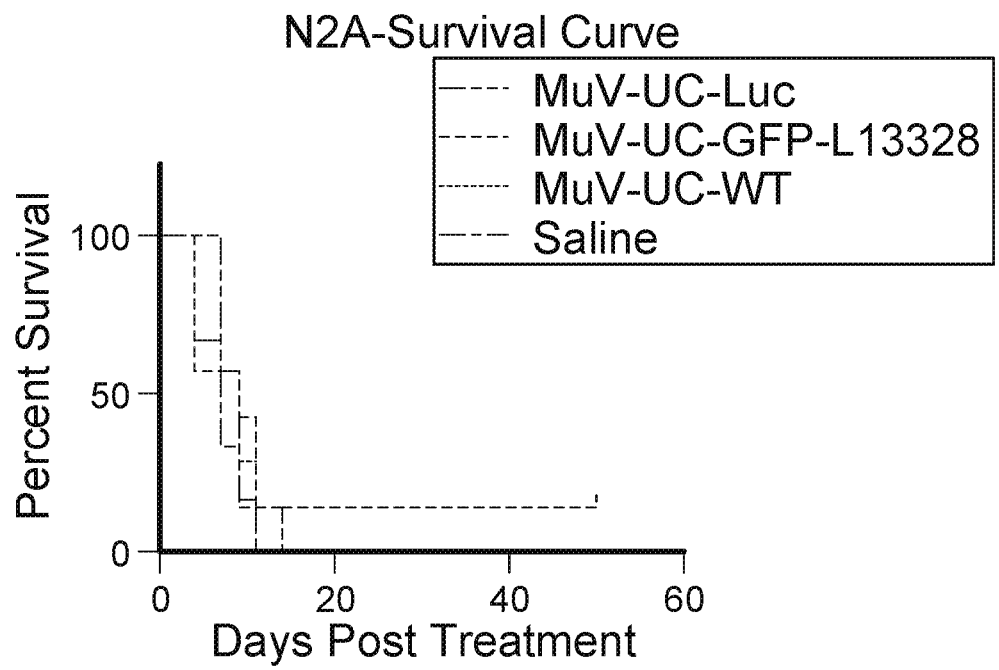
Figure 14A:
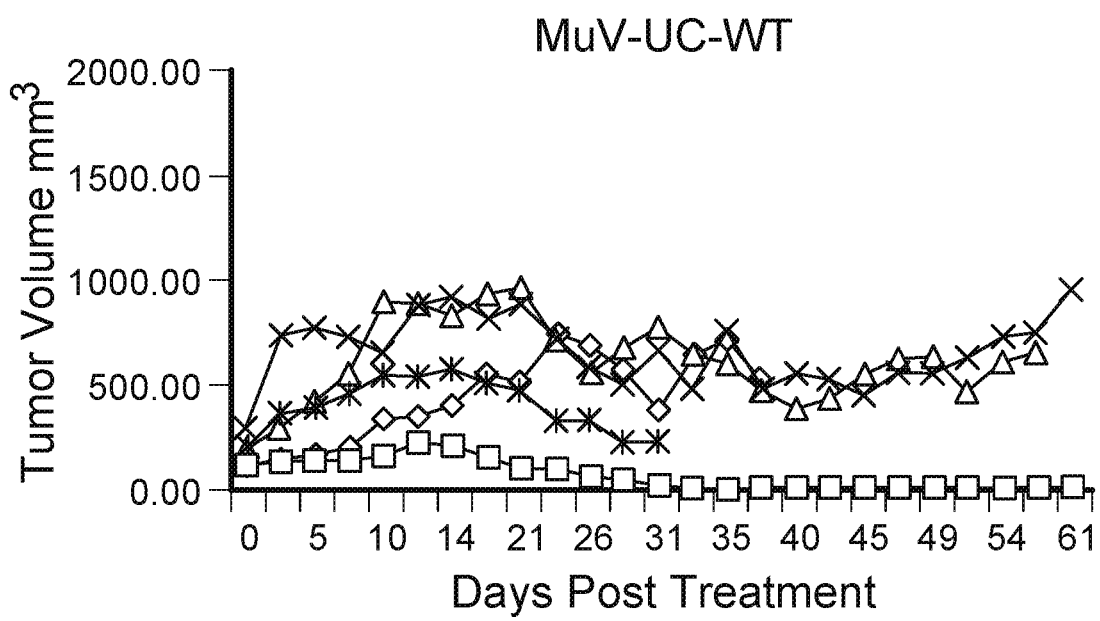
Figure 14B:
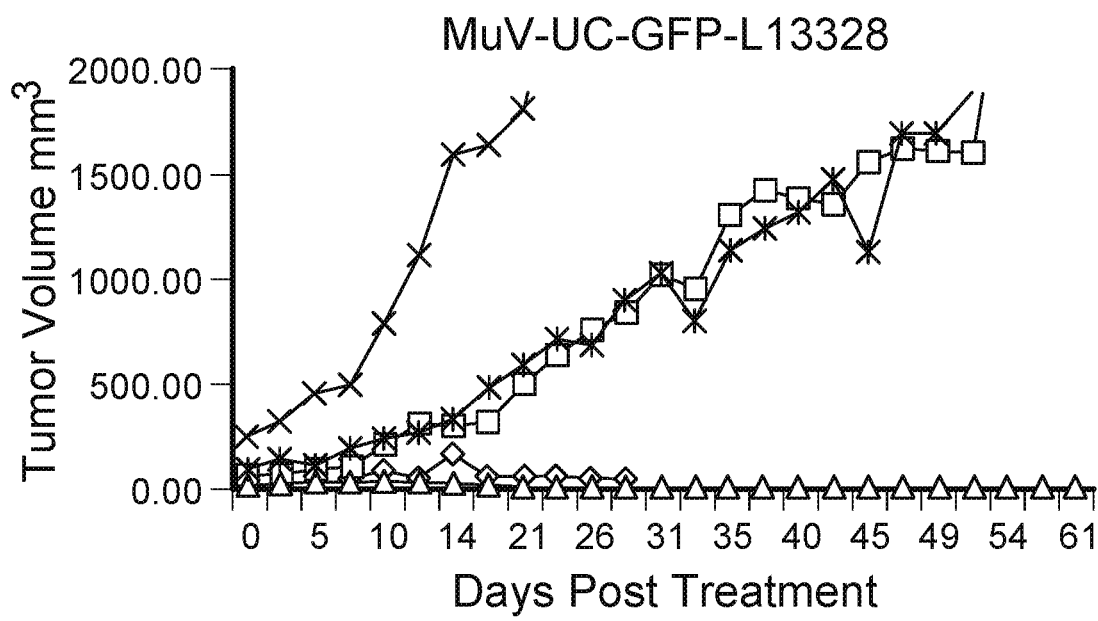
Figure 14C:
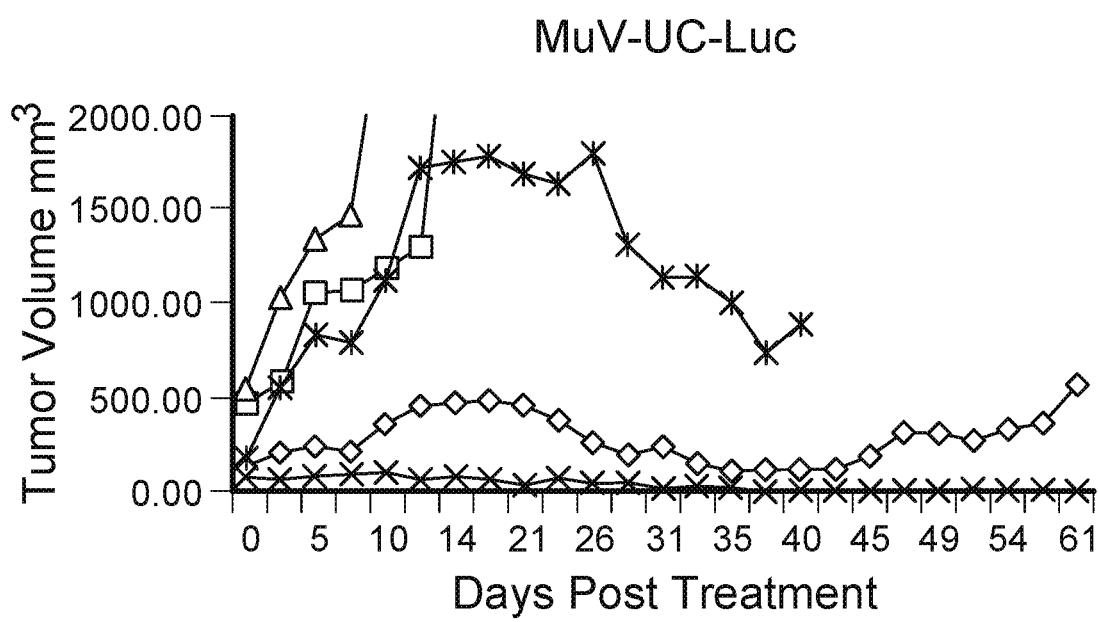
Figure 14D:
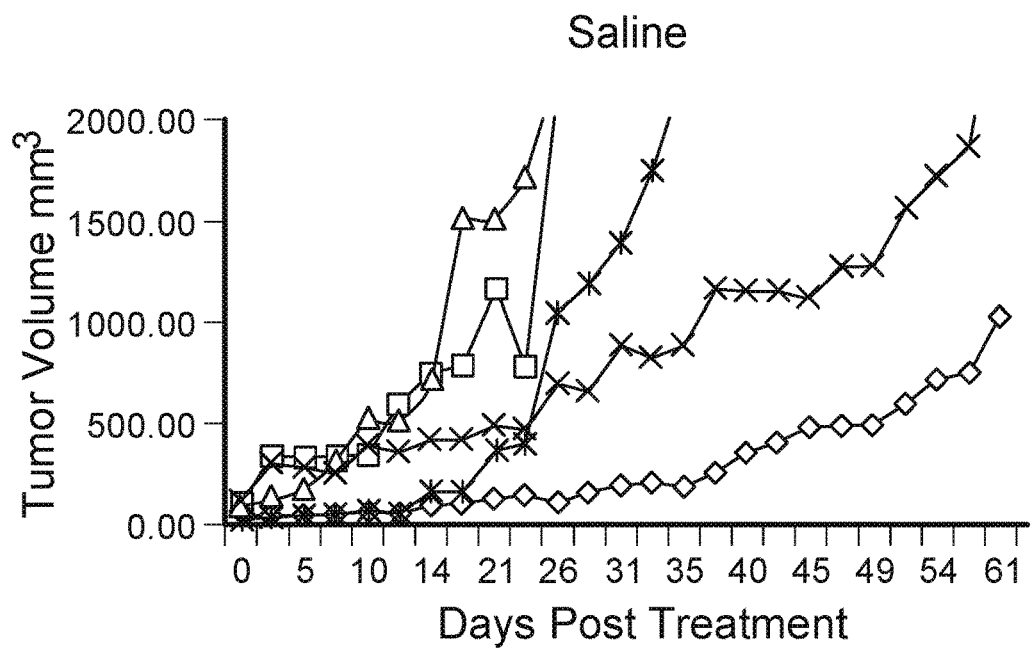
Figure 14E:
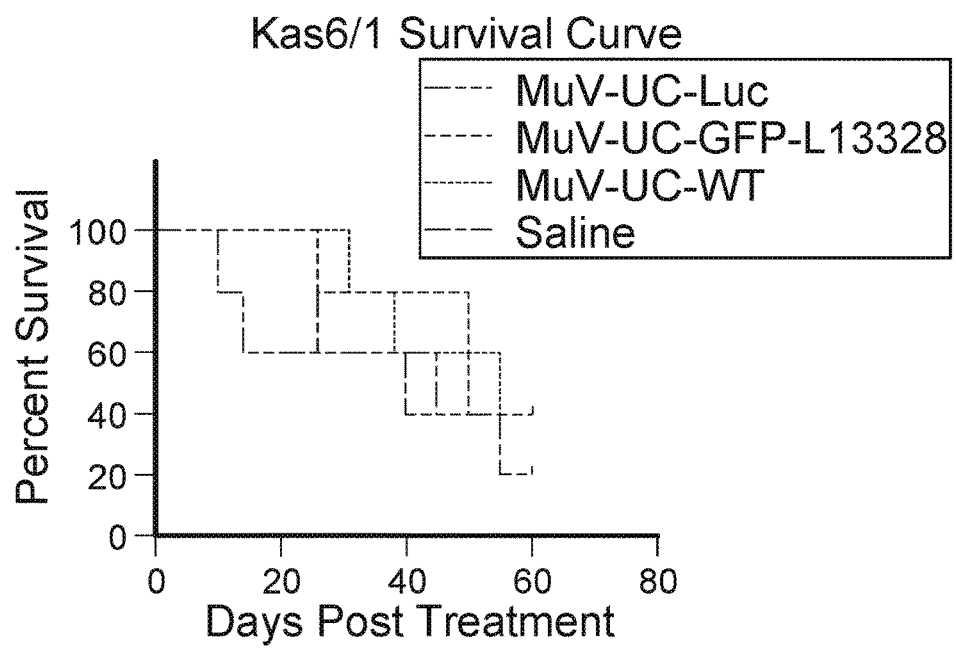

Mutating a single amino acid in polymerase gene increased the replication rate of mumps virus (nt13328, aa N to H). When this virus was compared with MuV-UC-WT and rMuV-UC-GFP, no significance difference was observed in oncolytic activity in in vitro studies (FIG. 12). This virus (rMuV-UC1 $L_{13328}$-GFP) was used for the rest of the animal studies. In the N2A model, mice were treated with rMuV UC-LUC, rMuV-UC-$L_{13328}$-GFP, MuV-UC, and equal amount of saline. No significant anti-tumor activity was seen in the N2A tumor model possibly due to the aggressive nature of N2A tumor with most of the mice requiring sacrifice around 10 days post-infection (FIG. 13). However, one mouse survived in rMuV-UC-$L_{13328}$-GFP treated group.

Oncolytic Efficacy of Mumps Virus in Human Myeloma Model

Figure 15:
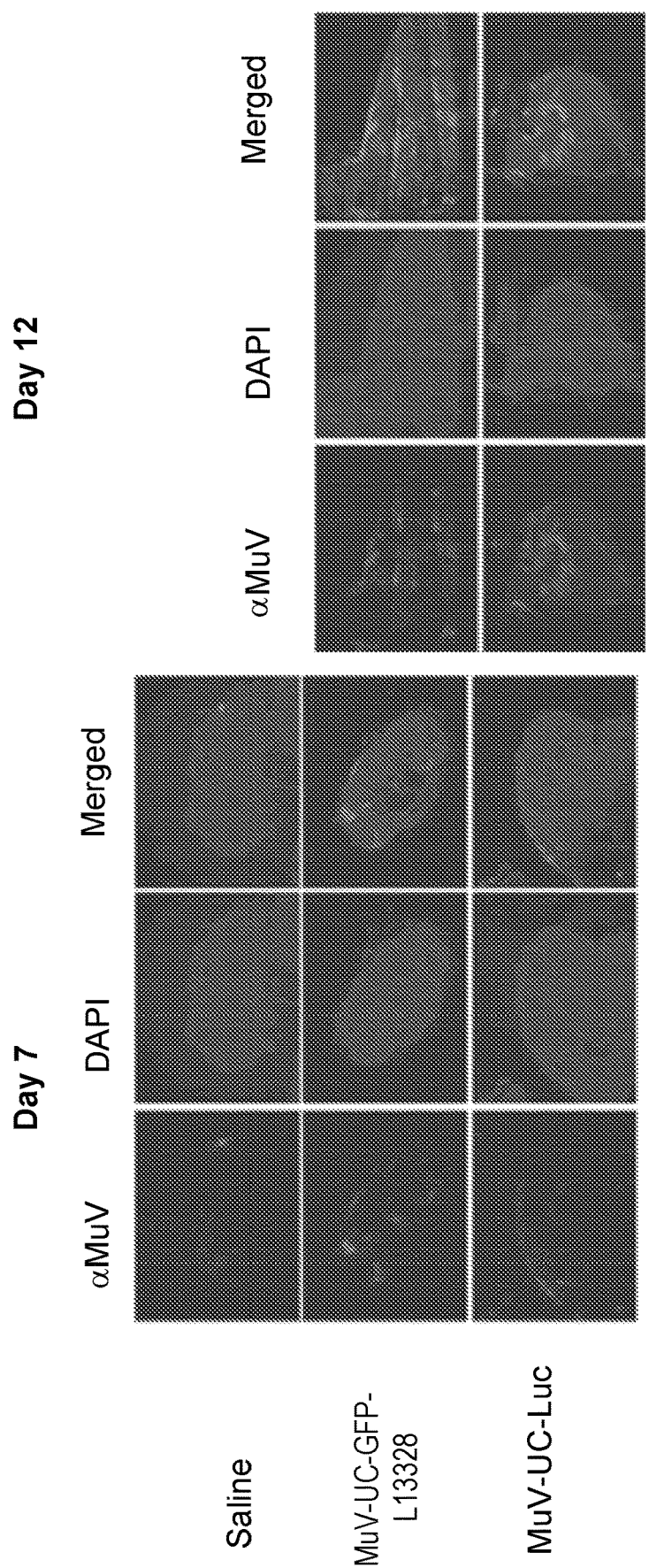

In order to initially assess the antitumor activity of the mumps viruses in vivo in a human myeloma model, human myeloma tumor cells (Kas6/1) were implanted into the flanks of nude mice. Once the tumor reached an appreciable size, $10^7$ PFU of rMuV-UC-LUC, rMuV-UC-$L_{13328}$-GFP, MuV-UC or saline were injected intravenously thorough the tail vein, and the mice observed for 60 days (FIG. 14). Some variability was seen in the growth of the individual tumor xenografts in saline treated animals, with 4 of 5 animals succumbing to tumor load by 60 days. This variability was seen in all four groups and prevented the survival results from reaching statistical significance. However, the data clearly shows the MuV-UC isolate suppressed the tumor growth in all five animals, with one animal having a complete response. The results from mice treated with the recombinant viruses were promising with one complete response and possibly two tumors controlled when treated with rMuV-UC-LUC, while two animals had a complete response to treatment with rMuV-UC-$L_{13328}$-GFP. To confirm virus replication, tumors were harvested from mice on day 7 and day 12 after virus administration and analyzed for mumps virus antigens. All tumors were positive for mumps viral proteins on day 7 and showed increased staining on day 12. MuV-UC treated tumors having comparatively better infectivity and spread relative to the tumors treated with the recombinant mumps viruses (FIG. 15). Since these studies involved single administration of mumps virus, other treatment regimens could possibly improve oncolytic efficacy significantly.

CONCLUSIONS

These results demonstrate that recombinant MuV can infect wide variety of human tumor cells, and that MuV show significant tumor suppression, delay in tumor growth, and also statistically significant increase in survival rate.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant mumps virus (MuV) having oncolytic anti-cancer activity, wherein said recombinant MuV comprises nucleic acid encoding a modified RNA polymerase large (L) subunit protein comprising a N to H substitution at amino acid 1631 as numbered in SEQ ID NO:10.

2. The recombinant MuV of claim 1, wherein said recombinant MuV is a replication competent MuV.

3. The recombinant MuV of claim 1, wherein said modification in an RNA polymerase L subunit coding sequence comprises an A to C substitution at nucleotide 13328 as numbered in SEQ ID NO: 1.

4. A method for treating a patient having cancer, the method comprising:

administering to the patient a recombinant mumps virus (MuV) having oncolytic anticancer activity, wherein said recombinant MuV comprises nucleic acid encoding a modified RNA polymerase large (L) subunit protein comprising a N to H substitution at amino acid 1631 as numbered in SEQ ID NO:10.

5. The method of claim 4, wherein the cancer is a blood cancer selected from leukemia, lymphoma, or myeloma.

6. The method claim 5, wherein the blood cancer is myeloma.

7. The method of claim 4, wherein the cancer is a carcinoma selected from prostate cancer, breast cancer, hepatocellular carcinoma, lung cancer, or colorectal carcinoma.

8. The method of claim 7, wherein the carcinoma is colorectal carcinoma.

9. The method of claim 4, wherein said recombinant MuV is a replication competent MuV.

10. The method of claim 4, wherein said modification in an RNA polymerase L subunit coding sequence comprises an A to C substitution at nucleotide 13328 as numbered in SEQ ID NO:1.

11. The method of claim 4, further comprising administering ruxolitinib.

12. An expression construct comprising a nucleotide sequence encoding a recombinant MuV having oncolytic anti-cancer activity, wherein said recombinant MuV comprises nucleic acid encoding a modified RNA polymerase large (L) subunit protein comprising a N to H substitution at amino acid 1631 as numbered in SEQ ID NO:10.

13. The expression construct of claim 12, wherein said recombinant MuV is a replication competent MuV.

14. The expression construct of claim 12, wherein said modification in an RNA polymerase L subunit coding sequence comprises an A to C substitution at nucleotide 13328 as numbered in SEQ ID NO: 1.

15. A method for treating a patient having cancer, the method comprising:

administering to the patient an expression construct comprising a nucleotide sequence encoding a recombinant mumps virus (MuV) having oncolytic anti-cancer activity, wherein said recombinant MuV comprises nucleic acid encoding a modified RNA polymerase large (L) subunit protein comprising a N to H substitution at amino acid 1631 as numbered in SEQ ID NO:10.

16. The method of claim 15, wherein the cancer is a blood cancer selected from leukemia, lymphoma, or myeloma.

17. The method claim 16, wherein the blood cancer myeloma.

18. The method of claim 15, wherein the cancer is a carcinoma selected from prostate cancer, breast cancer, hepatocellular carcinoma, lung cancer, or colorectal carcinoma.

19. The method of claim 18, wherein the carcinoma is colorectal carcinoma.

20. The method of claim 15, wherein said recombinant MuV is a replication competent MuV.

21. The method of claim 15, wherein said modification in an RNA polymerase L subunit coding sequence comprises an A to C substitution at nucleotide 13328 as numbered in SEQ ID NO: 1.

22. The method of claim 15, further comprising administering ruxolitinib.

* * * * *

SEQUENCE LISTING

```
<160> NUMBER OF SEQ ID NOS: 10

<210> SEQ ID NO 1
<211> LENGTH: 15384
<212> TYPE: DNA
<213> ORGANISM: Mumps virus

<400> SEQUENCE: 1
accaagggga aaatggagat gggatgttgg tagaacaaat agtgtaagaa acagtaagcc      60
cggaagtggt gttttgcgat ttcgaggccg ggctcgatcc tcacctttca ttgtcgatag     120
gggacatttt gacactacct ggaaaatgtc gtctgtgctc aaagcatttg agcgattcac     180
gatagaacag gaacttcaag acaggggtga ggagggttca attccgccgg agactttaaa     240
gtcagcagtc aaagtcttcg ttattaacac acccaatccc accacacgct accagatgct     300
aaacttttgc ctaaggataa tctgcagtca aaatgctagg gcatctcaca gggtaggtgc     360
attgataaca ttattctcac ttccctcagc aggcatgcaa aatcatatta gattagcaga     420
tagatcacct gaagctcaga tagaacgctg tgagattgac ggttttgagc ctggcacata     480
taggctaatt ccgaatgcac gcgccaatct tactgccaat gaaattgctg cctatgcttt     540
gcttgcagac gacctccctc caaccataaa taatggaact ccctatgtac atgcagatgt     600
tgaaggacag ccatgtgatg agattgagca attcctagat cgatgctaca gtgtactaat     660
ccaggcttgg gtgatggtct gtaaatgtat gacagcgtac gaccaacatg ctggatctgc     720
tgatcggcgg tttgcaaaat accagcaaca aggtcgcctg gaagcaagat acatgctgca     780
gccggaggcc caaaggttga tccaaactgc catcaggaaa agtcttgttg ttagacagta     840
ccttactttc gaactccagt tggcaagacg gcaggggttg ctatcaaaca gatactatgc     900
```

```
aatggtgggt gacattggaa agtacattga gaattcaggc cttactgcct tctttctcac    960
cctcaaatat gcactaggta ccaaatggag tcctctgtca ttggccgcat tcaccggtga   1020
actcactaag ctccgatccc tgatgatgtt atatcgagat ctcggagaac aagccagata   1080
ccttgctttg ttggaggctc cccaaataat ggactttgca cccggaggct acccattgat   1140
attcagttat gctatgggag tcggtacagt cctagatgtc caaatgcgaa attcactta    1200
tgcacgacct ttcctaaatg gttattattt ccagattggg gttgagactg cacgacggca   1260
acaaggcact gttgataaca gagtagcaga tgatctaggc ctgactcctg agcaaaggac   1320
tgaggttact caacttgttg acaggcttgc aaggggcaga ggtgcgggga taccaggtgg   1380
gcccgtgaat ccttttgttc ctccagttca acagcaacaa cctgctgccg cacatgagga   1440
caccctgca ttggaggaat cagacgacga cggcgatgaa gacggggtg caggactcca    1500
aaatggagca caagcaccag ctgcaagaca gggaggccaa aatgacttca gagtacagcc   1560
actacaggat ccaattcaag cacaactttt catgccatta tatcctcaag tcagcaacat   1620
cccaaatcat cagaatcatc agatcaatcg cgtcgggggg atggaacacc aagatttatt   1680
acgatacaac gagaatggtg atcctcaaca agatgcaagg ggcgaacacg aaacacctt    1740
cccaaacaat cctaatcaaa cgcacagtc gcaagtgggc gactgggatg agtaaatcac    1800
tgacatgatc aaactacccc caattgcaat aaccccagga caatctagcc acagctaact   1860
gcccaaatcc actacattcc attcatattt agtctttaag aaaaaattag gcccggaaag   1920
aattagttct acgagcatcg acacaattat cttgatcgtg tttctttccg ggcaagccat   1980
ggaccaattt ataaaacaag atgagactgg tgatttaatt gagacaggaa tgaacgttgc   2040
aaatcatttc ctatccgccc ccattcaggg aaccaactcg ttgagcaagg ccacaatcat   2100
ccctggcgtt gcaccagtac tcattggcaa tccagagcaa aagaacattc agtacccac    2160
cacatcacat caggggtcca agtcaaaggg cagaggctca ggggccaggc ccatcatagt   2220
ctcatcctcc gaaggaggca ctggagggac tcagattcct gagccccttt tcgcacaaac   2280
aggacaaggt ggcattgtca ccaccgtttta tcaggatcca actatccaac caacaggttc   2340
atatcgaagt gtggaattgg ctaagatagg aaaagagaga atgattaatc gatttgttga   2400
aaaaccaaga acctcaacgc cggtaacaga atttaagagg ggggccggga gcggctgctc   2460
aaggccagac aatccaagag gagggcatag acgggaatgg agcctcagct gggtccaagg   2520
agaggtccgg gtctttgagt ggtgcaaccc catatgctca cctatcactg ccacagcaag   2580
attccactcc tgcaaatgtg ggaattgccc cgcaaagtgc gatcagtgcg aacgagatta   2640
tggacctcct tagagggatg gatgctcgcc tgcaacatct tgaacaaaag gtggacaagg   2700
tgcttgcaca gggcagcatg gtgacccaaa taaagaatga attatcaaca gtaaagacaa   2760
cactagctac aattgaagga atgatggcga cagtaaagat catggatcct ggaaacccga   2820
caggggtccc agttgatgag cttagaagaa gttttagtga tcatgtaaca attgttagtg   2880
gaccaggaga tgtgtcattc agctccggtg aagaacccac actgtatttg gatgaactag   2940
cgaggcctgt cccaaagccc cgtcctgcaa agcagccaaa accccaacca gtaaaggatt   3000
tagcaggacg gaaagtgatg ataactaaaa tgatcactga ctgtgtggcc aatcctcaaa   3060
tgaagcaggt gtttgagcaa cgattggcaa gagccagcac cgaggatgct ctgaatgata   3120
tcaagcgaga catcataagg agcgccatat gaactcacca ggaacaccag actcacggga   3180
aaatccacaa actgaaagcc acaatgattc cctgttaaat aaaaaataag cacgaacaca   3240
```

```
agtccaatcc aaccatagca gcaatggccg ggtcacagat caaaatccct cttccaaagc    3300
cccctgattc agactctcaa agactaaatg cattccctgt aatcgtggct caagaaggca    3360
aaggacgact cctcagacag atcagactta ggaaaatatt atcagggat ccgtctgatc     3420 atcaaattac atttgtgaat acatatggat tcatccgtgc cactccagaa acatccgagt    3480
tcatctctga atcatcacaa cagaaggtga ctcctgtagt gacggcgtgc atgctgtcct    3540
tcggcgctgg accagtccta gaagacccac aacatatgct gaaagctctt gatcagacag    3600
acatcagggt tcggaagaca gcgagtgata aagagcagat cttattcgag atcaaccgca    3660
tccccaatct attcaggcat catcaaatat ctgcggacca tctgattcaa gccagctccg    3720
ataaatatgt caagtcacca gcaaagttga ttgcaggagt aaattacatc tactgtgtca    3780 cattttatc tgtgacagtt tgttctgcct cactcaagtt tcgagttgcg cgcccattgc     3840
ttgctgcacg atctagatta gtaagagcag ttcagatgga agttttgctt cgagtaactt    3900
gcaaaaggaa ttcccaaatg gcaaagagca tgttaaatga ccctgatgga gaagggtgca    3960
ttgcatccgt gtggttccac ctgtgtaatc tgtgcaaagg caggaataaa cttagaagtt    4020
acgatgaaaa ttattttgca tctaagtgcc gtaagatgaa tctgacagtc agcataggag    4080
acatgtgggg accaaccatt ctagtccatg caggcggtca cattccgaca actgcaaaac    4140
cttttttcaa ctcaagaggc tgggtctgcc accccatcca ccaatcatca ccatcgttgg    4200
cgaagaccct atggtcatct gggtgtgaaa tcaaggctgc cagtgctatc ctccagggct    4260
cagactatgc atcacttgca aaaactgatg acataatata ttcaaagata aaagtcgata    4320
aagatgcggc caactacaaa ggagtatcct ggagtccatt caggaagtct gcctcaatga    4380
gcaacctatg agaatttcat ctattccccc tgatgcctcc aggagaatca acaatcagtc    4440
cgattttacc ggtggtaact tgattgaaat tatagaaaaa ataagcctag aaggacatct    4500
tacttctcga ctttccaact ttgaaaatag aattgatcag taatcatgaa ggcttttta    4560 gttacttgct taagctttgc agtcttttca tcttctgtat gtgtgaatat caacatcttg    4620
cagcaaattg gatatatcaa gcaacaagtc aggcaactaa gctattactc acaaagttca    4680
agctcctaca tagtggtcaa gcttttaccg aatatccaac ccattgataa cagctgtgaa    4740
tttaagagtg taactcaata caataagacc ttgagtaatt tgcttcttcc aattgcagaa    4800
aacataaaca atattgcatc gccctcatct gggtcaagac ggcataaaag gtttgctggt    4860
attgctattg gcattgctgc gctcggtgtt gcgaccgcag cacaagtaac tgccgctgtc    4920
tcattagttc aagcacagac aaatgcacgt gcaatagcgg cgatgaaaaa ttcaatacaa    4980
gcaactaatc gagcagtctt cgaagtgaag gaaggcactc aacagttagc tatagcggta    5040
caagcaatac aagaccacat caatactatt atgaacaccc aattgaacaa tatgtcttgt    5100
cagatccttg ataaccagct tgcaactttc ctaggattat acctaacaga attaacaaca    5160
gtgtttcagc cacaattaat taatccggca ttgtcaccga ttagtataca agccttgagg    5220
tctttgcttg aagtatgac gcctgcagtg gtccaagcaa cattatctac ttcaatctct     5280
actgctgaaa tactaagtgc cggtctaatg gagggtcaga ttgtttctgt tctgctagat    5340
gagatgcaga tgatagttaa gataaatatt ccaactattg tcacacaatc aaatgcattg    5400
gtgattgact tctactcaat ttcgagcttt attaataatc aggaatccat aatccaattg    5460
ccagacagaa tcttggagat cgggaatgaa caatggagct atccagctaa aaattgtaag    5520
ttgacaagac accacatatt ctgccaatac aatgaggcag agaggctgag cctagaatca    5580
aaactatgcc ttgcaggcaa tataagtgcc tgtgtgttct cacccatagc agggagttat    5640
```

```
atgaggcgat ttacggcact ggatggaaca attgttgcaa actgtcgaag tctaacgtgt    5700
ctatgcaaga atccatctta tcctatatac caacctgacc atcatgcagt cacgaccatt    5760
gatctaaccg catgtcaaac attgtcccta gacggattgg atttcagcat tgtctctcta    5820
agcaacatca cttacgctga gaaccttacc atttcattgt ctcagacaat caatactcaa    5880
cccattgaca tatcaactga actgagtaag gttaatgcat ccctccaaaa tgccgttaag    5940
tacataaagg agagcaacca tcagctccaa tctgtgagtg taaactccaa aatcggagct    6000
ataattgtag cagccttagt tttgagcatt ctgtcaatta tcatttcgct attgttttgc    6060
tgctgggctt acattgcaac taaagaaatc agaagaatca acttcaaaac aaatcatatc    6120
aatacaatat caagtagtgt cgatgatctc attaggtact aatcctaaca ttgtgattca    6180
tcctgcattg agaaaagatt tagaaaaaaa ctaaattaag aatgaatctc ctggggtcgt    6240
aacgtctcgt gaccctgccg ttgcactatg ccggcgatcc aacctcccct tatcccaaca    6300
tttctattgc taattcttct ctctctgatc gtaactttgt atgtctggat tatatcaacc    6360
atcacttaca agactgtggt gcgacatgca gcactgtacc agagatcctt ctttcgctgg    6420
agttttgatc actcactcta gaaagatctc cagctgggac aagtcccaat ccatcatgcg    6480
agaacaagct gcatccaaat gatgccgttc aatcatgaga cataaagaaa aaatcaagcc    6540
agaacaagct taggatcaca atacaacaca gaacccagc  tgccatcata actgttctct    6600
ggccgctcga agatggagc  cctcaaaact cttcacaatg tcagacaatg ccacctttgc    6660
acctggacct tttatcaatg cggcagacaa gaagacgttc cgaacctgct tccgaatatt    6720
ggtactgtct gtacaagctg ttacccttat attagttatt gtcactttag gtgagcttgt    6780
gaggatgatc aatgatcaag gcttgagcaa tcagttgtct tcaattgcag acaagataag    6840
agagtcagct actatgattg catctgctgt gggagtaatg aatcaagtta ttcacggagt    6900
aacggtatcc ttaccgcctac aaattgaggg aaaccaaaat caattgttat ccacacttgc    6960
cacaatctgt acaggcaaaa aacaagtctc aaactgctct acaaacatcc ccttagttaa    7020
tgaccttagg tttataaatg ggatcaataa attcatcatt gaagattatg caactcatga    7080
tttctctatc ggccatccac tcaacatgcc tagctttatc ccaactgcaa cttcacccaa    7140
tggttgcaca agaattccat cctttttctct aggtaagaca cactggtgct acacacataa    7200
tgtaattaat gccaactgca aggatcatac ttcgtctaac caatatatttt ccatgggat    7260 actcgttcag accgcgtcag ggtatcctat gttcaaaacc ttaaaaatcc aatatctcag    7320
tgatggcctt aatcggaaaa gctgctcaat tgcaacagtc cctgatggat gcgcaatgta    7380
ctgttacgtc tcaactcaac ttgaaaccga cgactatgcg gggtccagcc cacctaccca    7440
gaaacttacc ctgttattct ataatgatac cgtcacagaa aggacaatat ctccaactgg    7500
tcttgaaggg aattgggcta ctttggttcc aggagtgggg agtggaatat atttcgagaa    7560
taaattgatt tttcctgcat atggggggtgt cttgccccaat agtacactcg gagttaaatc    7620
agcaagagaa ttttttccggc ctgttaatcc atataatcca tgttcaggac cacaacaaga    7680
tttagatcag cgtgctttga gatcatactt cccaagttac ttctctaatc gaagagtaca    7740
gagtgcattt cttgtctgtg cctggaatca gatcctagtt acaaattgcg agctagttgt    7800
cccctcaaac aatcagacac tgatgggtgc agaaggaaga gttttattga tcaataatcg    7860
actattatat tatcagagaa gtaccagctg gtggccgtat gaactcctct atgagatatc    7920
attcacattt acaaactctg gtcaatcatc tgtgaatatg tcctggatac ctatatattc    7980
```

```
attcactcgt cctggttcag gcaactgcag tggtraaaat gtgtgcccaa ctgcttgtgt    8040 gtcagggtt tatcttgatc cctggccatt aactccatat agccaccaat caggcattaa    8100
ccgaaatttc tatttcacag gcgcactatt aaattcaagc acaactagag taaatcctac    8160
cctttatgtc tctgcccctta ataatcttaa agtactagcc ccatatggta atcagggact   8220
gtttgcctcg tacaccacaa ccacctgctt tcaagatacc ggtgatgcta gtgtgtattg    8280
tgtttatatt atggaactag catcgaatat cgttggagaa ttccaaattc tacctgtgct    8340
aaccagattg accatcactt gagtcatagt gaatgcagtg ggaggcccta tgggcgtgct    8400
tcaatcttta tcgattatta agaaaaaaca ggccagaatg gcgggcctaa atgagatact    8460
cttacctgaa gtacatttaa actcacccat cgttagatat aagcttttct actatatatt    8520
gcatggccag ttaccaaatg atttggagcc agatgacttg ggcccactag caaatcagaa    8580
ttggaaggca attcgagctg aagaatctca ggttcatgca cgtttaaaac agatcagagt    8640
agaactcatt gcaaggattc ctagtctccg gtggacccgc tctcagaggg agattgccat    8700
actcatttgg ccaagaatac ttccaatcct gcaagcatat gatcttcggc aaagtatgca    8760
attgcccaca gtatgggaga aattgactca atccacagtt aatcttataa gtgatgggct    8820
agaacgggtt gtattacaca tcagcaatca gctgacaggc aagcctaact tgtttaccag    8880
atctcgagca ggacaagacg caaaggatta ctcaattcca tccactagag agctatctca    8940
aatatggttt aacaacgagt ggagtggatc tgtaaagacc tggcttatga ttaaatatag    9000
aatgaggcag ctaatcacaa accaaaagac aggtgagtta acagatttag taaccattgt    9060
ggatactagg tccactctat gcattattgc cccagaatta gttgctttat actccaatga    9120
gcacaaagca ttaacgtacc tcacctttga aatggtatta atggtcactg atatgttaga    9180
gggacgactt aatgtttctt ctttatgcac agctagtcat tatctgtccc ctctaaagaa    9240
gagaatcgaa attctcctaa cattagttga tgaccttgct ctacttatgg gggacaaagt    9300
atacggtgtt gtctcttcac ttgagagttt tgtttacgcc caattacagt atggtgatcc    9360
tgttgtagac attaagggta cattctacgg atttatatgt aatgagattc tcgacctact    9420
gactgaagac aacatcttta ctgaagagga ggcaaacaag gttcttctgg acttgacatc    9480
acagtttgac aatctatccc ctgatttaac tgctgagctc ctctgcatta tgagactttg    9540
gggccatccc acattaactg ccagccaagc agcatccaag gtccgagagt ccatgtgtgc    9600
tcctaaggtg ttagatttcc aaacaataat gaagaccctg gctttctttc acgcaatcct    9660
gattaacggt tataggagga gccataatgg aatctggcct cctactactc ttcatggcaa    9720
tgcccccaaa agcctcattg agatgcggca tgataattca gagcttaagt atgagtatgt    9780
cctcaagaat tggaaaagta tatctatgtt aagaatacac aaatgctttg atgcatcacc    9840
tgatgaagat ctcagcatat tcatgaaaga taaggcaatc agctgtccaa agcaagactg    9900
gatgggagta tttaggagga gcctgataaa acagcgatat cgtgatgcga atcggcctct    9960
accacaacca tccaaccgac ggctactgtt gaatttttcta gaggatgaca gattcgatcc   10020
cattaaggag cttgagtatg tcaccagtgg agaatatctt agggaccctg aatttttgtgc   10080 atcttactct ctcaaggaga aggagataaa ggctacaggt cgcatatttg ccaaaatgac   10140
aaagagaatg aggtcgtgcc aagtaattgc agaatcattg ttggccaatc atgcaggtaa   10200
attaatgaga gagaatggag ttgtcttaga ccagttaaaa ttgacaaaat ctttgttaac   10260
gatgaaccaa attggtatta tatcagagca cagccgaaga tccactgctg acaacatgac   10320
tttggcacac tccggttcaa ataagcacag aattaataat agtcaattca agaagaataa   10380
```

```
agacagtaag catgagatgc ctgatgatgg gtttgagata gcagcctgct ttctaacaac   10440
tgacctcaca aaatactgct taaattggag gtaccaagtc atcatcccct ttgcgcgtac   10500
attgaattca atgtatggta taccccacct gtttgaatgg atacatttaa ggctaatgcg   10560
aagcactctc tatgttggtg atcccttcaa tcctccatca gatcctaccc aacttgacct   10620
tgatacagct ctcaatgatg atatatttat agtttctcct cgtggaggaa tcgagggttt   10680
atgtcaaaaa ttatggacta tgatttccat ctcgacaatc atattatccg caactgaggc   10740
aaacactaga gttatgagca tggttcaggg tgacaaccaa gcaattgcaa tcaccactag   10800
agtagtacgc tcgctcagtc attccgagaa gaaggagcaa gcttataaag caagtaaatt   10860
attctttgaa aggcttaaag ctaacaacca tggaattgga caccacttaa agaacaaga    10920 aacaatcctt agttctgatt tcttcatata cagtaagagg gtgttttaca aaggtcgaat   10980
tttgactcaa gcgttaaaga acgtgagcaa gatgtgctta acagctgaca tactagggga   11040
ctgttcacaa gcatcatgct ccaatttagc tactactgta atgcgcctga ctgagaatgg   11100
ggtcgagaaa gatttgtgtt attttctaaa tgcattcatg acaatcagac aattatgtta   11160
tgatctggta ttcccccaaa ctaaatctct tagtcaggac atcactaatg cttatcttaa   11220
tcatccaata cttatctcaa gattgtgtct attaccatct caattagggg gcctaaactt   11280
tctctcgtgt agtcgcctgt tcaatagaaa cataggagac ccattagtgt ctgcaattgc   11340
tgatgtgaaa cgattaatta aagctggctg tctagatatc tgggtcctgt ataacatcct   11400
tgggaggagg cctggaaaag gtaagtggag cactctggca gctgatcctt atactttaaa   11460
catagattat ttagttcctt caacaacttt tttaaagaag catgcccaat atacattgat   11520
ggaacggagt gttaatccca tgctccgtgg agtattcagc gaaatgcag  ctgaggaaga   11580 agaggaactc gcacagtatc tattagatcg tgaggtagtc atgcccagag ttgcacatgt   11640
aatacttgcc cagtctagtt gcggcagaag aaaacagatt caaggttact tggattccac   11700
tagaactatt atcaggtatt cactggaggt gagaccattg tcagcaaaga agctgaatac   11760
agtaatagaa tataacttat tgtatctttc ctacaatttg gagattattg aaaaacccaa   11820
tatagtccaa ccttttttga atgcaatcaa tgttgatact tgtagcatcg atatagctag   11880
gtcccttaga aaactatcct gggcaacttt actgaacgga cgtcccatcg agggattaga   11940
aacacctgat cccattgaat tggtacatgg gtgtttgatc attgggtcag atgaatgtga   12000
gcattgcagc agtggtgatg acaagttcac ctggttttc ctacccaagg ggataaggct   12060
agataatgat ccggcgtcca acccacccat cagagtacct tatattggat ctaaaacaga   12120
tgaacggagg gttgcgtcaa tggcttacat caaaggagca tctgtatcac ttaaatcagc   12180
actcagacta gcgggagtat atatttgggc tttcggagat acagaggaat catggcagga   12240
tgcctatgag ttagcttcca ctcgtgttaa tctcacacta gagcaattgc aatctctcac   12300
tcctttacca acatctgcta acctagtcca cagattggat gatggcacta ctcaattaaa   12360
atttacccct gcaagctcct atgcattctc tagcttcgtt catatatcta atgactgtca   12420
agttcttgag atcgatgatc aggtaacaga ttctaacctg atttaccagc aagttatgat   12480
tactggcctt gctttaattg agacatggaa caatcctcca atcaacttct ccgttttatg   12540
aactacacta cacttgcaca caggctcatc ttgctgtata agacctgtcg agtcttgtgt   12600
agtaaatcct ccttttgcttc ctgtcccctt cattaatgtc cctcaaatga ataaatttgt   12660
atatgaccct gaaccgctca gtttgctaga gatggaaaaa attgaggaca ttgcttatca   12720
```

```
aaccagaatt ggtggtttag atcaaatccc acttctggaa aaaatacccct tactagctca    12780 cctcaccgcc aagcagatgg taaatagcat caccgggctt gatgaagcaa catctatagt    12840
aaatgacgct gtggttcaag cagactatac tagcaattgg attagtgaat gctgttacac    12900
ttacattgat tctgtgtttg tttactctgg ctgggcatta ttattggaac tttcgtacca    12960
aatgtactac ttaagaattc aaggcatcca aggaattcta gactatgtgt atatgacctt    13020
gaggaggata ccaggaatgg ctataacggg catctcatcc acaattagtc accctcgtat    13080
actcagaaga tgcatcaatc tggatgtcat agcccctatc aattctccac acatagcttc    13140
actggattac acaaaattga gcatagacgc agtaatgtgg ggaactaagc aggttttgac    13200
caacatttcg caaggtatcg attatgagat agttgttcct tctgaaagcc aactcacact    13260
cagtgataga gttctaaatc tagttgctcg aaaactatca ctactggcaa tcatctgggc    13320
caattataac tatcctccaa aggttaaagg tatgtcacct gaggacaaat gtcaggcttt    13380
aactacccat ctactccaaa ctgtcgaata tgttgagcac attcagattg aaaagacgaa    13440
catcaggagg atgattattg aaccaaaatt aactgcctac cctagtaatt tgttttatct    13500
atctcgaaag ctgcttaatg caattcgaga ttctgaagaa ggacaatttc tgattgcatc    13560
ctattataac agctttggat atctggaacc aatactaatg gaatctaaaa tattcaatct    13620
aagttcatcc gaatcagcat cccttacaga atttgatttc atcctcaact tggaattgtc    13680
tgaagccagc cttgagaaat actctctccc aagtttgctt atgacggctg agaatatgga    13740
taacccattt cctcaaccccc cctccatca tgttctcaga ccactaggtt tatcatccac    13800
atcatggtat aaaacaatca gtgttttgaa ttatattagc catatgaaga tatctgacgg    13860
tgcccatcta tatttggcag agggaagtgg agcctctatg tcacttatag agactttctt    13920
gcccggtgaa gtaatatggt acaacagcct attcaatagt ggtgagaatc ctccccaacg    13980
caattttgcc ccttttaccca cccagtttat tgaaagtgtc ccttacagat tgattcaagc    14040
aggtatagca gcaggaagtg gtgtagttca aagtttctat ccactctgga acggtaatag    14100
cgatatcact gacttaagca cgaaaactag tgtcgagtac attattcaca aggtagggggc    14160 tgatacatgt gcattggttc atgtggatct ggagggtgta cccggctcaa tgaacagtat    14220
gttggagaga gcccaagttc atgcgctact gatcacggta actgtactaa agccaggtgg    14280
cttactaatc ttgaaagctt catgggaacc ttttaatcga ttttcctttt tactcacaat    14340
actctggcaa ttcttttcaa caataaggat ccttcgatct tcatactccg acccgaataa    14400
tcacgaggta tacataatag ctacattagc tgttgatccc accacatcct cctttacaac    14460
cgctctgaat agggcgcgta ctctgaatga acagggcttt tcactcatcc cacctgaatt    14520
agtgagtgag tactggagga ggcgtgttga acaaggcag attatacagg attgtataga    14580
taaagtcata tcagagtgtg ttagagacca atatctggca gacaacaata ttatccttca    14640
ggcggggggg actccaagca caagaaaatg gttggatctg cctgactatc cgtcgttcaa    14700
tgaattacaa tcggagatgg ccagactcat aacaattcat cttaaagagg taatagaaat    14760
cctaaagggc caatcatcag atcatgacac cctattattt acttcataca atgtaggtcc    14820
cctcgggaaa ataaatacaa tactcagatt gattgttgag agaattctta tgtacactgt    14880
aaggaactgg tgcatcttgc ccactcaaac tcgtctcacc ttacgacagt ctatcgagct    14940
tggagagttt agactaagag acgtgataac acccatggag atcctaaagc tatcccccaa    15000
ccggaagtat ctgaagtctg cattaaacca atcaacattc aatcatctaa tgggagaaac    15060
atctgacatg ttgttaaatc gatcctatca aaaaagaatt tggaaagcca ttgggtgtgt    15120
```

-continued

```
aatctattgc tttggtttgc ttaccctga tgttgaagat tctgagcgca ttgatattga    15180
caatgatata cctgattatg atatccacgg ggacataatt taaatcgact aaagactcct    15240
ctggcatgat acgtcaccaa aaggttccac accagcatcc aaattcttct agaccgtaca    15300
cgacctcgaa caatcataac cacatcagta ttaaatccat aatatcattt taagaaaaaa    15360
ttgattttac tttctcccct tggt                                           15384
```

<210> SEQ ID NO 2
<211> LENGTH: 549
<212> TYPE: PRT
<213> ORGANISM: Mumps virus

<400> SEQUENCE: 2

```
Met Ser Ser Val Leu Lys Ala Phe Glu Arg Phe Thr Ile Glu Gln Glu
1               5                   10                  15

Leu Gln Asp Arg Gly Glu Glu Gly Ser Ile Pro Pro Glu Thr Leu Lys
            20                  25                  30

Ser Ala Val Lys Val Phe Val Ile Asn Thr Pro Asn Pro Thr Thr Arg
        35                  40                  45

Tyr Gln Met Leu Asn Phe Cys Leu Arg Ile Ile Cys Ser Gln Asn Ala
    50                  55                  60

Arg Ala Ser His Arg Val Gly Ala Leu Ile Thr Leu Phe Ser Leu Pro
65                  70                  75                  80

Ser Ala Gly Met Gln Asn His Ile Arg Leu Ala Asp Arg Ser Pro Glu
                85                  90                  95

Ala Gln Ile Glu Arg Cys Glu Ile Asp Gly Phe Glu Pro Gly Thr Tyr
            100                 105                 110

Arg Leu Ile Pro Asn Ala Arg Ala Asn Leu Thr Ala Asn Glu Ile Ala
        115                 120                 125

Ala Tyr Ala Leu Leu Ala Asp Asp Leu Pro Pro Thr Ile Asn Asn Gly
    130                 135                 140

Thr Pro Tyr Val His Ala Asp Val Glu Gly Gln Pro Cys Asp Glu Ile
145                 150                 155                 160

Glu Gln Phe Leu Asp Arg Cys Tyr Ser Val Leu Ile Gln Ala Trp Val
                165                 170                 175

Met Val Cys Lys Cys Met Thr Ala Tyr Asp Gln His Ala Gly Ser Ala
            180                 185                 190

Asp Arg Arg Phe Ala Lys Tyr Gln Gln Gln Gly Arg Leu Glu Ala Arg
        195                 200                 205

Tyr Met Leu Gln Pro Glu Ala Gln Arg Leu Ile Gln Thr Ala Ile Arg
    210                 215                 220

Lys Ser Leu Val Val Arg Gln Tyr Leu Thr Phe Glu Leu Gln Leu Ala
225                 230                 235                 240

Arg Arg Gln Gly Leu Leu Ser Asn Arg Tyr Tyr Ala Met Val Gly Asp
                245                 250                 255

Ile Gly Lys Tyr Ile Glu Asn Ser Gly Leu Thr Ala Phe Phe Leu Thr
            260                 265                 270

Leu Lys Tyr Ala Leu Gly Thr Lys Trp Ser Pro Leu Ser Leu Ala Ala
        275                 280                 285

Phe Thr Gly Glu Leu Thr Lys Leu Arg Ser Leu Met Met Leu Tyr Arg
    290                 295                 300

Asp Leu Gly Glu Gln Ala Arg Tyr Leu Ala Leu Leu Glu Ala Pro Gln
305                 310                 315                 320
```

```
Ile Met Asp Phe Ala Pro Gly Gly Tyr Pro Leu Ile Phe Ser Tyr Ala
            325                 330                 335
Met Gly Val Gly Thr Val Leu Asp Val Gln Met Arg Asn Tyr Thr Tyr
        340                 345                 350
Ala Arg Pro Phe Leu Asn Gly Tyr Tyr Phe Gln Ile Gly Val Glu Thr
        355                 360                 365
Ala Arg Arg Gln Gln Gly Thr Val Asp Asn Arg Val Ala Asp Asp Leu
370                 375                 380
Gly Leu Thr Pro Glu Gln Arg Thr Glu Val Thr Gln Leu Val Asp Arg
385                 390                 395                 400
Leu Ala Arg Gly Arg Gly Ala Gly Ile Pro Gly Gly Pro Val Asn Pro
                405                 410                 415
Phe Val Pro Pro Val Gln Gln Gln Pro Ala Ala Ala His Glu Asp
            420                 425                 430
Thr Pro Ala Leu Glu Glu Ser Asp Asp Asp Gly Asp Glu Asp Gly Gly
        435                 440                 445
Ala Gly Leu Gln Asn Gly Ala Gln Ala Pro Ala Ala Arg Gln Gly Gly
        450                 455                 460
Gln Asn Asp Phe Arg Val Gln Pro Leu Gln Asp Pro Ile Gln Ala Gln
465                 470                 475                 480
Leu Phe Met Pro Leu Tyr Pro Gln Val Ser Asn Ile Pro Asn His Gln
                485                 490                 495
Asn His Gln Ile Asn Arg Val Gly Gly Met Glu His Gln Asp Leu Leu
            500                 505                 510
Arg Tyr Asn Glu Asn Gly Asp Pro Gln Gln Asp Ala Arg Gly Glu His
        515                 520                 525
Gly Asn Thr Phe Pro Asn Asn Pro Asn Gln Asn Ala Gln Ser Gln Val
        530                 535                 540
Gly Asp Trp Asp Glu
545

<210> SEQ ID NO 3
<211> LENGTH: 391
<212> TYPE: PRT
<213> ORGANISM: Mumps virus

<400> SEQUENCE: 3

Met Asp Gln Phe Ile Lys Gln Asp Glu Thr Gly Asp Leu Ile Glu Thr
1               5                   10                  15
Gly Met Asn Val Ala Asn His Phe Leu Ser Ala Pro Ile Gln Gly Thr
            20                  25                  30
Asn Ser Leu Ser Lys Ala Thr Ile Ile Pro Gly Val Ala Pro Val Leu
        35                  40                  45
Ile Gly Asn Pro Glu Gln Lys Asn Ile Gln Tyr Pro Thr Thr Ser His
    50                  55                  60
Gln Gly Ser Lys Ser Lys Gly Arg Gly Ser Gly Ala Arg Pro Ile Ile
65                  70                  75                  80
Val Ser Ser Ser Glu Gly Gly Thr Gly Thr Gln Ile Pro Glu Pro
                85                  90                  95
Leu Phe Ala Gln Thr Gly Gln Gly Gly Ile Val Thr Thr Val Tyr Gln
            100                 105                 110
Asp Pro Thr Ile Gln Pro Thr Gly Ser Tyr Arg Ser Val Glu Leu Ala
        115                 120                 125
Lys Ile Gly Lys Glu Arg Met Ile Asn Arg Phe Val Glu Lys Pro Arg
    130                 135                 140
```

```
Thr Ser Thr Pro Val Thr Glu Phe Lys Arg Gly Pro Gly Ala Ala
145                 150                 155                 160

Ala Gln Gly Gln Thr Ile Gln Glu Glu Gly Ile Asp Gly Asn Gly Ala
            165                 170                 175

Ser Ala Gly Ser Lys Glu Arg Ser Gly Ser Leu Ser Gly Ala Thr Pro
            180                 185                 190

Tyr Ala His Leu Ser Leu Pro Gln Gln Asp Ser Thr Pro Ala Asn Val
            195                 200                 205

Gly Ile Ala Pro Gln Ser Ala Ile Ser Ala Asn Glu Ile Met Asp Leu
210                 215                 220

Leu Arg Gly Met Asp Ala Arg Leu Gln His Leu Glu Gln Lys Val Asp
225                 230                 235                 240

Lys Val Leu Ala Gln Gly Ser Met Val Thr Gln Ile Lys Asn Glu Leu
            245                 250                 255

Ser Thr Val Lys Thr Thr Leu Ala Thr Ile Glu Gly Met Met Ala Thr
            260                 265                 270

Val Lys Ile Met Asp Pro Gly Asn Pro Thr Gly Val Pro Val Asp Glu
            275                 280                 285

Leu Arg Arg Ser Phe Ser Asp His Val Thr Ile Val Ser Gly Pro Gly
290                 295                 300

Asp Val Ser Phe Ser Ser Gly Glu Glu Pro Thr Leu Tyr Leu Asp Glu
305                 310                 315                 320

Leu Ala Arg Pro Val Pro Lys Pro Arg Pro Ala Lys Gln Pro Lys Pro
            325                 330                 335

Gln Pro Val Lys Asp Leu Ala Gly Arg Lys Val Met Ile Thr Lys Met
            340                 345                 350

Ile Thr Asp Cys Val Ala Asn Pro Gln Met Lys Gln Val Phe Glu Gln
            355                 360                 365

Arg Leu Ala Arg Ala Ser Thr Glu Asp Ala Leu Asn Asp Ile Lys Arg
370                 375                 380

Asp Ile Ile Arg Ser Ala Ile
385                 390

<210> SEQ ID NO 4
<211> LENGTH: 224
<212> TYPE: PRT
<213> ORGANISM: Mumps virus

<400> SEQUENCE: 4

Met Asp Gln Phe Ile Lys Gln Asp Glu Thr Gly Asp Leu Ile Glu Thr
1               5                   10                  15

Gly Met Asn Val Ala Asn His Phe Leu Ser Ala Pro Ile Gln Gly Thr
            20                  25                  30

Asn Ser Leu Ser Lys Ala Thr Ile Ile Pro Gly Val Ala Pro Val Leu
        35                  40                  45

Ile Gly Asn Pro Glu Gln Lys Asn Ile Gln Tyr Pro Thr Thr Ser His
        50                  55                  60

Gln Gly Ser Lys Ser Lys Gly Arg Gly Ser Gly Ala Arg Pro Ile Ile
65                  70                  75                  80

Val Ser Ser Ser Glu Gly Gly Thr Gly Thr Gln Ile Pro Glu Pro
            85                  90                  95

Leu Phe Ala Gln Thr Gly Gln Gly Gly Ile Val Thr Thr Val Tyr Gln
            100                 105                 110

Asp Pro Thr Ile Gln Pro Thr Gly Ser Tyr Arg Ser Val Glu Leu Ala
```

```
        115                 120                 125

Lys Ile Gly Lys Glu Arg Met Ile Asn Arg Phe Val Glu Lys Pro Arg
    130                 135                 140

Thr Ser Thr Pro Val Thr Glu Phe Lys Arg Gly Ala Gly Ser Gly Cys
145                 150                 155                 160

Ser Arg Pro Asp Asn Pro Arg Gly Gly His Arg Arg Glu Trp Ser Leu
                165                 170                 175

Ser Trp Val Gln Gly Glu Val Arg Val Phe Glu Trp Cys Asn Pro Ile
            180                 185                 190

Cys Ser Pro Ile Thr Ala Thr Ala Arg Phe His Ser Cys Lys Cys Gly
        195                 200                 205

Asn Cys Pro Ala Lys Cys Asp Gln Cys Glu Arg Asp Tyr Gly Pro Pro
    210                 215                 220

<210> SEQ ID NO 5
<211> LENGTH: 171
<212> TYPE: PRT
<213> ORGANISM: Mumps virus

<400> SEQUENCE: 5

Met Asp Gln Phe Ile Lys Gln Asp Glu Thr Gly Asp Leu Ile Glu Thr
1               5                   10                  15

Gly Met Asn Val Ala Asn His Phe Leu Ser Ala Pro Ile Gln Gly Thr
            20                  25                  30

Asn Ser Leu Ser Lys Ala Thr Ile Ile Pro Gly Val Ala Pro Val Leu
        35                  40                  45

Ile Gly Asn Pro Glu Gln Lys Asn Ile Gln Tyr Pro Thr Thr Ser His
    50                  55                  60

Gln Gly Ser Lys Ser Lys Gly Arg Gly Ser Gly Ala Arg Pro Ile Ile
65                  70                  75                  80

Val Ser Ser Ser Glu Gly Gly Thr Gly Gly Thr Gln Ile Pro Glu Pro
                85                  90                  95

Leu Phe Ala Gln Thr Gly Gln Gly Gly Ile Val Thr Thr Val Tyr Gln
            100                 105                 110

Asp Pro Thr Ile Gln Pro Thr Gly Ser Tyr Arg Ser Val Glu Leu Ala
        115                 120                 125

Lys Ile Gly Lys Glu Arg Met Ile Asn Arg Phe Val Glu Lys Pro Arg
    130                 135                 140

Thr Ser Thr Pro Val Thr Glu Phe Lys Arg Gly Gly Gly Arg Glu Arg
145                 150                 155                 160

Leu Leu Lys Ala Arg Gln Ser Lys Arg Arg Ala
                165                 170

<210> SEQ ID NO 6
<211> LENGTH: 375
<212> TYPE: PRT
<213> ORGANISM: Mumps virus

<400> SEQUENCE: 6

Met Ala Gly Ser Gln Ile Lys Ile Pro Leu Pro Lys Pro Pro Asp Ser
1               5                   10                  15

Asp Ser Gln Arg Leu Asn Ala Phe Pro Val Ile Val Ala Gln Glu Gly
            20                  25                  30

Lys Gly Arg Leu Leu Arg Gln Ile Arg Leu Arg Lys Ile Leu Ser Gly
        35                  40                  45

Asp Pro Ser Asp His Gln Ile Thr Phe Val Asn Thr Tyr Gly Phe Ile
```

-continued

```
    50                  55                  60

Arg Ala Thr Pro Glu Thr Ser Glu Phe Ile Ser Glu Ser Ser Gln Gln
65                  70                  75                  80

Lys Val Thr Pro Val Val Thr Ala Cys Met Leu Ser Phe Gly Ala Gly
                85                  90                  95

Pro Val Leu Glu Asp Pro Gln His Met Leu Lys Ala Leu Asp Gln Thr
            100                 105                 110

Asp Ile Arg Val Arg Lys Thr Ala Ser Asp Lys Glu Gln Ile Leu Phe
        115                 120                 125

Glu Ile Asn Arg Ile Pro Asn Leu Phe Arg His His Gln Ile Ser Ala
    130                 135                 140

Asp His Leu Ile Gln Ala Ser Ser Asp Lys Tyr Val Lys Ser Pro Ala
145                 150                 155                 160

Lys Leu Ile Ala Gly Val Asn Tyr Ile Tyr Cys Val Thr Phe Leu Ser
                165                 170                 175

Val Thr Val Cys Ser Ala Ser Leu Lys Phe Arg Val Ala Arg Pro Leu
            180                 185                 190

Leu Ala Ala Arg Ser Arg Leu Val Arg Ala Val Gln Met Glu Val Leu
        195                 200                 205

Leu Arg Val Thr Cys Lys Lys Asp Ser Gln Met Ala Lys Ser Met Leu
    210                 215                 220

Asn Asp Pro Asp Gly Glu Gly Cys Ile Ala Ser Val Trp Phe His Leu
225                 230                 235                 240

Cys Asn Leu Cys Lys Gly Arg Asn Lys Leu Arg Ser Tyr Asp Glu Asn
                245                 250                 255

Tyr Phe Ala Ser Lys Cys Arg Lys Met Asn Leu Thr Val Ser Ile Gly
            260                 265                 270

Asp Met Trp Gly Pro Thr Ile Leu Val His Ala Gly Gly His Ile Pro
        275                 280                 285

Thr Thr Ala Lys Pro Phe Phe Asn Ser Arg Gly Trp Val Cys His Pro
    290                 295                 300

Ile His Gln Ser Ser Pro Ser Leu Ala Lys Thr Leu Trp Ser Ser Gly
305                 310                 315                 320

Cys Glu Ile Lys Ala Ala Ser Ala Ile Leu Gln Gly Ser Asp Tyr Ala
                325                 330                 335

Ser Leu Ala Lys Thr Asp Asp Ile Ile Tyr Ser Lys Ile Lys Val Asp
            340                 345                 350

Lys Asp Ala Ala Asn Tyr Lys Gly Val Ser Trp Ser Pro Phe Arg Lys
        355                 360                 365

Ser Ala Ser Met Ser Asn Leu
    370                 375

<210> SEQ ID NO 7
<211> LENGTH: 538
<212> TYPE: PRT
<213> ORGANISM: Mumps virus

<400> SEQUENCE: 7

Met Lys Ala Phe Leu Val Thr Cys Leu Ser Phe Ala Val Phe Ser Ser
1               5                   10                  15

Ser Val Cys Val Asn Ile Asn Ile Leu Gln Gln Ile Gly Tyr Ile Lys
            20                  25                  30

Gln Gln Val Arg Gln Leu Ser Tyr Tyr Ser Gln Ser Ser Ser Ser Tyr
        35                  40                  45
```

```
Ile Val Val Lys Leu Leu Pro Asn Ile Gln Pro Ile Asp Asn Ser Cys
    50                  55                  60

Glu Phe Lys Ser Val Thr Gln Tyr Asn Lys Thr Leu Ser Asn Leu Leu
65                  70                  75                  80

Leu Pro Ile Ala Glu Asn Ile Asn Asn Ile Ala Ser Pro Ser Ser Gly
                85                  90                  95

Ser Arg Arg His Lys Arg Phe Ala Gly Ile Ala Ile Gly Ile Ala Ala
                100                 105                 110

Leu Gly Val Ala Thr Ala Ala Gln Val Thr Ala Ala Val Ser Leu Val
                115                 120                 125

Gln Ala Gln Thr Asn Ala Arg Ala Ile Ala Ala Met Lys Asn Ser Ile
130                 135                 140

Gln Ala Thr Asn Arg Ala Val Phe Glu Val Lys Glu Gly Thr Gln Gln
145                 150                 155                 160

Leu Ala Ile Ala Val Gln Ala Ile Gln Asp His Ile Asn Thr Ile Met
                165                 170                 175

Asn Thr Gln Leu Asn Asn Met Ser Cys Gln Ile Leu Asp Asn Gln Leu
                180                 185                 190

Ala Thr Phe Leu Gly Leu Tyr Leu Thr Glu Leu Thr Thr Val Phe Gln
                195                 200                 205

Pro Gln Leu Ile Asn Pro Ala Leu Ser Pro Ile Ser Ile Gln Ala Leu
                210                 215                 220

Arg Ser Leu Leu Gly Ser Met Thr Pro Ala Val Val Gln Ala Thr Leu
225                 230                 235                 240

Ser Thr Ser Ile Ser Thr Ala Glu Ile Leu Ser Ala Gly Leu Met Glu
                245                 250                 255

Gly Gln Ile Val Ser Val Leu Leu Asp Glu Met Gln Met Ile Val Lys
                260                 265                 270

Ile Asn Ile Pro Thr Ile Val Thr Gln Ser Asn Ala Leu Val Ile Asp
                275                 280                 285

Phe Tyr Ser Ile Ser Ser Phe Ile Asn Asn Gln Glu Ser Ile Ile Gln
                290                 295                 300

Leu Pro Asp Arg Ile Leu Glu Ile Gly Asn Glu Gln Trp Ser Tyr Pro
305                 310                 315                 320

Ala Lys Asn Cys Lys Leu Thr Arg His His Ile Phe Cys Gln Tyr Asn
                325                 330                 335

Glu Ala Glu Arg Leu Ser Leu Glu Ser Lys Leu Cys Leu Ala Gly Asn
                340                 345                 350

Ile Ser Ala Cys Val Phe Ser Pro Ile Ala Gly Ser Tyr Met Arg Arg
                355                 360                 365

Phe Thr Ala Leu Asp Gly Thr Ile Val Ala Asn Cys Arg Ser Leu Thr
370                 375                 380

Cys Leu Cys Lys Asn Pro Ser Tyr Pro Ile Tyr Gln Pro Asp His His
385                 390                 395                 400

Ala Val Thr Thr Ile Asp Leu Thr Ala Cys Gln Thr Leu Ser Leu Asp
                405                 410                 415

Gly Leu Asp Phe Ser Ile Val Ser Leu Ser Asn Ile Thr Tyr Ala Glu
                420                 425                 430

Asn Leu Thr Ile Ser Leu Ser Gln Thr Ile Asn Thr Gln Pro Ile Asp
                435                 440                 445

Ile Ser Thr Glu Leu Ser Lys Val Asn Ala Ser Leu Gln Asn Ala Val
450                 455                 460

Lys Tyr Ile Lys Glu Ser Asn His Gln Leu Gln Ser Val Ser Val Asn
```

-continued

```
465                 470                 475                 480

Ser Lys Ile Gly Ala Ile Ile Val Ala Ala Leu Val Leu Ser Ile Leu
                485                 490                 495

Ser Ile Ile Ile Ser Leu Leu Phe Cys Cys Trp Ala Tyr Ile Ala Thr
            500                 505                 510

Lys Glu Ile Arg Arg Ile Asn Phe Lys Thr Asn His Ile Asn Thr Ile
        515                 520                 525

Ser Ser Ser Val Asp Asp Leu Ile Arg Tyr
    530                 535

<210> SEQ ID NO 8
<211> LENGTH: 57
<212> TYPE: PRT
<213> ORGANISM: Mumps virus

<400> SEQUENCE: 8

Met Pro Ala Ile Gln Pro Pro Leu Tyr Pro Thr Phe Leu Leu Leu Ile
1               5                   10                  15

Leu Leu Ser Leu Ile Val Thr Leu Tyr Val Trp Ile Ile Ser Thr Ile
            20                  25                  30

Thr Tyr Lys Thr Val Val Arg His Ala Ala Leu Tyr Gln Arg Ser Phe
        35                  40                  45

Phe Arg Trp Ser Phe Asp His Ser Leu
    50                  55

<210> SEQ ID NO 9
<211> LENGTH: 582
<212> TYPE: PRT
<213> ORGANISM: Mumps virus
<220> FEATURE:
<221> NAME/KEY: misc_feature
<222> LOCATION: (468)..(468)
<223> OTHER INFORMATION: Xaa can be any naturally occurring amino acid

<400> SEQUENCE: 9

Met Glu Pro Ser Lys Leu Phe Thr Met Ser Asp Asn Ala Thr Phe Ala
1               5                   10                  15

Pro Gly Pro Phe Ile Asn Ala Ala Asp Lys Lys Thr Phe Arg Thr Cys
            20                  25                  30

Phe Arg Ile Leu Val Leu Ser Val Gln Ala Val Thr Leu Ile Leu Val
        35                  40                  45

Ile Val Thr Leu Gly Glu Leu Val Arg Met Ile Asn Asp Gln Gly Leu
    50                  55                  60

Ser Asn Gln Leu Ser Ser Ile Ala Asp Lys Ile Arg Glu Ser Ala Thr
65                  70                  75                  80

Met Ile Ala Ser Ala Val Gly Val Met Asn Gln Val Ile His Gly Val
                85                  90                  95

Thr Val Ser Leu Pro Leu Gln Ile Glu Gly Asn Gln Asn Gln Leu Leu
            100                 105                 110

Ser Thr Leu Ala Thr Ile Cys Thr Gly Lys Lys Gln Val Ser Asn Cys
        115                 120                 125

Ser Thr Asn Ile Pro Leu Val Asn Asp Leu Arg Phe Ile Asn Gly Ile
    130                 135                 140

Asn Lys Phe Ile Ile Glu Asp Tyr Ala Thr His Asp Phe Ser Ile Gly
145                 150                 155                 160

His Pro Leu Asn Met Pro Ser Phe Ile Pro Thr Ala Thr Ser Pro Asn
                165                 170                 175
```

-continued

```
Gly Cys Thr Arg Ile Pro Ser Phe Ser Leu Gly Lys Thr His Trp Cys
                180                 185                 190
Tyr Thr His Asn Val Ile Asn Ala Asn Cys Lys Asp His Thr Ser Ser
            195                 200                 205
Asn Gln Tyr Ile Ser Met Gly Ile Leu Val Gln Thr Ala Ser Gly Tyr
        210                 215                 220
Pro Met Phe Lys Thr Leu Lys Ile Gln Tyr Leu Ser Asp Gly Leu Asn
225                 230                 235                 240
Arg Lys Ser Cys Ser Ile Ala Thr Val Pro Asp Gly Cys Ala Met Tyr
                245                 250                 255
Cys Tyr Val Ser Thr Gln Leu Glu Thr Asp Asp Tyr Ala Gly Ser Ser
            260                 265                 270
Pro Pro Thr Gln Lys Leu Thr Leu Leu Phe Tyr Asn Asp Thr Val Thr
        275                 280                 285
Glu Arg Thr Ile Ser Pro Thr Gly Leu Glu Gly Asn Trp Ala Thr Leu
    290                 295                 300
Val Pro Gly Val Gly Ser Gly Ile Tyr Phe Glu Asn Lys Leu Ile Phe
305                 310                 315                 320
Pro Ala Tyr Gly Gly Val Leu Pro Asn Ser Thr Leu Gly Val Lys Ser
                325                 330                 335
Ala Arg Glu Phe Phe Arg Pro Val Asn Pro Tyr Asn Pro Cys Ser Gly
            340                 345                 350
Pro Gln Gln Asp Leu Asp Gln Arg Ala Leu Arg Ser Tyr Phe Pro Ser
        355                 360                 365
Tyr Phe Ser Asn Arg Arg Val Gln Ser Ala Phe Leu Val Cys Ala Trp
    370                 375                 380
Asn Gln Ile Leu Val Thr Asn Cys Glu Leu Val Val Pro Ser Asn Asn
385                 390                 395                 400
Gln Thr Leu Met Gly Ala Glu Gly Arg Val Leu Leu Ile Asn Asn Arg
                405                 410                 415
Leu Leu Tyr Tyr Gln Arg Ser Thr Ser Trp Trp Pro Tyr Glu Leu Leu
            420                 425                 430
Tyr Glu Ile Ser Phe Thr Phe Thr Asn Ser Gly Gln Ser Ser Val Asn
        435                 440                 445
Met Ser Trp Ile Pro Ile Tyr Ser Phe Thr Arg Pro Gly Ser Gly Asn
450                 455                 460
Cys Ser Gly Xaa Asn Val Cys Pro Thr Ala Cys Val Ser Gly Val Tyr
465                 470                 475                 480
Leu Asp Pro Trp Pro Leu Thr Pro Tyr Ser His Gln Ser Gly Ile Asn
                485                 490                 495
Arg Asn Phe Tyr Phe Thr Gly Ala Leu Leu Asn Ser Ser Thr Thr Arg
            500                 505                 510
Val Asn Pro Thr Leu Tyr Val Ser Ala Leu Asn Asn Leu Lys Val Leu
        515                 520                 525
Ala Pro Tyr Gly Asn Gln Gly Leu Phe Ala Ser Tyr Thr Thr Thr Thr
    530                 535                 540
Cys Phe Gln Asp Thr Gly Asp Ala Ser Val Tyr Cys Val Tyr Ile Met
545                 550                 555                 560
Glu Leu Ala Ser Asn Ile Val Gly Glu Phe Gln Ile Leu Pro Val Leu
                565                 570                 575
Thr Arg Leu Thr Ile Thr
                580
```

<210> SEQ ID NO 10
<211> LENGTH: 2261
<212> TYPE: PRT
<213> ORGANISM: Mumps virus

<400> SEQUENCE: 10

```
Met Ala Gly Leu Asn Glu Ile Leu Leu Pro Glu Val His Leu Asn Ser
1               5                   10                  15

Pro Ile Val Arg Tyr Lys Leu Phe Tyr Tyr Ile Leu His Gly Gln Leu
            20                  25                  30

Pro Asn Asp Leu Glu Pro Asp Asp Leu Gly Pro Leu Ala Asn Gln Asn
        35                  40                  45

Trp Lys Ala Ile Arg Ala Glu Glu Ser Gln Val His Ala Arg Leu Lys
    50                  55                  60

Gln Ile Arg Val Glu Leu Ile Ala Arg Ile Pro Ser Leu Arg Trp Thr
65                  70                  75                  80

Arg Ser Gln Arg Glu Ile Ala Ile Leu Ile Trp Pro Arg Ile Leu Pro
                85                  90                  95

Ile Leu Gln Ala Tyr Asp Leu Arg Gln Ser Met Gln Leu Pro Thr Val
            100                 105                 110

Trp Glu Lys Leu Thr Gln Ser Thr Val Asn Leu Ile Ser Asp Gly Leu
        115                 120                 125

Glu Arg Val Val Leu His Ile Ser Asn Gln Leu Thr Gly Lys Pro Asn
    130                 135                 140

Leu Phe Thr Arg Ser Arg Ala Gly Gln Asp Ala Lys Asp Tyr Ser Ile
145                 150                 155                 160

Pro Ser Thr Arg Glu Leu Ser Gln Ile Trp Phe Asn Asn Glu Trp Ser
                165                 170                 175

Gly Ser Val Lys Thr Trp Leu Met Ile Lys Tyr Arg Met Arg Gln Leu
            180                 185                 190

Ile Thr Asn Gln Lys Thr Gly Glu Leu Thr Asp Leu Val Thr Ile Val
        195                 200                 205

Asp Thr Arg Ser Thr Leu Cys Ile Ile Ala Pro Glu Leu Val Ala Leu
    210                 215                 220

Tyr Ser Asn Glu His Lys Ala Leu Thr Tyr Leu Thr Phe Glu Met Val
225                 230                 235                 240

Leu Met Val Thr Asp Met Leu Glu Gly Arg Leu Asn Val Ser Ser Leu
                245                 250                 255

Cys Thr Ala Ser His Tyr Leu Ser Pro Leu Lys Lys Arg Ile Glu Ile
            260                 265                 270

Leu Leu Thr Leu Val Asp Asp Leu Ala Leu Leu Met Gly Asp Lys Val
        275                 280                 285

Tyr Gly Val Val Ser Ser Leu Glu Ser Phe Val Tyr Ala Gln Leu Gln
    290                 295                 300

Tyr Gly Asp Pro Val Val Asp Ile Lys Gly Thr Phe Tyr Gly Phe Ile
305                 310                 315                 320

Cys Asn Glu Ile Leu Asp Leu Leu Thr Glu Asp Asn Ile Phe Thr Glu
                325                 330                 335

Glu Glu Ala Asn Lys Val Leu Leu Asp Leu Thr Ser Gln Phe Asp Asn
            340                 345                 350

Leu Ser Pro Asp Leu Thr Ala Glu Leu Leu Cys Ile Met Arg Leu Trp
        355                 360                 365

Gly His Pro Thr Leu Thr Ala Ser Gln Ala Ala Ser Lys Val Arg Glu
    370                 375                 380
```

-continued

```
Ser Met Cys Ala Pro Lys Val Leu Asp Phe Gln Thr Ile Met Lys Thr
385                 390                 395                 400

Leu Ala Phe Phe His Ala Ile Leu Ile Asn Gly Tyr Arg Arg Ser His
            405                 410                 415

Asn Gly Ile Trp Pro Thr Thr Leu His Gly Asn Ala Pro Lys Ser
        420                 425                 430

Leu Ile Glu Met Arg His Asp Asn Ser Glu Leu Lys Tyr Glu Tyr Val
    435                 440                 445

Leu Lys Asn Trp Lys Ser Ile Ser Met Leu Arg Ile His Lys Cys Phe
450                 455                 460

Asp Ala Ser Pro Asp Glu Asp Leu Ser Ile Phe Met Lys Asp Lys Ala
465                 470                 475                 480

Ile Ser Cys Pro Lys Gln Asp Trp Met Gly Val Phe Arg Arg Ser Leu
                485                 490                 495

Ile Lys Gln Arg Tyr Arg Asp Ala Asn Arg Pro Leu Pro Gln Pro Ser
            500                 505                 510

Asn Arg Arg Leu Leu Asn Phe Leu Glu Asp Arg Phe Asp Pro
        515                 520                 525

Ile Lys Glu Leu Glu Tyr Val Thr Ser Gly Glu Tyr Leu Arg Asp Pro
    530                 535                 540

Glu Phe Cys Ala Ser Tyr Ser Leu Lys Glu Lys Glu Ile Lys Ala Thr
545                 550                 555                 560

Gly Arg Ile Phe Ala Lys Met Thr Lys Arg Met Arg Ser Cys Gln Val
                565                 570                 575

Ile Ala Glu Ser Leu Leu Ala Asn His Ala Gly Lys Leu Met Arg Glu
            580                 585                 590

Asn Gly Val Val Leu Asp Gln Leu Lys Leu Thr Lys Ser Leu Leu Thr
        595                 600                 605

Met Asn Gln Ile Gly Ile Ile Ser Glu His Ser Arg Arg Ser Thr Ala
    610                 615                 620

Asp Asn Met Thr Leu Ala His Ser Gly Ser Asn Lys His Arg Ile Asn
625                 630                 635                 640

Asn Ser Gln Phe Lys Lys Asn Lys Asp Ser Lys His Glu Met Pro Asp
                645                 650                 655

Asp Gly Phe Glu Ile Ala Ala Cys Phe Leu Thr Thr Asp Leu Thr Lys
            660                 665                 670

Tyr Cys Leu Asn Trp Arg Tyr Gln Val Ile Ile Pro Phe Ala Arg Thr
        675                 680                 685

Leu Asn Ser Met Tyr Gly Ile Pro His Leu Phe Glu Trp Ile His Leu
    690                 695                 700

Arg Leu Met Arg Ser Thr Leu Tyr Val Gly Asp Pro Phe Asn Pro Pro
705                 710                 715                 720

Ser Asp Pro Thr Gln Leu Asp Leu Asp Thr Ala Leu Asn Asp Ile
                725                 730                 735

Phe Ile Val Ser Pro Arg Gly Ile Glu Gly Leu Cys Gln Lys Leu
            740                 745                 750

Trp Thr Met Ile Ser Ile Ser Thr Ile Leu Ser Ala Thr Glu Ala
    755                 760                 765

Asn Thr Arg Val Met Ser Met Val Gln Gly Asp Asn Gln Ala Ile Ala
        770                 775                 780

Ile Thr Thr Arg Val Val Arg Ser Leu Ser His Ser Glu Lys Lys Glu
785                 790                 795                 800

Gln Ala Tyr Lys Ala Ser Lys Leu Phe Phe Glu Arg Leu Lys Ala Asn
```

```
                    805                 810                 815
Asn His Gly Ile Gly His His Leu Lys Glu Gln Glu Thr Ile Leu Ser
            820                 825                 830

Ser Asp Phe Phe Ile Tyr Ser Lys Arg Val Phe Tyr Lys Gly Arg Ile
            835                 840                 845

Leu Thr Gln Ala Leu Lys Asn Val Ser Lys Met Cys Leu Thr Ala Asp
        850                 855                 860

Ile Leu Gly Asp Cys Ser Gln Ala Ser Cys Ser Asn Leu Ala Thr Thr
865                 870                 875                 880

Val Met Arg Leu Thr Glu Asn Gly Val Glu Lys Asp Leu Cys Tyr Phe
                885                 890                 895

Leu Asn Ala Phe Met Thr Ile Arg Gln Leu Cys Tyr Asp Leu Val Phe
            900                 905                 910

Pro Gln Thr Lys Ser Leu Ser Gln Asp Ile Thr Asn Ala Tyr Leu Asn
            915                 920                 925

His Pro Ile Leu Ile Ser Arg Leu Cys Leu Leu Pro Ser Gln Leu Gly
    930                 935                 940

Gly Leu Asn Phe Leu Ser Cys Ser Arg Leu Phe Asn Arg Asn Ile Gly
945                 950                 955                 960

Asp Pro Leu Val Ser Ala Ile Ala Asp Val Lys Arg Leu Ile Lys Ala
                965                 970                 975

Gly Cys Leu Asp Ile Trp Val Leu Tyr Asn Ile Leu Gly Arg Arg Pro
            980                 985                 990

Gly Lys Gly Lys Trp Ser Thr Leu Ala Ala Asp Pro Tyr Thr Leu Asn
        995                 1000                1005

Ile Asp Tyr Leu Val Pro Ser Thr Thr Phe Leu Lys Lys His Ala
    1010                1015                1020

Gln Tyr Thr Leu Met Glu Arg Ser Val Asn Pro Met Leu Arg Gly
    1025                1030                1035

Val Phe Ser Glu Asn Ala Ala Glu Glu Glu Glu Leu Ala Gln
    1040                1045                1050

Tyr Leu Leu Asp Arg Glu Val Val Met Pro Arg Val Ala His Val
    1055                1060                1065

Ile Leu Ala Gln Ser Ser Cys Gly Arg Arg Lys Gln Ile Gln Gly
    1070                1075                1080

Tyr Leu Asp Ser Thr Arg Thr Ile Ile Arg Tyr Ser Leu Glu Val
    1085                1090                1095

Arg Pro Leu Ser Ala Lys Lys Leu Asn Thr Val Ile Glu Tyr Asn
    1100                1105                1110

Leu Leu Tyr Leu Ser Tyr Asn Leu Glu Ile Ile Glu Lys Pro Asn
    1115                1120                1125

Ile Val Gln Pro Phe Leu Asn Ala Ile Asn Val Asp Thr Cys Ser
    1130                1135                1140

Ile Asp Ile Ala Arg Ser Leu Arg Lys Leu Ser Trp Ala Thr Leu
    1145                1150                1155

Leu Asn Gly Arg Pro Ile Glu Gly Leu Glu Thr Pro Asp Pro Ile
    1160                1165                1170

Glu Leu Val His Gly Cys Leu Ile Ile Gly Ser Asp Glu Cys Glu
    1175                1180                1185

His Cys Ser Ser Gly Asp Asp Lys Phe Thr Trp Phe Phe Leu Pro
    1190                1195                1200

Lys Gly Ile Arg Leu Asp Asn Asp Pro Ala Ser Asn Pro Pro Ile
    1205                1210                1215
```

-continued

```
Arg Val Pro Tyr Ile Gly Ser Lys Thr Asp Glu Arg Arg Val Ala
    1220            1225                1230

Ser Met Ala Tyr Ile Lys Gly Ala Ser Val Ser Leu Lys Ser Ala
    1235            1240                1245

Leu Arg Leu Ala Gly Val Tyr Ile Trp Ala Phe Gly Asp Thr Glu
    1250            1255                1260

Glu Ser Trp Gln Asp Ala Tyr Glu Leu Ala Ser Thr Arg Val Asn
    1265            1270                1275

Leu Thr Leu Glu Gln Leu Gln Ser Leu Thr Pro Leu Pro Thr Ser
    1280            1285                1290

Ala Asn Leu Val His Arg Leu Asp Asp Gly Thr Thr Gln Leu Lys
    1295            1300                1305

Phe Thr Pro Ala Ser Ser Tyr Ala Phe Ser Ser Phe Val His Ile
    1310            1315                1320

Ser Asn Asp Cys Gln Val Leu Glu Ile Asp Asp Gln Val Thr Asp
    1325            1330                1335

Ser Asn Leu Ile Tyr Gln Gln Val Met Ile Thr Gly Leu Ala Leu
    1340            1345                1350

Ile Glu Thr Trp Asn Asn Pro Pro Ile Asn Phe Ser Val Tyr Glu
    1355            1360                1365

Thr Thr Leu His Leu His Thr Gly Ser Ser Cys Cys Ile Arg Pro
    1370            1375                1380

Val Glu Ser Cys Val Val Asn Pro Pro Leu Leu Pro Val Pro Phe
    1385            1390                1395

Ile Asn Val Pro Gln Met Asn Lys Phe Val Tyr Asp Pro Glu Pro
    1400            1405                1410

Leu Ser Leu Leu Glu Met Glu Lys Ile Glu Asp Ile Ala Tyr Gln
    1415            1420                1425

Thr Arg Ile Gly Gly Leu Asp Gln Ile Pro Leu Leu Glu Lys Ile
    1430            1435                1440

Pro Leu Leu Ala His Leu Thr Ala Lys Gln Met Val Asn Ser Ile
    1445            1450                1455

Thr Gly Leu Asp Glu Ala Thr Ser Ile Val Asn Asp Ala Val Val
    1460            1465                1470

Gln Ala Asp Tyr Thr Ser Asn Trp Ile Ser Glu Cys Cys Tyr Thr
    1475            1480                1485

Tyr Ile Asp Ser Val Phe Val Tyr Ser Gly Trp Ala Leu Leu Leu
    1490            1495                1500

Glu Leu Ser Tyr Gln Met Tyr Tyr Leu Arg Ile Gln Gly Ile Gln
    1505            1510                1515

Gly Ile Leu Asp Tyr Val Tyr Met Thr Leu Arg Arg Ile Pro Gly
    1520            1525                1530

Met Ala Ile Thr Gly Ile Ser Ser Thr Ile Ser His Pro Arg Ile
    1535            1540                1545

Leu Arg Arg Cys Ile Asn Leu Asp Val Ile Ala Pro Ile Asn Ser
    1550            1555                1560

Pro His Ile Ala Ser Leu Asp Tyr Thr Lys Leu Ser Ile Asp Ala
    1565            1570                1575

Val Met Trp Gly Thr Lys Gln Val Leu Thr Asn Ile Ser Gln Gly
    1580            1585                1590

Ile Asp Tyr Glu Ile Val Val Pro Ser Glu Ser Gln Leu Thr Leu
    1595            1600                1605
```

```
Ser Asp Arg Val Leu Asn Leu Val Ala Arg Lys Leu Ser Leu Leu
    1610            1615                1620

Ala Ile Ile Trp Ala Asn Tyr Asn Tyr Pro Pro Lys Val Lys Gly
    1625            1630                1635

Met Ser Pro Glu Asp Lys Cys Gln Ala Leu Thr Thr His Leu Leu
    1640            1645                1650

Gln Thr Val Glu Tyr Val Glu His Ile Gln Ile Glu Lys Thr Asn
    1655            1660                1665

Ile Arg Arg Met Ile Ile Glu Pro Lys Leu Thr Ala Tyr Pro Ser
    1670            1675                1680

Asn Leu Phe Tyr Leu Ser Arg Lys Leu Leu Asn Ala Ile Arg Asp
    1685            1690                1695

Ser Glu Glu Gly Gln Phe Leu Ile Ala Ser Tyr Tyr Asn Ser Phe
    1700            1705                1710

Gly Tyr Leu Glu Pro Ile Leu Met Glu Ser Lys Ile Phe Asn Leu
    1715            1720                1725

Ser Ser Ser Glu Ser Ala Ser Leu Thr Glu Phe Asp Phe Ile Leu
    1730            1735                1740

Asn Leu Glu Leu Ser Glu Ala Ser Leu Glu Lys Tyr Ser Leu Pro
    1745            1750                1755

Ser Leu Leu Met Thr Ala Glu Asn Met Asp Asn Pro Phe Pro Gln
    1760            1765                1770

Pro Pro Leu His His Val Leu Arg Pro Leu Gly Leu Ser Ser Thr
    1775            1780                1785

Ser Trp Tyr Lys Thr Ile Ser Val Leu Asn Tyr Ile Ser His Met
    1790            1795                1800

Lys Ile Ser Asp Gly Ala His Leu Tyr Leu Ala Glu Gly Ser Gly
    1805            1810                1815

Ala Ser Met Ser Leu Ile Glu Thr Phe Leu Pro Gly Glu Val Ile
    1820            1825                1830

Trp Tyr Asn Ser Leu Phe Asn Ser Gly Glu Asn Pro Pro Gln Arg
    1835            1840                1845

Asn Phe Ala Pro Leu Pro Thr Gln Phe Ile Glu Ser Val Pro Tyr
    1850            1855                1860

Arg Leu Ile Gln Ala Gly Ile Ala Ala Gly Ser Gly Val Val Gln
    1865            1870                1875

Ser Phe Tyr Pro Leu Trp Asn Gly Asn Ser Asp Ile Thr Asp Leu
    1880            1885                1890

Ser Thr Lys Thr Ser Val Glu Tyr Ile Ile His Lys Val Gly Ala
    1895            1900                1905

Asp Thr Cys Ala Leu Val His Val Asp Leu Glu Gly Val Pro Gly
    1910            1915                1920

Ser Met Asn Ser Met Leu Glu Arg Ala Gln Val His Ala Leu Leu
    1925            1930                1935

Ile Thr Val Thr Val Leu Lys Pro Gly Gly Leu Leu Ile Leu Lys
    1940            1945                1950

Ala Ser Trp Glu Pro Phe Asn Arg Phe Ser Phe Leu Leu Thr Ile
    1955            1960                1965

Leu Trp Gln Phe Phe Ser Thr Ile Arg Ile Leu Arg Ser Ser Tyr
    1970            1975                1980

Ser Asp Pro Asn Asn His Glu Val Tyr Ile Ile Ala Thr Leu Ala
    1985            1990                1995

Val Asp Pro Thr Thr Ser Ser Phe Thr Thr Ala Leu Asn Arg Ala
```

-continued

```
                     2000                  2005                       2010
Arg  Thr  Leu  Asn  Glu  Gln  Gly  Phe  Ser  Leu  Ile  Pro  Pro  Glu  Leu
     2015                      2020                      2025

Val  Ser  Glu  Tyr  Trp  Arg  Arg  Arg  Val  Glu  Gln  Gly  Gln  Ile  Ile
     2030                      2035                      2040

Gln  Asp  Cys  Ile  Asp  Lys  Val  Ile  Ser  Glu  Cys  Val  Arg  Asp  Gln
     2045                      2050                      2055

Tyr  Leu  Ala  Asp  Asn  Asn  Ile  Ile  Leu  Gln  Ala  Gly  Gly  Thr  Pro
     2060                      2065                      2070

Ser  Thr  Arg  Lys  Trp  Leu  Asp  Leu  Pro  Asp  Tyr  Pro  Ser  Phe  Asn
     2075                      2080                      2085

Glu  Leu  Gln  Ser  Glu  Met  Ala  Arg  Leu  Ile  Thr  Ile  His  Leu  Lys
     2090                      2095                      2100

Glu  Val  Ile  Glu  Ile  Leu  Lys  Gly  Gln  Ser  Ser  Asp  His  Asp  Thr
     2105                      2110                      2115

Leu  Leu  Phe  Thr  Ser  Tyr  Asn  Val  Gly  Pro  Leu  Gly  Lys  Ile  Asn
     2120                      2125                      2130

Thr  Ile  Leu  Arg  Leu  Ile  Val  Glu  Arg  Ile  Leu  Met  Tyr  Thr  Val
     2135                      2140                      2145

Arg  Asn  Trp  Cys  Ile  Leu  Pro  Thr  Gln  Thr  Arg  Leu  Thr  Leu  Arg
     2150                      2155                      2160

Gln  Ser  Ile  Glu  Leu  Gly  Glu  Phe  Arg  Leu  Arg  Asp  Val  Ile  Thr
     2165                      2170                      2175

Pro  Met  Glu  Ile  Leu  Lys  Leu  Ser  Pro  Asn  Arg  Lys  Tyr  Leu  Lys
     2180                      2185                      2190

Ser  Ala  Leu  Asn  Gln  Ser  Thr  Phe  Asn  His  Leu  Met  Gly  Glu  Thr
     2195                      2200                      2205

Ser  Asp  Met  Leu  Leu  Asn  Arg  Ser  Tyr  Gln  Lys  Arg  Ile  Trp  Lys
     2210                      2215                      2220

Ala  Ile  Gly  Cys  Val  Ile  Tyr  Cys  Phe  Gly  Leu  Leu  Thr  Pro  Asp
     2225                      2230                      2235

Val  Glu  Asp  Ser  Glu  Arg  Ile  Asp  Ile  Asp  Asn  Asp  Ile  Pro  Asp
     2240                      2245                      2250

Tyr  Asp  Ile  His  Gly  Asp  Ile  Ile
     2255                      2260
```